United States Patent
Harley-Trochimczyk et al.

(10) Patent No.: US 11,484,232 B2
(45) Date of Patent: Nov. 1, 2022

(54) SYSTEMS, DEVICES, AND METHODS TO COMPENSATE FOR TEMPERATURE EFFECTS ON SENSORS

(71) Applicant: DexCom, Inc., San Diego, CA (US)

(72) Inventors: Anna Claire Harley-Trochimczyk, San Diego, CA (US); Sebastian Böhm, San Diego, CA (US); Rui Ma, San Diego, CA (US); Disha B. Sheth, Oceanside, CA (US); Minglian Shi, San Diego, CA (US); Kamuran Turksoy, San Diego, CA (US)

(73) Assignee: Dexcom, Inc., San Diego, CA (US)

( * ) Notice: Subject to any disclaimer, the term of this patent is extended or adjusted under 35 U.S.C. 154(b) by 675 days.

(21) Appl. No.: 16/254,080

(22) Filed: Jan. 22, 2019

(65) Prior Publication Data

US 2019/0227022 A1    Jul. 25, 2019

Related U.S. Application Data

(60) Provisional application No. 62/620,775, filed on Jan. 23, 2018.

(51) Int. Cl.
*A61B 5/00* (2006.01)
*A61B 5/1495* (2006.01)
(Continued)

(52) U.S. Cl.
CPC .......... *A61B 5/1495* (2013.01); *A61B 5/0022* (2013.01); *A61B 5/01* (2013.01);
(Continued)

(58) Field of Classification Search
CPC .. G16H 50/20; A61B 5/7221; A61B 5/14532; A61B 5/01
See application file for complete search history.

(56) References Cited

U.S. PATENT DOCUMENTS

| | | |
|---|---|---|
| 6,001,067 A | 12/1999 | Shults et al. |
| 6,180,416 B1 | 1/2001 | Kurnik et al. |

(Continued)

FOREIGN PATENT DOCUMENTS

| | | |
|---|---|---|
| CN | 104764778 A | 7/2015 |
| EP | 2751577 B1 | 4/2019 |

(Continued)

OTHER PUBLICATIONS

Buckingham M.D.B., et al., "Preventing Hypoglycemia Using Predictive Alarm Algorithms and Insulin Pump Suspension," Diabetes Technology & Therapeutics, vol. 11, No. 2, 2009, pp. 93-97.

(Continued)

*Primary Examiner* — Christian Jang
(74) *Attorney, Agent, or Firm* — Schwegman Lundberg & Woessner, P.A.

(57) ABSTRACT

This document discusses, among other things, systems and methods to compensate for the effects of temperature on sensors, such as analyte sensor. An example method may include determining a temperature-compensated glucose concentration level by receiving a temperature signal indicative of a temperature parameter of an external component, receiving a glucose signal indicative of an in vivo glucose concentration level, and determining a compensated glucose concentration level based on the glucose signal, the temperature signal, and a delay parameter.

20 Claims, 26 Drawing Sheets

(51) Int. Cl.
  *A61B 5/0205* (2006.01)
  *A61B 5/145* (2006.01)
  *A61B 5/1486* (2006.01)
  *A61B 5/01* (2006.01)
  *G16H 50/20* (2018.01)
  *G01N 27/327* (2006.01)
  *A61B 5/024* (2006.01)
  *A61B 5/11* (2006.01)

(52) U.S. Cl.
  CPC ........ *A61B 5/0205* (2013.01); *A61B 5/14532* (2013.01); *A61B 5/14865* (2013.01); *A61B 5/7203* (2013.01); *A61B 5/7221* (2013.01); *G01N 27/3274* (2013.01); *G16H 50/20* (2018.01); *A61B 5/024* (2013.01); *A61B 5/1112* (2013.01); *A61B 5/1118* (2013.01); *A61B 5/681* (2013.01); *A61B 2560/0238* (2013.01); *A61B 2560/0252* (2013.01); *A61B 2562/0219* (2013.01); *A61B 2562/0247* (2013.01)

(56) References Cited

U.S. PATENT DOCUMENTS

| | | |
|---|---|---|
| 6,424,847 B1 | 7/2002 | Mastrototaro et al. |
| 6,477,395 B2 | 11/2002 | Schulman et al. |
| 6,484,046 B1 | 11/2002 | Say et al. |
| 6,512,939 B1 | 1/2003 | Colvin et al. |
| 6,565,509 B1 | 5/2003 | Say et al. |
| 6,579,690 B1 | 6/2003 | Bonnecaze et al. |
| 6,882,940 B2 | 4/2005 | Potts et al. |
| 7,699,973 B2 | 4/2010 | Tonks |
| 7,768,386 B2 | 8/2010 | Hayter et al. |
| 7,781,222 B2 | 8/2010 | Wu et al. |
| 7,828,728 B2 | 11/2010 | Boock et al. |
| 8,092,386 B1 | 1/2012 | Wenzel et al. |
| 8,116,840 B2 | 2/2012 | Feldman et al. |
| 8,148,162 B2 | 4/2012 | Wu et al. |
| 8,162,829 B2 | 4/2012 | Say et al. |
| 8,185,181 B2 | 5/2012 | Feldman et al. |
| 8,187,183 B2 | 5/2012 | Jin et al. |
| 8,219,173 B2 | 7/2012 | Budiman et al. |
| 8,219,174 B2 | 7/2012 | Feldman et al. |
| 8,219,175 B2 | 7/2012 | Feldman et al. |
| 8,224,415 B2 | 7/2012 | Budiman |
| 8,260,392 B2 | 9/2012 | Say et al. |
| 8,271,085 B2 | 9/2012 | Lippert et al. |
| 8,273,022 B2 | 9/2012 | Say et al. |
| 8,376,945 B2 | 2/2013 | Hayter et al. |
| 8,380,273 B2 | 2/2013 | Say et al. |
| 8,410,940 B2 | 4/2013 | Samuelsson et al. |
| 8,445,290 B2 | 5/2013 | Wu et al. |
| 8,483,967 B2 | 7/2013 | Harper |
| 8,532,935 B2 | 9/2013 | Budiman |
| 8,622,903 B2 | 1/2014 | Jin et al. |
| 8,630,692 B2 | 1/2014 | Wenzel et al. |
| 8,676,284 B2 | 3/2014 | He |
| 8,744,547 B2 | 6/2014 | Budiman et al. |
| 8,841,133 B2 | 9/2014 | Wu et al. |
| 8,880,137 B2 | 11/2014 | Say et al. |
| 9,050,041 B2 | 6/2015 | Feldman et al. |
| 9,066,694 B2 | 6/2015 | Say et al. |
| 9,125,548 B2 | 9/2015 | Hayter |
| 9,204,827 B2 | 12/2015 | Hayter et al. |
| 9,310,230 B2 | 4/2016 | Harper |
| 9,326,708 B2 | 5/2016 | Hanson et al. |
| 9,345,426 B2 | 5/2016 | Colvin, Jr. et al. |
| 9,380,965 B2 | 7/2016 | Ouyang et al. |
| 9,414,775 B2 | 8/2016 | Colvin, Jr. et al. |
| 9,498,159 B2 | 11/2016 | Heller et al. |
| 9,662,056 B2 | 5/2017 | Budiman et al. |
| 9,757,057 B2 | 9/2017 | Gallant et al. |
| 9,962,091 B2 | 5/2018 | Jin et al. |
| 9,974,472 B2 | 5/2018 | Hayter et al. |
| 10,002,233 B2 | 6/2018 | Hayter et al. |
| 10,089,446 B2 | 10/2018 | Budiman |
| 10,117,606 B2 | 11/2018 | Feldman et al. |
| 10,335,075 B2 | 7/2019 | Vanslyke et al. |
| 10,398,363 B2 | 9/2019 | Hayter et al. |
| 10,575,765 B2 | 3/2020 | Brill |
| 10,610,141 B2 | 4/2020 | Böhm et al. |
| 10,638,979 B2 | 5/2020 | Gupta et al. |
| 11,020,019 B2 | 6/2021 | DeHennis et al. |
| 2002/0161288 A1 | 10/2002 | Shin et al. |
| 2005/0027463 A1 | 2/2005 | Goode, Jr. et al. |
| 2006/0020187 A1 | 1/2006 | Brister et al. |
| 2007/0027385 A1 | 2/2007 | Brister et al. |
| 2008/0108942 A1 | 5/2008 | Brister et al. |
| 2008/0119703 A1 | 5/2008 | Brister et al. |
| 2008/0255808 A1 | 10/2008 | Hayter |
| 2010/0280348 A1 | 11/2010 | Wenzel et al. |
| 2011/0152658 A1* | 6/2011 | Peyser ................. A61B 5/1495 600/365 |
| 2011/0237917 A1* | 9/2011 | Roy ..................... A61B 5/7203 600/365 |
| 2012/0283542 A1 | 11/2012 | McGarraugh |
| 2013/0158376 A1 | 6/2013 | Hayter et al. |
| 2013/0325352 A1 | 12/2013 | Greene et al. |
| 2014/0005508 A1 | 1/2014 | Estes et al. |
| 2015/0351672 A1 | 12/2015 | Vanslyke et al. |
| 2016/0245791 A1 | 8/2016 | Hayter et al. |
| 2018/0188199 A1 | 7/2018 | Wu |
| 2018/0263539 A1 | 9/2018 | Javey et al. |
| 2018/0368685 A1 | 12/2018 | DeHennis |
| 2019/0069823 A1 | 3/2019 | Feldman et al. |
| 2019/0223765 A1 | 7/2019 | Harley-Trochimczyk et al. |
| 2019/0223766 A1 | 7/2019 | Harley-Trochimczyk et al. |
| 2020/0029871 A1 | 1/2020 | Hayter et al. |
| 2020/0388399 A1 | 12/2020 | Kozin et al. |
| 2021/0059542 A1 | 3/2021 | Gopalakrishnan |

FOREIGN PATENT DOCUMENTS

| | | |
|---|---|---|
| WO | WO-2020065339 A1 | 4/2020 |
| WO | WO-2020092890 A1 | 5/2020 |
| WO | WO-2020191494 A1 | 10/2020 |
| WO | WO-2020230123 A1 | 11/2020 |
| WO | WO-2020234728 A1 | 11/2020 |

OTHER PUBLICATIONS

Communication for the EP application. 19743525.8 dated Sep. 4, 2020, 3 pages.

Extended European Search Report for Application No. 20157783.0 dated Jul. 14, 2020, 11 pages.

International Search Report and Written Opinion for Application No. PCT/US2019/014579 dated May 23, 2019.

Extended European Search Report for Application No. 19743525.8, dated Sep. 6, 2021, 9 pages.

\* cited by examiner

SYSTEMS, DEVICES, AND METHODS TO COMPENSATE FOR TEMPERATURE EFFECTS ON SENSORS

INCORPORATION BY REFERENCE TO RELATED APPLICATIONS

Any and all priority claims identified in the Application Data Sheet, or any correction thereto, are hereby incorporated by reference under 37 CFR 1.57. This application claims the benefit of U.S. Provisional Application No. 62/620,775, filed Jan. 23, 2018. The aforementioned application is incorporated by reference herein in its entirety, and is hereby expressly made a part of this specification.

TECHNICAL FIELD

The present development relates generally to medical devices such as analyte sensors, and more particularly, but not by way of limitation, to systems, devices, and methods to compensate for effects of temperature on analytes sensors.

BACKGROUND

Diabetes is a metabolic condition relating to the production or use of insulin by the body. Insulin is a hormone that allows the body to use glucose for energy, or store glucose as fat.

When a person eats a meal that contains carbohydrates, the food is processed by the digestive system, which produces glucose in the person's blood. Blood glucose can be used for energy or stored as fat. The body normally maintains blood glucose levels in a range that provides sufficient energy to support bodily functions and avoids problems that can arise when glucose levels are too high, or too low. Regulation of blood glucose levels depends on the production and use of insulin, which regulates the movement of blood glucose into cells.

When the body does not produce enough insulin, or when the body is unable to effectively use insulin that is present, blood sugar levels can elevate beyond normal ranges. The state of having a higher than normal blood sugar level is called "hyperglycemia." Chronic hyperglycemia can lead to a number of health problems, such as cardiovascular disease, cataract and other eye problems, nerve damage (neuropathy), and kidney damage. Hyperglycemia can also lead to acute problems, such as diabetic ketoacidosis—a state in which the body becomes excessively acidic due to the presence of blood glucose and ketones, which are produced when the body cannot use glucose. The state of having lower than normal blood glucose levels is called "hypoglycemia." Severe hypoglycemia can lead to acute crises that can result in seizures or death.

A diabetes patient can receive insulin to manage blood glucose levels. Insulin can be received, for example, through a manual injection with a needle. Wearable insulin pumps are also available. Diet and exercise also affect blood glucose levels. A glucose sensor can provide an estimated glucose concentration level, which can be used as guidance by a patient or caregiver.

Diabetes conditions are sometimes referred to as "Type 1" and "Type 2". A Type 1 diabetes patient is typically able to use insulin when it is present, but the body is unable to produce sufficient amounts of insulin, because of a problem with the insulin-producing beta cells of the pancreas. A Type 2 diabetes patient may produce some insulin, but the patient has become "insulin resistant" due to a reduced sensitivity to insulin. The result is that even though insulin is present in the body, the insulin is not sufficiently used by the patient's body to effectively regulate blood sugar levels.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

This document discusses, among other things, systems, devices, and methods to determine subcutaneous temperatures or compensate for the effects of temperature on an analyte sensor, such as a glucose sensor.

An Example (e.g., "Example 1") of subject matter (e.g., a system) may include determining a temperature-compensated glucose concentration level by receiving a temperature signal indicative of a temperature parameter of an external component, receiving a glucose signal indicative of an in vivo glucose concentration level, and determining a compensated glucose concentration level based on the glucose signal, the temperature signal, and a delay parameter.

In Example 2, the subject matter of Example 1 may optionally be configured such that the temperature parameter is a temperature, a temperature change, or a temperature offset.

In Example 3, the subject matter of any one or more of Examples 1-2 may optionally be configured such that the temperature parameter is detected at a first time and the glucose concentration level is detected at a second time after the first time may be configured such that the delay parameter includes a delay time period between the first time and the second time that accounts for a delay between a first temperature change at the external component and a second temperature change proximate a glucose sensor.

In Example 4, the subject matter of any one or more of Examples 1-3 may optionally include adjusting the delay time period based upon a temperature rate of change.

In Example 5, the subject matter of any one or more of Examples 1-4 may optionally include adjusting the delay time period based upon a detected condition.

In Example 6, the subject matter of any one or more of Examples 1-5 may optionally be configured such that the detected condition includes a sudden change in temperature.

In Example 7, the subject matter of Examples 5-6 may optionally be configured such that the detected condition includes exercise.

In Example 8, the subject matter of any one or more of Examples 1-7 may optionally be configured such that detecting a glucose signal includes receiving a glucose signal from a wearable glucose sensor.

In Example 9, the subject matter of Example 8 may optionally be configured such that detecting a temperature signal includes measuring a temperature parameter of a component of the wearable glucose sensor.

In Example 10, the subject matter Example 8 or 9 may optionally be configured such that determining a compensated glucose concentration level includes executing instructions on a processor to receive the glucose signal and the temperature signal and determine the compensated glucose concentration level using the glucose signal, the temperature signal, and the delay parameter.

In Example 11, the subject matter of any one or more of Examples 8-10 may optionally include storing a value corresponding to the temperature parameter in a memory circuit and retrieving the stored value from the memory circuit for use in determining the compensated glucose concentration level.

In Example 12, the subject matter of any one or more of Examples 1-11 may optionally include delivering a therapy based at least in part on the compensated glucose concentration level.

An Example (e.g., "Example 13") of subject matter (e.g., a system) may include a glucose sensor circuit configured to generate a glucose signal representative of a glucose concentration level, a temperature sensor circuit configured to generate a temperature signal indicative of a temperature parameter, and a processor configured to determine a compensated glucose concentration level based on the glucose signal, the temperature signal, and a delay parameter.

In Example 14, the subject matter of Example 13 may be configured such that the temperature parameter is a temperature, a temperature change, or a temperature offset.

In Example 15, the subject matter of Example 13 or 14 may be configured such that the delay parameter includes a delay time period that accounts for a delay between a first temperature change at the temperature sensor circuit and a second temperature change at the glucose sensor circuit.

In Example 16, the subject matter of Example 15 may be configured such that the processor adjusts the delay time period based upon a temperature rate of change determined using the temperature parameter.

In Example 17, the subject matter of Example 15 or 16 may be configured such that the processor adjusts the delay time period based upon a detected condition or determined state.

In Example 18, the subject matter of any one or any combination of Examples 13-17 may be configured such that the processor executes instructions to receive the glucose signal and the temperature signal and apply the delay parameter to determine the compensated glucose concentration level.

In Example 19, the subject matter of any one or any combination of Examples 13-19 may further include a memory circuit that may be configured such that the system stores a value corresponding to the temperature parameter in the memory circuit, and the processor later retrieves the stored value from memory for use in determining the compensated glucose concentration level.

In Example 20, the subject matter of any one or any combination of Examples 13-19 may be configured such that the glucose sensor circuit includes an electrode operatively coupled to electronic circuitry configured to generate the glucose signal and a membrane over at least a portion of the electrode, the membrane including an enzyme configured to catalyze a reaction of glucose and oxygen from a biological fluid in contact with the membrane in vivo.

An example (Example 21) of subject matter (e.g., a system, device, or method) of determining a temperature-compensated glucose concentration level may include receiving a glucose sensor signal, receiving a temperature parameter signal, receiving a third sensor signal, evaluating the temperature parameter signal using the third sensor signal to generate an evaluated temperature parameter signal, and determining a temperature-compensated glucose concentration level based on the evaluated temperature parameter signal and the glucose sensor signal.

In Example 22, the subject matter of Example 21 may be configured such that receiving a third sensor signal includes receiving a heart rate signal.

In Example 23, the subject matter of Example 21 or 22 may be configured such that receiving a third signal includes receiving a pressure signal.

In Example 24, the subject matter of any one or any combination of Examples 21-23 may be configured such that receiving a third signal includes receiving an activity signal.

In Example 25, the subject matter of any one or any combination of Examples 21-24 may be configured such that receiving the third sensor signal includes receiving a location signal.

In Example 26, the subject matter of any one or any combination of Examples 21-25 may be configured such that evaluating the temperature parameter signal includes determining a presence at a location having a known temperature characteristic.

In Example 27, the subject matter of any one or any combination of Examples 21-26 may be configured such that the method includes determining a presence at a location having a known ambient temperature characteristic.

In Example 28, the subject matter of any one or any combination of Examples 21-27 may be configured such that the method includes determining a presence at a location having an immersive water environment.

In Example 29, the subject matter of Example 28 may be configured such that the immersive water environment is a pool or beach.

In Example 30, the subject matter of any one or any combination of Examples 21-29 may be configured such that receiving the third sensor signal includes receiving temperature information from an ambient temperature sensor.

In Example 31, the subject matter of any one or any combination of Examples 21-30 may be configured such that receiving the third sensor signal includes receiving information from a wearable device.

In Example 32, the subject matter of Example 31 may be configured such that receiving the third sensor signal includes receiving information from a watch.

In Example 33, the subject matter of any one or any combination of Examples 21-32 may be configured such that receiving the third sensor signal includes receiving temperature information from a physiologic temperature sensor. In some examples, the subject matter may include a watch or other wearable device that includes the temperature sensor.

In Example 34, the subject matter of any one or any combination of Examples 21-33 may be configured such that receiving a temperature parameter signal includes receiving a signal indicative of a temperature, a temperature change, or a temperature offset.

In Example 35, the subject matter of any one or any combination of Examples 21-34 may be configured such that receiving a third signal includes receiving an accelerometer signal.

In Example 36, the subject matter of any one or any combination of Examples 21-35 may further include detecting exercise using the third signal.

In Example 37, the subject matter of any one or any combination of Examples 21-36 may be configured such that evaluating the temperature parameter signal includes determining that a change in temperature parameter signal is consistent with an exercise session.

In Example 38, the subject matter of any one or any combination of Examples 21-37 may be configured such that evaluating the temperature parameter signal includes determining that the temperature parameter signal is consistent with an occurrence of an elevated body temperature due to exercise.

In Example 39, the subject matter of any one or any combination of Examples 21-38 may be configured such that determining a temperature-compensated glucose concentration level includes applying the temperature parameter signal to an exercise model.

In Example 40, the subject matter of any one or any combination of Examples 21-39 may be configured such that the method includes applying an exercise model when exercise is detected and a change in the temperature parameter signal indicates a reduction in temperature (which may, for example, suggest exercise in a cool temperature environment or convectively cooled environment).

In Example 41, the subject matter of any one or any combination of Examples 21-40 may be configured such that the third signal includes a heart rate signal, respiration signal, pressure signal, or activity signal, and exercise is detected from a rise in the heart rate signal, respiration signal, pressure signal, or activity signal.

An example ("Example 42") subject matter (e.g., system, device, or method) a glucose sensor configured to generate a first signal representative of glucose concentration in a host, where the sensor includes a temperature sensor configured to generate a second signal representative of temperature, and a processor to evaluate the second signal based upon a third signal, and generate a temperature-compensated glucose concentration level based at least in part on the first signal and the evaluation of the second signal.

In Example 43, the subject matter of Example 42 may be configured such that the processor evaluates the second signal by corroborating a detected temperature or temperature change using the third signal.

In Example 44, the subject matter of Example 42 or 43 may be configured such that the processor determines a condition based upon the third signal and corroborates the detected temperature or temperature change based upon the condition.

In Example 45, the subject matter of any one or any combination of Examples 42-44 may be configured such that the condition is a location, an ambient environment, an activity state, or a physiologic condition.

In Example 46, the subject matter of any one or any combination of Examples 42-45 may be configured such that the processor suspends temperature compensation based at least in part on the third signal.

In Example 47, the subject matter of any one or any combination of Examples 42-46 may be configured such that the processor detects exercise based at least in part on the third signal.

In Example 48, the subject matter of Example 47 may be configured such that, responsive to detecting exercise, the processor suspends temperature compensation despite a drop in temperature indicated by the second signal may be configured such that the processor avoids an incorrect temperature compensation when a host exercises in a cool (e.g., cold outdoor or convectively cooled) environment.

In Example 49, the subject matter of any one or any combination of Examples 42-48 may be configured such that the processor specifies a temperature compensation model based at least in part on the third signal.

In Example 50, the subject matter of any one or any combination of Examples 42-49 may further include a third sensor, the third sensor generating the third signal.

In Example 51, the subject matter of any one or any combination of Examples 42-50 may be configured such that the third signal includes location information, and the processor evaluates the second signal based at least in part on the location information.

In Example 52, the subject matter of any one or any combination of Examples 42-51 may be configured such that the third signal includes activity information, and the processor evaluates the second signal based at least in part upon the activity information.

In Example 53, the subject matter of any one or any combination of Examples 42-52 may be configured such that the temperature-compensated glucose sensor system includes a wearable continuous glucose monitor that includes the glucose sensor and the temperature sensor.

In Example 54, the subject matter of any one or any combination of Examples 42-53 may be configured such that the temperature-compensated glucose sensor system includes an activity sensor and the third signal includes activity information from the activity sensor.

In Example 55, the subject matter of any one or any combination of Examples 42-54 may be configured such that the third signal includes a heart rate, a respiration rate, or a pressure of the host.

In Example 56, the subject matter of any one or any combination of Examples 42-55 may be configured such that the processor detects exercise based upon a change in the heart rate, respiration rate or pressure.

In Example 57, the subject matter of any one or any combination of Examples 42-56 may be configured such that the processor corroborates an elevated body temperature indicated by the second signal based at least in part on the detection of exercise.

In Example 58, the subject matter of any one or any combination of Examples 42-56 may be configured such that the processor decreases, tapers, caps, or suspends temperature compensation in response to detection of exercise.

In Example 59, the subject matter of any one or any combination of Examples 42-58 may be configured such that the third signal includes a signal from an optical sensor configured to detect blood parameter of a host.

In Example 60, the subject matter of Example 59 may further include the optical sensor, the optical sensor including a light source and a light detector configured to detect a blood flow velocity or a number of red blood cells in an area of the host under the optical sensor.

An example ("Example 61") of subject matter (e.g., a system, device or method) may include temperature-compensating a continuous glucose sensor by determining a pattern from temperature data, receiving a glucose signal from a continuous glucose sensor, the glucose signal indicative of a glucose concentration level, and determining a temperature-compensated glucose concentration level based at least in part on the sensor glucose signal and the pattern.

In Example 62, the subject matter of Example 61 may be configured such that determining a pattern includes determining a pattern of temperature variations, and the method includes compensating the glucose concentration level according to the pattern.

In Example 63, the subject matter of Example 61 or 62 may further include receiving a temperature parameter, comparing the temperature parameter to the pattern, and determining the temperature-compensated glucose concentration level based at least in part on the comparison.

In Example 64, the subject matter of Example 63 may be configured such that the pattern includes a temperature pattern correlated to a physiological cycle.

In Example 65, the subject matter of Example 63 or 64 may be configured such that the method includes determining whether the temperature parameter is reliable based on the comparison to the pattern and using the temperature parameter to temperature-compensate the glucose concentration level when the temperature parameter is determined to be reliable.

In Example 66, the subject matter of any one or any combination of Examples 63-65 may be configured such that the method includes determining a degree of compensation based at least in part on the comparison of the temperature parameter to the pattern. For example, the degree of compensation may be based on defined ranges or confidence intervals.

In Example 67, the subject matter of any one or any combination of Examples 61-66 may be configured such that determining a pattern includes determining a state, and determining a temperature-compensated glucose concentration level is based at least in part on the determined state.

In Example 68, the subject matter of Example 67 may be configured such that determining a state includes applying a temperature parameter to a state model.

In Example 69, the subject matter of Example 67 or 68 may be configured such that determining a state includes applying one or more of a glucose concentration level, carbohydrate sensitivity, time, activity, heart rate, respiration rate, posture, insulin delivery, meal time, or meal size to a state model.

In Example 70, the subject matter of any one or any combination of Examples 67-69 may be configured such that determining a state includes determining an exercise state, the method includes adjusting a temperature compensation based model upon the exercise state.

An example ("Example 71") of subject matter (e.g., a system, device or method) may include a glucose sensor circuit configured to generate a glucose signal representative of a glucose concentration level, a temperature sensor circuit configured to generate a temperature signal indicative of a temperature parameter, and a processor to receive the glucose signal and the temperature signal, and determine a temperature-compensated glucose concentration level based at least in part on the glucose signal and a pattern determined from the temperature signal.

In Example 72, the subject matter of Example 71 may be configured such that the processor determines a temperature parameter based on the temperature signal, compares the temperature parameter to the pattern, and determines a temperature-compensated glucose concentration level based at least in part on the comparison.

In Example 73, the subject matter of Example 71 or 72 may be configured such that the processor determines whether the temperature parameter is reliable based on the comparison to the pattern, and uses the temperature parameter to temperature-compensate the glucose concentration level when the temperature parameter is determined to be reliable.

In Example 74, the subject matter of Example 72 or 73 may be configured such that the processor determines a degree of compensation based at least in part on the comparison of the temperature parameter to the pattern.

In Example 75, the subject matter of any one or any combination of Examples 71-74 may be configured such that the pattern includes a state model and the processor determines the temperature-compensated glucose concentration level based at least in part by applying a temperature parameter to the state model.

In Example 76, the subject matter of Example 75 may be configured such that the processor determines the temperature-compensated glucose concentration level by additionally applying one or more of a glucose concentration level, carbohydrate sensitivity, time, activity, heart rate, respiration rate, posture, insulin delivery, meal time, or meal size to the state model.

In Example 77, the subject matter of Example 75 or 76 may be configured such that the processor determines an exercise state and adjusts a temperature compensation model based at least in part on the exercise state.

In Example 78, the subject matter of any one or any combination of Examples 71-77 may further include a memory circuit including executable instructions to determine a pattern from the temperature signal and to determine a temperature-compensated glucose concentration level based on the pattern, the processor being configured to retrieve the instructions from memory and execute the instructions.

In Example 79, the subject matter of any one or any combination of Examples 71-78 may be configured such that the processor receives information about the pattern from the remote system via the communication circuit.

In Example 80, the subject matter of Example 79 may be configured such that the remote system receives temperature parameter information based on the temperature signal and determines a pattern from the temperature parameter information.

An example ("Example 81") of subject matter (e.g. a method, system, or device) may include determining a first value from a first signal indicative of a temperature parameter of a component of a continuous glucose sensor system, receiving a glucose sensor signal indicative of a glucose concentration level, comparing the first value to a reference value, and determining a temperature-compensated glucose level based on the glucose sensor signal and the comparison of the first signal to the reference value.

In Example 82, the subject matter of Example 81 may be configured such that the method includes determining a temperature difference from a reference state based upon a variation of the first value from the reference value without calibrating a temperature for the reference value.

In Example 83, the subject matter of Example 81 or 82 may further include determining the reference value from the first signal.

In Example 84, the subject matter of Example 83 may be configured such that the continuous glucose sensor system includes a glucose sensor that is insertable into a host and the reference value is determined during a specified time period after insertion of the glucose sensor in a host.

In Example 85, the subject matter of Example 83 or 84 may be configured such that the continuous glucose sensor system includes a glucose sensor that is insertable into a host and the reference value is determined during a specified time period after activation of the glucose sensor.

In Example 86, the subject matter of any one or any combination of Examples 83-85 may be configured such that the reference value is determined during a manufacturing process.

In Example 87, the subject matter of any one or any combination of Examples 83-86 may be configured such that the method includes determining the reference value during a first time period and determining the first value during a second time period, the second time period occurring after the first time period. The reference value may, for example, be a long-term average and the first value may be a short term average.

In Example 88, the subject matter of Example 87 may further include updating the reference value based on one or more temperature signal values obtained in a third time period after the second time period.

In Example 89, the subject matter of any one or any combination of Examples 83-88 may be configured such that determining the reference value includes determining an average of a plurality of sample values obtained from the first signal.

In Example 90, the subject matter of any one or any combination of Examples 81-89 may be configured such that the temperature-compensated glucose level is determined based at least in part on a temperature-dependent sensitivity value that varies based on a deviation of the first value from the reference value.

An Example ("Example 91") of subject matter (e.g., a system, device, or method) may include a glucose sensor circuit configured to generate a glucose signal representative of a glucose concentration level, a temperature sensor circuit configured to generate a first signal indicative of a temperature parameter, and a processor and determine a temperature-compensated glucose level based on the glucose signal and a deviation of the first signal from a reference value.

In Example 92, the subject matter of Example 91 may be configured such that the processor determines a deviation of the first signal from the reference value without determining a temperature that corresponds to the reference value.

In Example 93, the subject matter of Example 91 or 92 may be configured such that the processor determines the reference value based on the first signal.

In Example 94, the subject matter of Example 93 may be configured such that the processor determines the reference value based on a plurality of sample values obtained from the first signal during a first time period.

In Example 95, the subject matter of Example 93 or 94 may be configured such that the processor determines the reference value based on a plurality of sample values obtained from the first signal during a specified period of time after activation or insertion of a glucose sensor.

In Example 96, the subject matter of any one or any combination of Examples 93-95 may be configured such that the processor recurrently updates the reference value.

In Example 97, the subject matter of any one or any combination of Examples 91-96 may be configured such that the processor determines the reference value as an average of a plurality of sample values obtained from the first signal during a specified time period.

In Example 98, the subject matter of any one or any combination of Examples 91-97 may be configured such that the processor determines the temperature-compensated glucose level based on the glucose signal and a temperature-dependent sensitivity value that varies based on the deviation from the reference value.

In Example 99, the subject matter of any one or any combination of Examples 91-98 may be configured such that the processor determines the temperature-compensated glucose concentration level based on a model that may be configured such that a glucose sensor value determined from the glucose signal and a sample value based on the first signal are applied to the model.

In Example 100, the subject matter of any one or any combination of Examples 91-100 may further include a memory circuit and stored executable instructions on the memory circuit to determine the temperature-compensated glucose concentration level based on the glucose signal and a deviation of the first signal from the reference value.

An example ("Example 101) of subject matter (e.g., method, system, or device) may include receiving a glucose signal indicative of a glucose concentration level, receiving a temperature signal indicative of a temperature parameter, detecting a condition, and determining a temperature-compensated glucose concentration level based at least in part on the glucose signal, the temperature signal, and the detected condition.

In Example 102, the subject matter of Example 101 may be configured such that the condition includes a high rate of change in the glucose signal, wherein temperature compensation is reduced or suspended during a period during which the glucose signal is undergoing a high rate of change.

In Example 103, the subject matter of Example 101 or 102 may be configured such that the condition includes a sudden change in the temperature signal.

In Example 104, the subject matter of Example 103 may be configured such that temperature compensation is reduced or suspended in response to detection of the sudden change in temperature.

In Example 105, the subject matter of Example 103 or 104 may be configured such that determining a temperature-compensated glucose concentration level includes using a previous temperature signal value in lieu of a temperature signal value that is associated with a sudden change in temperature.

In Example 106, the subject matter of any one or any combination of Examples 103-105 may be configured such that determining a temperature-compensated glucose concentration level includes determining an extrapolated temperature signal value based on prior temperature signal values and using the extrapolated temperature signal value in lieu of a temperature signal value that associated with a sudden change in temperature.

In Example 107, the subject matter of Example 106 may be configured such that a delay model is invoked in response to detection of a sudden change in temperature, the delay model specifying a delay period for use in determining the temperature-compensated glucose level.

In Example 108, the subject matter of any one or any combination of Examples 101-107 may be configured such that the condition is the presence of a radiant heat on the continuous glucose monitoring system.

In Example 109, the subject matter of any one or any combination of Examples 101-108 may be configured such that the condition is a fever, wherein temperature compensation is reduced or suspended responsive to detection of the fever.

In Example 110, the subject matter of Example 109 may be configured such that the condition includes exercise.

In Example 111, the subject matter of Example 110 may be configured such that the method includes decreasing, tapering, capping, or suspending temperature compensation when exercise is detected.

In Example 112, the subject matter of any one or any combination of Examples 101-111 may be configured such that the method includes using a linear model to determine the temperature-compensated glucose concentration level.

In Example 113, the subject matter of Example 112 may further include receiving a blood glucose calibration value, wherein a temperature compensation gain and offset is updated when a blood glucose calibration value is received.

In Example 114, the subject matter of any one or any combination of Examples 101-113 may be configured such that the method includes using a time series model to determine the temperature-compensated glucose concentration level.

In Example 115, the subject matter of any one or any combination of Examples 101-114 may be configured such that the method includes using a partial differential equation to determine temperature-compensated glucose concentration level.

In Example 116, the subject matter of any one or any combination of Examples 101-115 may be configured such that the method includes using a probabilistic model to determine the temperature-compensated glucose concentration level.

In Example 117, the subject matter of any one or any combination of Examples 101-116 may be configured such that the method includes using a state model to determine the temperature-compensated glucose concentration level.

In Example 118, the subject matter of any one or any combination of Examples 101-117 may be configured such that the condition includes a body mass index (BMI) value.

In Example 119, the subject matter of any one or any combination of Examples 101-118 may be configured such that the method includes determining a long-term average using the temperature signal, wherein the temperature-compensated glucose concentration level is determined using the long-term average.

In Example 120, the subject matter of any one or any combination of Examples 101-119 may be configured such that the glucose signal indicative of a condition is received from a continuous glucose sensor, and the condition is compression on a continuous glucose sensor.

In Example 121, the subject matter of Example 120 may be configured such that the compression is detected based at least in part upon a rapid drop in the glucose signal.

In Example 122, the subject matter of Example 120 or 121 may be configured such that the condition is compression during sleep.

In Example 123, the subject matter of any one or any combination of Examples 101-122 may be configured such that the condition is sleep.

In Example 124, the subject matter of Example 123, where sleep is detected using one or more of temperature, posture, activity, and heart rate, and the method includes applying a specified glucose alert trigger based upon the detected sleep.

In Example 125, the subject matter of any one or any combination of Examples 101-124 may further include delivering an insulin therapy, wherein the therapy is determined at least in part based upon the temperature-compensated glucose level.

An Example, ("Example 126") of subject matter (e.g., a system, device, or method) may include a glucose sensor circuit configured to generate a glucose signal representative of a glucose concentration level, a temperature sensor circuit configured to generate a temperature signal indicative of a temperature parameter, and a processor configured to determine a compensated glucose concentration level based on the glucose signal, the temperature signal, and a detected condition.

In Example 127, the subject matter of Example 126 may be configured such that the condition includes a high rate of change in the glucose signal, and the processor reduces, suspends, tapers, or caps temperature compensation during a period of high rate of change of the glucose signal.

In Example 128, the subject matter of Example 126 or 127 may be configured such that the condition includes a sudden change in the temperature signal, and may be configured such that the processor reduces, suspends, tapers, or caps temperature compensation in response to detection of the sudden change in temperature.

In Example 129, the subject matter of any one or any combination of Examples 126-128 may be configured such that the condition includes exercise, and may be configured such that the processor decreases, tapers, caps, or suspends temperature compensation when exercise is detected.

In Example 130, the subject matter of any one or any combination of Examples 126-129 may further include a second temperature sensor circuit configured to detect radiant heat on the continuous glucose monitoring system, and wherein the detected condition includes radiant heat detected by the second temperature sensor circuit.

An example ("Example 131") of subject matter (e.g., device, system, or method) may include an elongated portion having a distal end configured for in-vivo insertion into a host and a proximal end configured to operatively couple to a circuit, and a temperature sensor at the proximal end of the elongated portion.

In Example 132, the subject matter of Example 131 may be configured such that the temperature sensor includes a thermistor.

In Example 133, the subject matter of Example 131 or 132 may be configured such that the temperature sensor includes a temperature variable resistive coating.

In Example 134, the subject matter of any one or any combination of Examples 131-133 may be configured such that the temperature sensor includes a thermocouple.

In Example 135, the subject matter Example 134 may be configured such that the elongated portion includes a first wire extending from the proximal end to the distal end, and the thermocouple includes the first wire and a second wire joined to the first wire to form the thermocouple.

In Example 136, the subject matter of Example 135 may be configured such that the first wire is tantalum or a tantalum alloy and the second wire is platinum or a platinum alloy.

In Example 137, the subject matter of Example 135 or 136 may further include a transmitter coupled to the glucose sensor, a first electrical contact on the transmitter being coupled to the first wire and a second electrical contact on the transmitter being coupled to the second wire.

An example ("Example 138") of subject matter (e.g., a method, system, or device) may include receiving a calibration value for a temperature signal, receiving from a temperature sensor a temperature signal indicative of a temperature parameter, receiving from a continuous glucose sensor a glucose signal indicative of a glucose concentration level, and determining a temperature-compensated glucose concentration level based at least in part on the glucose signal, the temperature signal, and the calibration value.

In Example 139, the subject matter of Example 138 may be configured such that receiving a calibration value for the temperature signal includes obtaining the calibration during a manufacturing step having a known temperature.

In Example 140, the subject matter of Example 138 or 139 may be configured such that receiving a calibration value for the temperature signal includes obtaining a temperature during a specified period of time after insertion of the continuous glucose sensor in a host.

An example ("Example 141") of subject matter (e.g., method, system, or device) may include receiving a temperature signal indicative of a temperature of a component of a continuous glucose sensor on a host, and determining an anatomical location of the continuous glucose sensor on the host based at least in part on the received temperature signal.

In Example 142, the subject matter of Example 141 may be configured such that the anatomical location is determined at least in part based on a sensed temperature.

In Example 143, the subject matter of Example 141 or 142 may be configured such that the anatomical location is determined based at least in part on a variability of the temperature signal.

An example ("Example 144") of subject matter (e.g., method, system, or device) may include receiving from a temperature sensor on a continuous glucose monitor a temperature signal indicative of a temperature parameter, and determining from the temperature signal that the continuous glucose monitor was restarted.

In Example 145, the subject matter of Example 144 may be configured such that determining from the temperature signal that the continuous glucose monitor was restarted includes comparing a first temperature signal value prior to a sensor initiation to a second temperature signal value after sensor initiation, and declaring that the continuous glucose monitor was restarted when comparison satisfies a similarity condition.

In Example 146, the subject matter of Example 144 or 145 may be configured such that the similarity condition is a temperature range.

An example ("Example 147") of subject matter (e.g., system, device, or method) may include a glucose sensor circuit configured to generate a glucose signal representative of a glucose concentration level, a temperature sensor circuit configured to generate a temperature signal indicative of a temperature parameter, a heat deflector configured to deflect heat from the temperature sensor circuit, and a processor configured to determine a compensated glucose concentration level based at least in part on the glucose signal and the temperature signal.

An example ("Example 148") of subject matter (e.g., system, device, or method) may include a glucose sensor circuit configured to generate a glucose signal representative of a glucose concentration level of a host, a first temperature sensor circuit configured to generate a first temperature signal indicative of a first temperature parameter proximate the host, a second temperature sensor circuit configured to generate a second temperature signal indicative of a second temperature parameter, and a processor configured to determine a compensated glucose concentration level based at least in part on the glucose signal, the first temperature signal, and the second temperature signal.

In Example 149, the subject matter of Example 148 may be configured such that the processor determines the compensated glucose concentration level based in part on a temperature gradient between the first temperature sensor circuit and the second temperature sensor circuit.

In Example 150, the subject matter of Example 148 or 149 may be configured such that the processor determines the compensated glucose concentration level based in part on an estimate of heat flux between the first temperature sensor circuit and the second temperature sensor circuit.

In Example 151, the subject matter of any one or any combination of Examples 148-150 may be configured such that the second temperature circuit is configured to generate a temperature signal indicative of an ambient temperature.

In Example 152, the subject matter of any one or any combination of Examples 148-151 may be configured such that the processor is configured to generate a temperature signal indicative of a temperature of a transmitter coupled to the glucose sensor circuit.

An example ("Example 153") of subject matter (e.g., method, device, or system) may include receiving from a glucose sensor a glucose signal representative of a glucose concentration level of a host, receiving a first temperature signal indicative of a first temperature parameter proximate the host or the glucose sensor, receiving a second temperature signal indicative of a second temperature parameter, and determining a compensated glucose concentration level based at least in part on the glucose signal, the first temperature signal, and the second temperature signal.

In Example 154, the subject matter of Example 153 may be configured such that the first temperature signal is received from a first temperature sensor coupled to the glucose sensor, the second temperature signal is received from a second temperature sensor coupled to the glucose sensor.

In Example 155, the subject matter of Example 154 may be configured such that the compensated glucose concentration level is determined based at least in part on a temperature gradient between the first temperature sensor and the second temperature sensor.

In Example 156, the subject matter of Example 154 or 155 may be configured such that the compensated glucose concentration level is determined based at least in part on a heat flux between the first temperature sensor and the second temperature sensor.

In Example 157, the subject matter of any one or any combination of Examples 154-156 may further include detecting a rise in the first temperature signal and a drop in the second temperature signal, and adjusting a temperature compensation model based upon the detected rise and drop.

In Example 158, the subject matter of Example 157 may be configured such that the method includes detecting exercise (e.g., outdoor exercise or convectively cooled exercise) based at least in part on the detected rise and drop and adjusting or applying a temperature compensation model based upon the detection of exercise.

In Example 159, the subject matter of any one or any combination of Examples 154-158 may further include determining that a temperature change is due to radiant heat or ambient heat based at least in part on the second temperature signal, and adjusting or applying a temperature compensation model based upon the determination.

An example ("Example 160) of subject matter (e.g., method, system, or device) may determine a glucose concentration level by receiving a temperature sensor signal, receiving a glucose sensor signal, applying the temperature sensor signal and glucose sensor signal to a model, and receiving an output from the model relating to the glucose concentration level, where the model compensates for a plurality of temperature-dependent effects on the glucose sensor signal.

In Example 161, the subject matter of Example 161 may be configured such that the output is a compensated glucose concentration level.

In Example 162, the subject matter of Example 161 may further include delivering a therapy based upon the compensated glucose concentration value.

In Example 163, the subject matter of Example 161 may be configured such that the model compensates for two or more of sensor sensitivity, a local glucose level, a compartment bias, and a nonenzyme bias. In some examples, the model may compensate for three or more of sensor sensitivity, a local glucose level, a compartment bias, and a nonenzyme bias. In some examples, the model may account for additional temperature-dependent factors in addition to sensor sensitivity, a local glucose level, a compartment bias, and a nonenzyme bias.

An example (Example 164) of subject matter (e.g., method, system, or device) may include determining an analyte concentration level by determining a first value indicative of a conductance of a sensor component, determining a second value indicative of a conductance of the sensor component, receiving a signal representative of an analyte concentration of a host, and determining a compensated analyte concentration level based at least in part on a comparison of the second value and the first value. The first value and second value may, for example, be an electrical conductance or an electrical resistance or an electrical impedance.

In Example 165, the subject matter of Example 164, may be configured such that determining a first value includes determining an average conductance.

In Example 166, the subject matter of Example 164 or Example 165 may optional include determining a first estimated subcutaneous temperature that is time-correlated with the first value, and determining a second estimate subcutaneous temperature that is time-correlated with the second value, wherein the second estimated subcutaneous temperature is determined based at least in part on a comparison of the second value with the first value.

In Example 167, the subject matter of Example 166 may optional include determining a third estimated subcutaneous temperature that is time-correlated with the second value, determining whether a condition is satisfied based upon a comparison of the third estimated subcutaneous temperature and the second estimated subcutaneous temperature, and declaring an error or triggering a reset responsive to satisfaction of the condition.

In Example 168, the subject matter of Example 167 may optional include triggering a reset, wherein triggering a reset includes determining subsequent estimated subcutaneous temperatures based upon the third estimated temperature and the second value or based upon a third conductance value and a fourth estimated subcutaneous temperature that is time-correlated with the third conductance value.

In Example 169, the subject matter of any one or any combination of Examples 164-168 may optionally include compensating for drift in the conductance value.

In Example 170, the subject matter of any one or any combination of Examples 164-169 may optionally be configured such that compensating for drift includes applying a filter.

An Example (Example 171) of subject matter (e.g., method, system, or device) may include determining a first value indicative of a conductance of a sensor component at a first time, determining a second value indicative of a conductance of the sensor component at a later time, and determining an estimated subcutaneous temperature based at least in part on a comparison of the second value and the first value.

An Example (Example 172) of subject matter (e.g., method, system, or device) may include accessing, by the analyte sensor system, first data from a system temperature sensor of the analyte sensor system; applying the first data to a trained temperature compensation model, the trained temperature compensation model for generating a compensated temperature value; and determining an analyte concentration value based at least in part on the compensated temperature value.

In Example 173, the subject matter of Example 172 may be configured such that the first data comprises at least one of an uncompensated temperature value or raw temperature sensor data from the system temperature sensor.

In Example 174, the subject matter of any one or more of Examples 172-173 may be configured such that the trained temperature compensation model returns a first temperature sensor parameter in response to the first data and may further comprise generating the compensated temperature value based at least in part on the first temperature sensor parameter.

In Example 175, the subject matter of any one or more of Examples 172-174 may be configured such that the trained temperature compensation model returns a system temperature sensor offset and a system temperature sensor slope and further comprise receiving raw sensor data from the system temperature sensor; and generating the compensated temperature value based at least in part on the raw sensor data, the system temperature sensor offset and the system temperature sensor slope.

An Example (Example 176) of subject matter (e.g., method, system, or device) may include an analyte sensor; a system temperature sensor; and a control circuit. The control circuit may be configured to perform operations comprising: accessing first data from a system temperature sensor of the analyte sensor system; applying the first data to a trained temperature compensation model, the trained temperature compensation model for generating a compensated temperature value; and determining an analyte concentration value based at least in part on the compensated temperature value.

In Example 177, the subject matter of Example 176 may be configured such that the first data comprises at least one of an uncompensated temperature value or raw temperature sensor data from the system temperature sensor.

In Example 178, the subject matter of any one or more of Examples 176-177 may be configured such that the trained temperature compensation model returns a first temperature sensor parameter in response to the first data and may further comprise generating the compensated temperature value based at least in part on the first temperature sensor parameter.

In Example 179, the subject matter of any one or more of Examples 176-178 may be configured such that the trained temperature compensation model returns a system temperature sensor offset and a system temperature sensor slope, and may further comprise receiving raw sensor data from the system temperature sensor; and generating the compensated temperature value based at least in part on the raw sensor data, the system temperature sensor offset and the system temperature sensor slope.

In Example 180, the subject matter of any one or more of Examples 176-179 may further include an application specific integrated circuit (ASIC) comprising the system temperature sensor.

An Example (Example 181) of subject matter (e.g., method, system, or device) may include determining a temperature-compensated glucose concentration level. The determining may include receiving a glucose sensor signal; receiving a temperature parameter signal; detecting an exercise state based at least in part on the glucose sensor signal or the temperature parameter signal; and modifying a temperature compensation applied to the glucose sensor signal.

In Example 182, the subject matter of Example 181 may includes determining that a noise floor of the glucose sensor signal is greater than a first threshold.

In Example 183, the subject matter of any one or more of Examples 181-182 may include determining that a noise floor of the temperature parameter signal is greater than a second threshold.

In Example 184, the subject matter of any one or more of Examples 181-183 may include determining that a noise floor of the glucose sensor signal is greater than a first threshold; and determining that a noise floor of the temperature parameter signal is greater than a second threshold.

In Example 185, the subject matter of any one or more of Examples 181-184 may be configured such that modifying the temperature compensation comprises: applying an exercise model to the temperature parameter signal to generate an evaluated temperature parameter signal; and generating a temperature compensated glucose concentration value using the evaluated temperature parameter.

In Example 186, the subject matter of any one or more of Examples 181-185 may be configured such that detecting the exercise state comprises determining that a distribution of rates of change of the temperature parameter signal meets a classifier.

In Example 187, the subject matter of any one or more of Examples 181-186 may be configured such that detecting the exercise state comprises determining that a distribution of rates of change of the temperature parameter signal is less than a threshold.

An example (Example 188) of subject matter (e.g., method, system, or device) may include a temperature-compensated glucose sensor system comprising a glucose sensor configured to generate a first signal representative of glucose concentration in a host; a temperature sensor configured to generate a second signal representative of temperature; and a processor. The processor may be programmed to perform operations comprising: detecting an exercise state based at least in part on the first signal or the second signal; and modifying a temperature compensation applied to the first signal.

In Example 189, the subject matter of Example 188 may be configured such that the operations further comprise determining that a noise floor of the first signal is greater than a first threshold.

In Example 190, the subject matter of any one or more of Examples 188-189 may be configured such that the operations further comprise determining that a noise floor of the second signal is greater than a second threshold.

In Example 191, the subject matter of any one or more of Examples 188-190 may be configured such that the operations further comprise: determining that a noise floor of the first signal is greater than a first threshold; and determining that a noise floor of the second signal is greater than a second threshold.

In Example 192, the subject matter of any one or more of Examples 188-191 may be configured such that modifying the temperature compensation comprises: applying an exercise model to the second signal to generate an evaluated second signal; and generating a temperature compensated glucose concentration value using the evaluated second signal.

In Example 193, the subject matter of any one or more of Examples 188-192 may be configured such that detecting the exercise state comprises determining that a distribution of rates of change of the second signal meets a classifier.

In Example 194, the subject matter of any one or more of Examples 188-193 may be configured such that detecting the exercise state comprises determining that a distribution of rates of change of the second signal is less than a threshold.

An Example ("Example 195") of subject matter (e.g., a method, system, or device) may include processor-implemented method of measuring a temperature at an analyte sensor system. The method may comprise, during a first sensor session, accessing a record of periodic temperatures stored at the analyte sensor system; determining a peak temperature from the record of periodic temperatures; and performing a responsive action based on the peak temperature.

In Example 196, the subject matter of Example 195 may include determining that the peak temperature exceeds a peak temperature threshold, wherein the responsive action comprises aborting the first sensor session.

In Example 197, the subject matter of any one or more of Examples 195-196 may include determining an initial sensor session parameter based at least in part on the peak temperature; receiving raw sensor data from an analyte sensor of the analyte sensor system; and generating an analyte concentration value using the initial session parameter and the raw sensor data.

In Example 198, the subject matter of any one or more of Examples 195-197 may be configured such that the initial sensor session parameter comprises a sensitivity or a baseline.

In Example 199, the subject matter of any one or more of Examples 195-198 may include, prior to the first sensor session, measuring a first temperature at the analyte sensor system; writing the first temperature to the record of periodic temperatures; waiting one period; and measuring a second temperature at the analyte sensor system.

An example ("Example 200") of subject matter may include a temperature-compensated analyte sensor system. The temperature-compensated analyte sensor system may comprise an analyte sensor configured to generate a first signal representative of analyte concentration in a host; a temperature sensor configured to generate a second signal representative of temperature; and a processor. The processor may be programmed to perform operations comprising: during a first sensor session, accessing a record of periodic temperatures stored at the analyte sensor system; determining a peak temperature from the record of periodic temperatures; and performing a responsive action based on the peak temperature.

In Example 201, the subject matter of Example 200 may be configured such that the operations further comprise determining that the peak temperature exceeds a peak temperature threshold, wherein the responsive action comprises aborting the first sensor session.

In Example 202, the subject matter of any one or more of Examples 200-201 may be configured such that the operations further comprise determining an initial sensor session parameter based at least in part on the peak temperature; receiving raw sensor data from an analyte sensor of the analyte sensor system; and generating an analyte concentration value using the initial session parameter and the raw sensor data.

In Example 203, the subject matter of any one or more of Examples 200-202 may be configured such that the initial sensor session parameter comprises a sensitivity or a baseline.

In Example 204, the subject matter of any one or more of Examples 200-203 may be configured such that the operations further comprise, prior to the first sensor session, measuring a first temperature at the analyte sensor system; writing the first temperature to the record of periodic temperatures; waiting one period; and measuring a second temperature at the analyte sensor system.

An example ("Example 205") of subject matter (e.g., a method, system, or device) may include a temperature sensing analyte sensor system. The temperature sensing analyte sensor system may comprise: a diode; and an electronics circuit; a sample-and-hold circuit, and a dual slope integrating analog-to-digital converter (ADC). The electronics circuit may be configured to perform operations comprising: applying the diode with a first current for a first period, wherein a voltage drop across the diode has a first voltage value when the first current is provided to the diode; and applying the diode with a second current different than the first current for a second period after the first period, wherein the voltage drop across the diode has a second voltage value when the second current is provided to the diode. The sample-and-hold circuit may be configured to receive the first voltage value when the first voltage is applied to the diode and generate an output indicating the first voltage. The dual slope integrating analog-to-digital converter (ADC) may comprise a first input coupled to receive the first voltage value from the output of the sample-and-hold circuit and a second input coupled to receive the voltage drop across the diode. A time for an output of the dual slope integrating ADC to decay from the first voltage value to the second voltage value may be proportional to a temperature at the diode.

In Example 206, the subject matter of Example 205 may further comprise a comparator coupled to compare the output of the sample and hold circuit to the output of the dual slope integrating analog-to-digital circuit.

In Example 207, the subject matter of any one or more of Examples 205-206 may further comprise a digital counter. The operations may further comprise starting the digital counter at a peak of the output of the dual slope integrating ADC; and determining a value of the digital counter upon a change in the output of the comparator.

In Example 208, the subject matter of any one or more of Examples 205-207 may be configured such that the value of the digital counter indicates time for an output of the dual slope integrating ADC to decay from the first voltage value to the second voltage value is proportional to a temperature at the diode.

In Example 209, the subject matter of any one or more of Examples 205-208 may further comprise an AND circuit configured to generate a logical and between an output of the comparator and a clock signal, wherein the clock signal is low when the first current is applied to the diode.

In Example 210, the subject matter of any one or more of Examples 205-209 may be configures such that the diode comprises a diode connected transistor.

In Example 211, the subject matter of any one or more of Examples 205-210 may be configured such that an analyte sensor of the analyte sensor is inserted into a skin of a host, and the diode is positioned proximate the skin of a host.

In Example 212, the subject matter of any one or more of Examples 205-211 may further comprise a first constant current source to provide the first current; and a second pulsed current source, wherein the second current comprises a sum of the first current and a current provided by the second pulsed current source when the second pulsed current source is on.

An example ("Example 213") of subject matter (e.g., a method, system, or device) may include applying a first current to a diode for a first period, wherein a voltage drop across the diode has a first voltage value when the first current is provided to the diode; applying a second current different than the first current to the diode after the first period, wherein the voltage drop across the diode has a second voltage value when the second current is provided to the diode; and providing a first voltage value and the second voltage value to a dual slope integrating analog-to-digital converter (ADC), wherein a time for an output of the dual slope integrating ADC to decay from the first voltage value to the second voltage value is proportional to a temperature at the diode.

In Example 214, the subject matter Example 213 may include comparing the output of the sample and hold circuit to the output of the dual slope integrating analog-to-digital circuit to generate a comparator output.

In Example 215, the subject matter of any one or more of Examples 213-214 may include starting a digital counter at a peak of the output of the dual slope integrating ADC; and determining a value of the digital counter upon a change in the comparator output.

In Example 216, the subject matter of any one or more of Examples 213-215 may be configured such that the value of the digital counter indicates time for an output of the dual slope integrating ADC to decay from the first voltage value to the second voltage value is proportional to a temperature at the diode.

In Example 217, the subject matter of any one or more of Examples 213-216 may include an AND circuit configured to generate a logical and between an output of the comparator and a clock signal. The clock signal may be low when the first current is applied to the diode.

In Example 218, the subject matter of any one or more of Examples 213-217 may be configured such that the diode comprises a diode connected transistor.

In Example 219, the subject matter of any one or more of Examples 213-218 may be configured such that an analyte sensor of the analyte sensor is inserted into a skin of a host, and wherein the diode is positioned proximate the skin of a host.

An example ("Example 220") of subject matter (e.g., a method, system, or device) may include a method of determining a glucose concentration level. The method may comprise receiving a temperature sensor signal; receiving a glucose sensor signal from a glucose sensor inserted at an insertion site at a host; and applying the temperature sensor signal and the glucose sensor signal to a model describing a difference between a glucose concentration at the insertion site and a blood glucose concentration at the host to generate a compensated blood glucose concentration for the host.

In Example 221, the subject matter of Example 220 may include determining a model time parameter based at least in part on the temperature sensor signal; and determining the compensated blood glucose concentration based at least in part on the model time parameter.

In Example 222, the subject matter of any one or more of Examples 220-221 may be configured such that the model time parameter applies to the glucose concentration at the insertion site and to the blood glucose concentration.

In Example 223, the subject matter of any one or more of Examples 220-222 may further comprise determining a glucose consumption describing the host. The compensated blood glucose concentration may be based at least in part on the glucose consumption.

In Example 224, the subject matter of any one or more of Examples 220-223, may further comprise determining the glucose consumption using a constant cell layer glucose concentration.

In Example 225, the subject matter of any one or more of Examples 220-224 may further comprise determining the glucose consumption using a variable cell layer glucose concentration.

In Example 226, the subject matter of any one or more of Examples 220-225 may include determining the glucose consumption using a linearly varying cell layer glucose concentration.

An example ("Example 227") of subject matter (e.g., a method, system, or device) may include a temperature-compensating glucose sensor system. The temperature-compensating glucose sensor system may comprise a glucose sensor; and sensor electronics. The sensor electronics may be configured to perform operations comprising: receiving a temperature sensor signal; receiving a glucose sensor signal from a glucose sensor inserted at an insertion site at a host; and applying the temperature sensor signal and the glucose sensor signal to a model describing a difference between a glucose concentration at the insertion site and a blood glucose concentration at the host to generate a compensated blood glucose concentration for the host.

In Example 228, the subject matter of Example 227 is configured such that the operations further comprise determining a model time parameter based at least in part on the temperature sensor signal; and determining the compensated blood glucose concentration based at least in part on the model time parameter.

In Example 229, the subject matter of any one or more of Examples 227-228 may be configured such that the model time parameter applies to the glucose concentration at the insertion site and to the blood glucose concentration.

In Example 230, the subject matter of any one or more of Examples 227-229 may be configured such that the operations further comprise determining a glucose consumption describing the host, wherein the compensated blood glucose concentration is based at least in part on the glucose consumption.

In Example 231, the subject matter of any one or more of Examples 227-230 may be configured such that the operations further comprise determining the glucose consumption using a constant cell layer glucose concentration.

In Example 232, the subject matter of any one or more of Examples 227-230 may be configured such that the operations further comprise determining the glucose consumption using a variable cell layer glucose concentration.

In Example 233 the subject matter of any one or more of Examples 227-231 may be configured such that the operations further comprise determining the glucose consumption using a linearly varying cell layer glucose concentration.

An example (e.g., "Example 172") of subject matter (e.g., a system or apparatus) may optionally combine any portion or combination of any portion of any one or more of Examples 1-171 to include "means for" performing any portion of any one or more of the functions or methods of Examples 1-171, or a "machine-readable medium" (e.g., massed, non-transitory, etc.) including instructions that, when performed by a machine, cause the machine to perform any portion of any one or more of the functions or methods of Examples 1-171.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
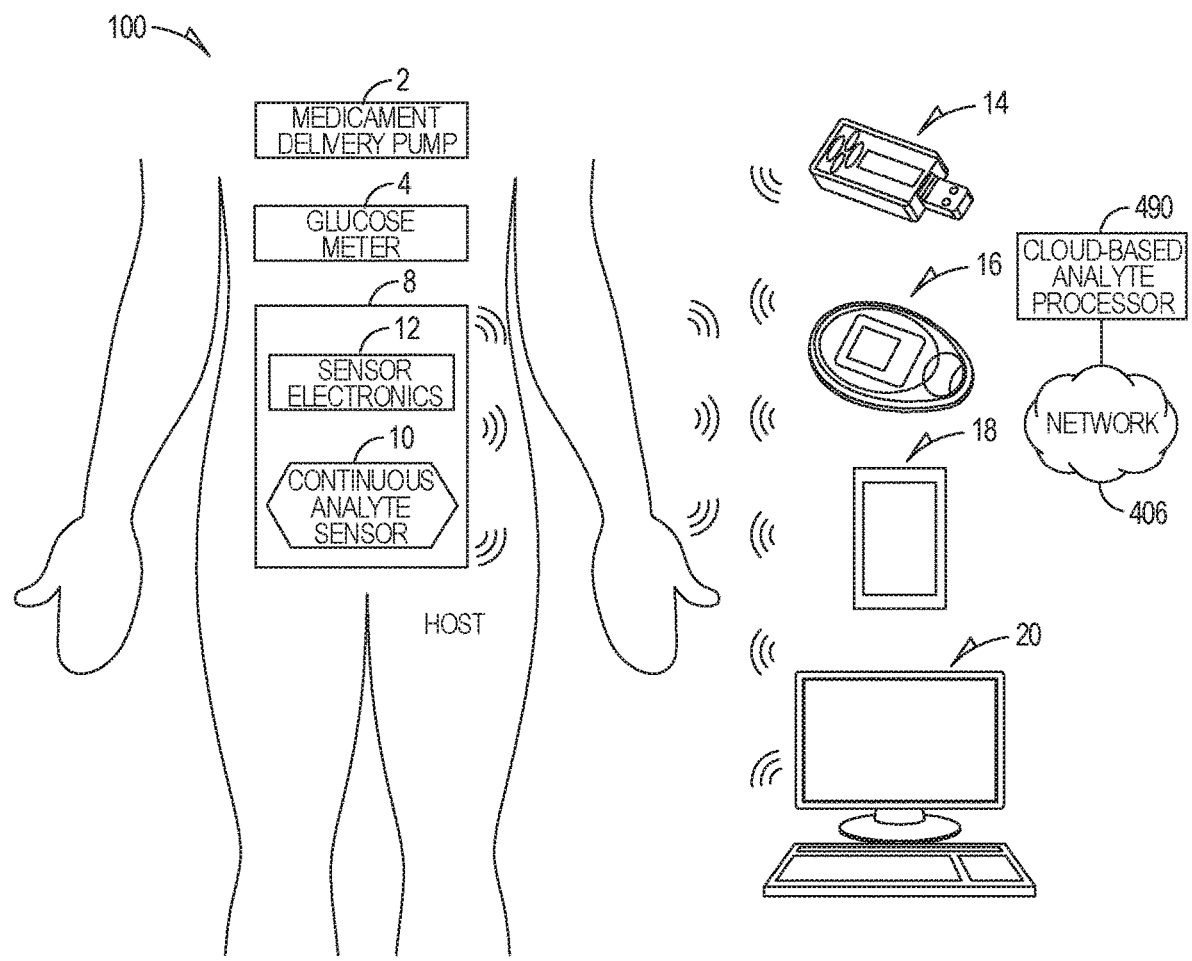
FIG. 1 is an illustration of an example analyte sensor system that may include a temperature sensor and in which temperature compensation methods may be implemented.

Accuracy of glucose sensors is important to patients, caregivers, and clinicians, as an estimated glucose concentration level obtains from a glucose sensor can be used to determine therapy or evaluate therapy effectiveness. A number of factors can affect the accuracy of glucose sensors. One factor is temperature. The present inventors have recognized, among other things, that steps can be taken to compensate for the effects of temperature on glucose sensors, which can improve the performance of a sensor system by improving the accuracy of estimated glucose levels, which in turn can decrease the mean absolute relative deviation (MARD) of a sensor system. A MARD value across an effective or indicated range of glucose levels is a common method for describing the precision and accuracy of glucose measurements by glucose sensing systems. MARD is the result of a mathematical calculation that measures the average disparity between an estimated glucose concentration level generated by a glucose sensor and a reference measurement. The lower the MARD, the more accurate the device is considered.

Definitions

To facilitate understanding of the various examples, a number of additional terms are defined below.

The term "about," as used herein, is a broad term, and is to be given its ordinary and customary meaning to a person of ordinary skill in the art (and is not to be limited to a special or customized meaning), and when associated with any numerical values or ranges, refers without limitation to the understanding that the amount or condition the terms modify can vary some beyond the stated amount so long as the function of the embodiment is realized.

The term "A/D Converter," as used herein, is a broad term, and is to be given its ordinary and customary meaning to a person of ordinary skill in the art (and is not to be limited to a special or customized meaning), and refers without limitation to hardware and/or software that converts analog electrical signals into corresponding digital signals.

The term "analyte," as used herein, is a broad term, and is to be given its ordinary and customary meaning to a person of ordinary skill in the art (and is not to be limited to a special or customized meaning), and refers without limitation to a substance or chemical constituent in a biological fluid (for example, blood, interstitial fluid, cerebral spinal fluid, lymph fluid or urine) that can be analyzed. Analytes may include naturally occurring substances, artificial substances, metabolites, and/or reaction products. In some embodiments, the analyte for measurement by the sensor heads, devices, and methods disclosed herein is glucose. However, other analytes are contemplated as well, including but not limited to lactate; bilirubin; ketones; carbon dioxide; sodium; potassium; acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-3 hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobinopathies, A,S,C,E, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione peroxidase; glycocholic acid; glycosylated hemoglobin; halofantrine; hemoglobin variants; hexosaminidase A; human erythrocyte carbonic anhydrase I; 17 alpha-hydroxyprogesterone; hypoxanthine phosphoribosyl transferase; immunoreactive trypsin; lead; lipoproteins ((a), B/A-1, β); lysozyme; mefloquine; netilmicin; phenobarbitone; phenytoin; phytanic/pristanic acid; progesterone;

prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani, Leptospira*, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *Rickettsia* (scrub typhus), *Schistosoma mansoni, Toxoplasma gondii, Trepenoma pallidium, Trypanosoma cruzi/rangeli*, vesicular *stomatis* virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids may also constitute analytes in certain embodiments. The analyte may be naturally present in the biological fluid, for example, a metabolic product, a hormone, an antigen, an antibody, and the like. Alternatively, the analyte may be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body may also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The term "baseline," as used herein is a broad term, and is to be given its ordinary and customary meaning to a person of ordinary skill in the art (and is not to be limited to a special or customized meaning) and refers without limitation to the component of an analyte sensor signal that is not related to the analyte concentration. In one example of a glucose sensor, the baseline is composed substantially of signal contribution due to factors other than glucose (for example, interfering species, non-reaction-related hydrogen peroxide, or other electroactive species with an oxidation potential that overlaps with hydrogen peroxide). In some embodiments a calibration may be defined by solving for the equation $y=mx+b$, the value of b represents the baseline of the signal. In certain embodiments, the value of b (i.e., the baseline) can be zero or about zero. This can be the result of a baseline-subtracting electrode or low bias potential settings, for example. As a result, for these embodiments, calibration can be defined by solving for the equation $y=mx$.

The term "biological sample," as used herein, is a broad term, and is to be given its ordinary and customary meaning to a person of ordinary skill in the art (and is not to be limited to a special or customized meaning), and refers without limitation to sample derived from the body or tissue of a host, such as, for example, blood, interstitial fluid, spinal fluid, saliva, urine, tears, sweat, or other like fluids.

The term "calibration," as used herein, is a broad term, and is to be given its ordinary and customary meaning to a person of ordinary skill in the art (and is not to be limited to a special or customized meaning), and refers without limitation to the process of determining the graduation of a sensor giving quantitative measurements (e.g., analyte concentration). As an example, calibration may be updated or recalibrated over time to account for changes associated with the sensor, such as changes in sensor sensitivity and sensor background. In addition, calibration of the sensor can involve, automatic, self-calibration, that is, calibration without using reference analyte values after point of use.

The term "co-analyte," as used herein, is a broad term, and is to be given its ordinary and customary meaning to a person of ordinary skill in the art (and it is not to be limited to a special or customized meaning), and refers without limitation to a molecule required in an enzymatic reaction to react with the analyte and the enzyme to form the specific product being measured. In one embodiment of a glucose sensor, an enzyme, glucose oxidase (GOX) is provided to react with glucose and oxygen (the co-analyte) to form hydrogen peroxide.

The term "comprising," as used herein, is synonymous with "including," "containing," or "characterized by," and is inclusive or open-ended and does not exclude additional, unrecited elements or method steps.

The term "computer," as used herein, is a broad term, and is to be given its ordinary and customary meaning to a person of ordinary skill in the art (and it is not to be limited to a special or customized meaning), and refers without limitation to machine that can be programmed to manipulate data.

The terms "continuous analyte sensor," and "continuous glucose sensor," as used herein, are broad terms, and are to be given their ordinary and customary meaning to a person of ordinary skill in the art (and are not to be limited to a special or customized meaning), and refer without limitation to a device that continuously or continually measures a concentration of an analyte/glucose and/or calibrates the device (such as, for example, by continuously or continually adjusting or determining the sensor's sensitivity and background), for example, at time intervals ranging from fractions of a second up to, for example, 1, 2, or 5 minutes, or longer.

The phrase "continuous glucose sensing," as used herein, is a broad term, and is to be given its ordinary and customary meaning to a person of ordinary skill in the art (and it is not to be limited to a special or customized meaning), and refers without limitation to the period in which monitoring of plasma glucose concentration is continuously or continually performed, for example, at time intervals ranging from fractions of a second up to, for example, 1, 2, or 5 minutes, or longer.

The term "counts," as used herein, is a broad term, and is to be given its ordinary and customary meaning to a person of ordinary skill in the art (and is not to be limited to a special or customized meaning), and refers without limitation to a unit of measurement of a digital signal. In one example, a raw data stream measured in counts is directly related to a voltage (for example, converted by an A/D converter), which is directly related to current from a working electrode.

The term "distal," as used herein, is a broad term, and is to be given its ordinary and customary meaning to a person of ordinary skill in the art (and it is not to be limited to a special or customized meaning), and refers without limitation to spaces relatively far from a point of reference, such as an origin or a point of attachment.

The term "domain," as used herein, is a broad term, and is to be given its ordinary and customary meaning to a person of ordinary skill in the art (and is not to be limited to a special or customized meaning), and refers without limitation to regions of a membrane that can be layers, uniform or non-uniform gradients (for example, anisotropic), functional aspects of a material, or provided as portions of the membrane.

The term "electrical conductor," as used herein, is a broad term, and is to be given its ordinary and customary meaning to a person of ordinary skill in the art (and is not to be limited to a special or customized meaning) and refers without limitation to materials that contain movable charges of electricity. When an electric potential difference is impressed across separate points on a conductor, the mobile charges within the conductor are forced to move, and an electric current between those points appears in accordance with Ohm's law.

The term "electrical conductance," as used herein, is a broad term, and is to be given its ordinary and customary meaning to a person of ordinary skill in the art (and is not to be limited to a special or customized meaning) and refers without limitation to the propensity of a material to behave as an electrical conductor. In some embodiments, the term refers to a sufficient amount of electrical conductance (e.g., material property) to provide a necessary function (electrical conduction).

The terms "electrochemically reactive surface" and "electroactive surface," as used herein, are broad terms, and are to be given their ordinary and customary meaning to a person of ordinary skill in the art (and they are not to be limited to a special or customized meaning), and refer without limitation to the surface of an electrode where an electrochemical reaction takes place. In one embodiment, a working electrode measures hydrogen peroxide (H2O2) creating a measurable electronic current.

The term "electrode," as used herein, is a broad term, and is to be given its ordinary and customary meaning to a person of ordinary skill in the art (and it is not to be limited to a special or customized meaning), and refers without limitation to a conductor through which electricity enters or leaves something such as a battery or a piece of electrical equipment. In one embodiment, the electrodes are the metallic portions of a sensor (e.g., electrochemically reactive surfaces) that are exposed to the extracellular milieu, for detecting the analyte. In some embodiments, the term electrode includes the conductive wires or traces that electrically connect the electrochemically reactive surface to connectors (for connecting the sensor to electronics) or to the electronics.

The term "elongated conductive body," as used herein, is a broad term and is to be given its ordinary and customary meaning to a person of ordinary skill in the art (and it is not to be limited to a special or customized meaning), and refers without limitation to an elongated body formed at least in part of a conductive material and includes any number of coatings that may be formed thereon. By way of example, an "elongated conductive body" may mean a bare elongated conductive core (e.g., a metal wire) or an elongated conductive core coated with one, two, three, four, five, or more than five layers of material, each of which may or may not be conductive.

The term "enzyme," as used herein, is a broad term, and is to be given its ordinary and customary meaning to a person of ordinary skill in the art (and it is not to be limited to a special or customized meaning), and refers without limitation to a protein or protein-based molecule that speeds up a chemical reaction occurring in a living thing. Enzymes may act as catalysts for a single reaction, converting a reactant (also called an analyte herein) into a specific product. In one embodiment of a glucose oxidase-based glucose sensor, an enzyme, glucose oxidase (GOX) is provided to react with glucose (the analyte) and oxygen to form hydrogen peroxide.

The term "filtering," as used herein, is a broad term, and is to be given its ordinary and customary meaning to a person of ordinary skill in the art (and is not to be limited to a special or customized meaning), and refers without limitation to modification of a set of data to make it smoother and more continuous and remove or diminish outlying points, for example, by performing a moving average of the raw data stream.

The term "function," as used herein, is a broad term, and is to be given its ordinary and customary meaning to a person of ordinary skill in the art (and it is not to be limited to a special or customized meaning), and refers without limitation to an action or use for which something is suited or designed.

The term "GOx," as used herein, is a broad term, and is to be given its ordinary and customary meaning to a person of ordinary skill in the art (and is not to be limited to a special or customized meaning), and refers without limitation to the enzyme Glucose Oxidase (e.g., GOx is an abbreviation).

The term "host," as used herein, is a broad term, and is to be given its ordinary and customary meaning to a person of ordinary skill in the art (and is not to be limited to a special or customized meaning), and refers without limitation to animals, including humans.

The term "inactive enzyme," as used herein, is a broad term, and is to be given its ordinary and customary meaning to a person of ordinary skill in the art (and is not to be limited to a special or customized meaning), and refers without limitation to an enzyme (such as, for example, glucose oxidase, GOx) that has been rendered inactive (e.g., by denaturing of the enzyme) and has substantially no enzymatic activity. Enzymes can be inactivated using a variety of techniques known in the art, such as but not limited to heating, freeze-thaw, denaturing in organic solvent, acids or bases, cross-linking, genetically changing enzymatically critical amino acids, and the like. In some embodiments, a solution containing active enzyme can be applied to the sensor, and the applied enzyme subsequently inactivated by heating or treatment with an inactivating solvent.

The terms "insulative properties," "electrical insulator," and "insulator," as used herein, are broad terms, and are to be given their ordinary and customary meaning to a person of ordinary skill in the art (and are not to be limited to a special or customized meaning) and refer without limitation to the tendency of materials that lack mobile charges to prevent movement of electrical charges between two points. In one embodiment, an electrically insulative material may be placed between two electrically conductive materials, to prevent movement of electricity between the two electrically conductive materials. In some embodiments, the terms refer to a sufficient amount of insulative property (e.g., of a material) to provide a necessary function (electrical insulation). The terms "insulator" and "non-conductive material" can be used interchangeably herein.

The term "in vivo portion," as used herein, is a broad term, and is to be given its ordinary and customary meaning to a person of ordinary skill in the art (and is not to be limited to a special or customized meaning), and refers without limitation to a portion of a device that is to be implanted or inserted into the host. In one embodiment, an in vivo portion of a transcutaneous sensor is a portion of the sensor that is inserted through the host's skin and resides within the host.

The term "membrane system," as used herein, is a broad term, and is to be given its ordinary and customary meaning to a person of ordinary skill in the art (and is not to be limited to a special or customized meaning), and refers without limitation to a permeable or semi-permeable membrane that can include two or more domains and is typically constructed of materials of a few microns thickness or more, which may be permeable to oxygen and are optionally permeable to glucose. In one example, the membrane system may include an immobilized glucose oxidase enzyme, which enables an electrochemical reaction to occur to measure a concentration of glucose.

The term "operably connected," as used herein, is a broad term, and is to be given its ordinary and customary meaning to a person of ordinary skill in the art (and is not to be limited to a special or customized meaning), and refers without limitation to one or more components being linked to another component(s) in a manner that allows transmission of signals between the components. For example, one or more electrodes can be used to detect the amount of glucose in a sample and convert that information into a signal; the signal can then be transmitted to an electronic circuit. In this case, the electrode is "operably linked" to the electronic circuit. These terms are broad enough to include wired and wireless connectivity.

The term "potentiostat," as used herein, is a broad term, and is to be given its ordinary and customary meaning to a person of ordinary skill in the art (and is not to be limited to a special or customized meaning), and refers without limitation to an electrical system that applies a potential between the working and reference electrodes of a two- or three-electrode cell at a preset value and measures the current flow through the working electrode. The potentiostat forces whatever current is necessary to flow between the working and counter electrodes to keep the desired potential, as long as the needed cell voltage and current do not exceed the compliance limits of the potentiostat.

The terms "processor module" and "microprocessor," as used herein, are broad terms, and are to be given their ordinary and customary meaning to a person of ordinary skill in the art (and they are not to be limited to a special or customized meaning), and refer without limitation to a computer system, state machine, processor, or the like designed to perform arithmetic and logic operations using logic circuitry that responds to and processes the basic instructions that drive a computer.

The term "proximal," as used herein, is a broad term, and is to be given its ordinary and customary meaning to a person of ordinary skill in the art (and it is not to be limited to a special or customized meaning), and refers without limitation to near to a point of reference such as an origin or a point of attachment.

The terms "raw data stream" and "data stream," as used herein, are broad terms, and are to be given their ordinary and customary meaning to a person of ordinary skill in the art (and they are not to be limited to a special or customized meaning), and refer without limitation to an analog or digital signal directly related to the analyte concentration measured by the analyte sensor. In one example, the raw data stream is digital data in counts converted by an A/D converter from an analog signal (for example, voltage or amps) representative of an analyte concentration. The terms broadly encompass a plurality of time spaced data points from a substantially continuous analyte sensor, which may include individual measurements taken at time intervals ranging from fractions of a second up to, for example, 1, 2, or 5 minutes or longer.

The term "RAM," as used herein, is a broad term, and is to be given its ordinary and customary meaning to a person of ordinary skill in the art (and is not to be limited to a special or customized meaning), and refers without limitation to a data storage device for which the order of access to different locations does not affect the speed of access. RAM is broad enough to include SRAM, for example, which is static random access memory that retains data bits in its memory as long as power is being supplied.

The term "ROM," as used herein, is a broad term, and is to be given its ordinary and customary meaning to a person of ordinary skill in the art (and is not to be limited to a special or customized meaning), and refers without limitation to read-only memory, which is a type of data storage device manufactured with fixed contents. ROM is broad enough to include EEPROM, for example, which is electrically erasable programmable read-only memory (ROM).

The terms "reference analyte values" and "reference data," as used herein, are broad terms, and are to be given their ordinary and customary meaning to a person of ordinary skill in the art (and they are not to be limited to a special or customized meaning), and refer without limitation to reference data from a reference analyte monitor, such as a blood glucose meter, or the like, including one or more reference data points. In some embodiments, the reference glucose values are obtained from a self-monitored blood glucose (SMBG) test (for example, from a finger or forearm blood test) or a YSI (Yellow Springs Instruments) test, for example.

The term "regression," as used herein, is a broad term, and is to be given its ordinary and customary meaning to a person of ordinary skill in the art (and it is not to be limited to a special or customized meaning), and refers without limitation to finding a line in which a set of data has a minimal measurement (for example, deviation) from that line. Regression can be linear, non-linear, first order, second order, and so forth. One example of regression is least squares regression.

The term "sensing region," as used herein, is a broad term, and is to be given its ordinary and customary meaning to a person of ordinary skill in the art (and is not to be limited to a special or customized meaning), and refers without limitation to the region of a monitoring device responsible for the detection of a particular analyte. In one embodiment, the sensing region may include a non-conductive body, at least one electrode, a reference electrode and optionally a counter electrode passing through and secured within the body forming an electroactive surface at one location on the body and an electronic connection at another location on the body, and a membrane system affixed to the body and covering the electroactive surface.

The terms "sensitivity" or "sensor sensitivity," as used herein, are broad terms, and are to be given their ordinary and customary meaning to a person of ordinary skill in the art (and is not to be limited to a special or customized meaning), and refer without limitation to an amount of signal produced by a certain concentration of a measured analyte, or a measured species (such as, for example, H2O2) associated with the measured analyte (such as, for example, glucose). For example, in one embodiment, a sensor has a sensitivity of from about 1 to about 300 picoAmps of current for every 1 mg/dL of glucose analyte.

The term "sensitivity profile" or "sensitivity curve," as used herein, are broad terms, and are to be given their ordinary and customary meaning to a person of ordinary skill in the art (and is not to be limited to a special or customized meaning), and refer without limitation to a representation of a change in sensitivity over time.

The terms "sensor analyte values" and "sensor data," as used herein, are broad terms, and are to be given their ordinary and customary meaning to a person of ordinary skill in the art (and they are not to be limited to a special or customized meaning), and refer without limitation to data received from a continuous analyte sensor, including one or more time-spaced sensor data points.

The terms "sensor electronics" and "electronic circuitry," as used herein, are broad terms, and are to be given their ordinary and customary meaning to a person of ordinary skill in the art (and they are not to be limited to a special or customized meaning), and refer without limitation to the components (for example, hardware and/or software) of a device configured to process data. In the case of an analyte sensor, the data includes biological information obtained by a sensor regarding the concentration of the analyte in a biological fluid. U.S. Pat. Nos. 4,757,022, 5,497,772 and 4,787,398 describe suitable electronic circuits that can be utilized with devices of certain embodiments.

The term "sensor environment" or "sensor operational environment," as used herein, are broad terms and are to be given their ordinary and customary meaning to a person of ordinary skill in the art (and is not to me limited to a special or customized meaning), and refer without limitation to the biological environment in which a sensor is operating.

The terms "substantial" and "substantially," as used herein, are broad terms, and are to be given their ordinary and customary meaning to a person of ordinary skill in the art (and are not to be limited to a special or customized meaning), and refer without limitation to being largely but not necessarily wholly that which is specified.

The term "thermal conductivity," as used herein, is a broad term, and is to be given its ordinary and customary meaning to a person of ordinary skill in the art (and it is not to be limited to a special or customized meaning), and refers without limitation to the quantity of heat transmitted, due to unit temperature gradient, in unit time under steady conditions in a direction normal to a surface of unit area.

The term "thermal coefficient," as used herein, is a broad term, and is to be given its ordinary and customary meaning to a person of ordinary skill in the art (and is not to be limited to a special or customized meaning), and refers without limitation to the change in resistance of a material at various temperatures.

The term "thermally conductive material," as used herein, is a broad term, and is to be given its ordinary and customary meaning to a person of ordinary skill in the art (and is not to be limited to a special or customized meaning), and refers without limitation to materials displaying a high degree of thermal conductivity.

The term "thermocouple," as used herein, is a broad term, and is to be given its ordinary and customary meaning to a person of ordinary skill in the art (and is not to be limited to a special or customized meaning), and refers without limitation to a device including two different conductors (such as, for example metal alloys) that produce a voltage, proportional to a temperature difference, between either ends of the two conductors.

Overview

Some analyte sensors measure a concentration of a substance (e.g., glucose) within the body (e.g., measure glucose concentration in blood or interstitial fluid at a subcutaneous location). The output of analyte sensors can be affected by temperature. The temperature of subcutaneous regions of the body in which a sensor may be located can vary from person to person and can vary over time in an individual person. For example, the subcutaneous temperature can be affected by bodily temperature changes (such as fever or cyclic variations) as well as ambient temperatures changes. For example, hot or cold water exposure, warm clothing, cold weather exposure, and sunlight can change the subcutaneous temperature of a host. When conditions such as these are present, temperature variations can cause inaccuracies in estimation of glucose concentration levels. The accuracy and precision of estimated glucose concentration levels can be improved by compensating for temperature fluctuations at the sensing site or in the sensor when the sensor is worn by a host.

The performance of analyte sensor systems can be improved by compensating for these temperature effects. For example, temperature compensation can increase sensory accuracy, or decrease MARD. Temperature compensation presents implementation challenges, however, as it can be difficult to know the actual temperature at the sensing site, or how much to compensate, and the temperature of the body of the host and various system components can vary from each other and vary over time.

In some examples, temperature compensation can be applied to the sensitivity value used to translate signals from a sensor into estimated analyte concentration levels (e.g., a 3% change in sensitivity for every 1° C. deviation from a reference temperature (e.g., 35° C.)). In some examples, temperature compensation can be applied directly to estimated glucose values. In some instances, compensating glucose values instead of sensor sensitivity may produce more accurate values. For example, in addition to variations in enzymatic sensitivity, other effects may affect glucose concentration levels or sensor response. The additional temperature effects can include local glucose concentration variations (as opposed to systemic glucose levels), compartment bias (differences in glucose concentration in interstitial fluid vs. blood), and non-enzyme sensor bias (e.g., an electrochemical baseline signal that is not generated by a glucose/enzyme interaction). A model can be developed to account for some or all of these additional factors, which may provide more accurate estimates of glucose concentration levels.

Example System

FIG. 1 depicts in an example system 100 in which example temperature compensation systems, devices, and methods may be implemented. The system 100 may include a continuous analyte sensor system 8 including sensor electronics 12 and a continuous analyte sensor 10. The system 100 may include other devices and/or sensors, such as medicament delivery pump 2 (which may be communicatively coupled with the continuous analyte sensor system, e.g. to enable closed-loop therapy) and glucose meter 4, such as a blood glucose meter, which may be communicatively coupled to the continuous analyte sensor system 8. The continuous analyte sensor 10 may be physically coupled to sensor electronics 12 and may be releasably attachable to the sensor electronics 12 or integral with (e.g., non-releasably attached to) the sensor electronics 12. The sensor electronics 12, medicament delivery pump 2, and/or glucose meter 4 may also couple with one or more devices, such as display devices 14, 16, 18, and/or 20.

In some example implementations, the system 100 may include a cloud-based analyte processor 490 configured to analyze analyte data (and/or other patient-related data) provided via network 406 (e.g., via wired, wireless, or a combination thereof) from sensor system 8 and other devices, such as display devices 14-20 and the like, associated with the host (also referred to as a subject or patient) and generate reports providing high-level information, such as statistics, regarding the measured analyte over a certain time frame. A full discussion of using a cloud-based analyte processing system may be found in U.S. Patent Publication No. US-2013-0325352-A1, entitled "Cloud-Based Processing of Analyte Data" and filed on Mar. 7, 2013, herein incorporated by reference in its entirety. In some implementations, one or more steps of the temperature compensation algorithm can be performed in the cloud.

In some example implementations, the sensor electronics 12 may include electronic circuitry associated with measuring and processing data generated by the continuous analyte sensor 10. This generated continuous analyte sensor data may also include algorithms, which can be used to process and calibrate the continuous analyte sensor data, although these algorithms may be provided in other ways as well. The sensor electronics 12 may include hardware, firmware, software, or a combination thereof, to provide measurement of levels of the analyte via a continuous analyte sensor, such as a continuous glucose sensor. An example implementation of the sensor electronics 12 is described further below with respect to FIG. 2B.

In one implementation, temperature compensation methods may be performed by the sensor electronics 12.

The sensor electronics 12 may, as noted, couple (e.g., wirelessly and the like) with one or more devices, such as display devices 14, 16, 18, and/or 20. The display devices 14, 16, 18, and/or 20 may be configured for presenting information (and/or alarming), such as sensor information transmitted by the sensor electronics 12 for display at the display devices 14, 16, 18, and/or 20.

The display devices may include a relatively small display device 14. In some example implementations, the relatively small display device 14 may be or be part of a key fob, a wrist watch, a belt, a necklace, a pendent, a piece of jewelry, an adhesive patch, a pager, a key fob, a plastic card (e.g., credit card), an identification (ID) card, and/or the like. This small display device 14 may include a relatively small display (e.g., smaller than the large display device 16) and may be configured to display certain types of displayable sensor information, such as a numerical value, and an arrow, or a color code. The device 14 may be configured as a data receiving or tracking device 14 (e.g. blood glucose meter or CGM receiver) and may include a communication device (e.g. a US-B port or wireless communication transceiver) for uploading data to another device.

In some example implementations, the relatively large, hand-held display device 16 may include a hand-held receiver device, a palm-top computer, and/or the like. This large display device may include a relatively larger display (e.g., larger than the small display device 14) and may be configured to display information, such as a graphical representation of the continuous sensor data including current and historic sensor data output by sensor system 8. The hand-held display device 16 may, for example, be a CGM controller or pump controller.

The display devices may also include a mobile device 18 (e.g., a smart phone, tablet, or other smart device). The display devices may also include a computer 20, and/or any other user equipment configured to at least present information (e.g., medicament delivery information, discrete self-monitoring glucose readings, heart rate monitor, caloric intake monitor, and the like).

Any of the display devices may be coupled to the network 406 via a wired or wireless (e.g., cellular, Bluetooth, Wi-Fi, MICS, ZigBee) connection, and may include a processor and memory circuit for storing and processing information. In some examples, the temperature compensation methods may be performed at least in part by one or more of the display devices.

In some example implementations, the continuous analyte sensor 10 may include a sensor for detecting and/or measuring analytes, and the continuous analyte sensor 10 may be configured to continuously detect and/or measure analytes as a non-invasive device, a subcutaneous device, a transdermal device, and/or an intravascular device. In some example implementations, the continuous analyte sensor 10 may analyze a plurality of intermittent blood samples, although other analytes may be used as well.

In some example implementations, the continuous analyte sensor 10 may include a glucose sensor configured to measure glucose in the blood or interstitial fluid using one or more measurement techniques, such as enzymatic, chemical, physical, electrochemical, spectrophotometric, polarimetric, calorimetric, iontophoretic, radiometric, immunochemical, and the like. In implementations in which the continuous analyte sensor 10 includes a glucose sensor, the glucose sensor may include any device capable of measuring the concentration of glucose and may use a variety of techniques to measure glucose including invasive, minimally invasive, and non-invasive sensing techniques (e.g., fluorescence monitoring), to provide data, such as a data stream, indicative of the concentration of glucose in a host. The data stream may be sensor data (raw and/or filtered), which may be converted into a calibrated data stream used to provide a value of glucose to a host, such as a user, a patient, or a caretaker (e.g., a parent, a relative, a guardian, a teacher, a doctor, a nurse, or any other individual that has an interest in the wellbeing of the host). Moreover, the continuous analyte sensor 10 may be implanted as at least one of the following types of sensors: an implantable glucose sensor, a transcutaneous glucose sensor, implanted in a host vessel or extracorporeally, a subcutaneous sensor, a refillable subcutaneous sensor, an intravascular sensor.

Although the disclosure herein refers to some implementations that include a continuous analyte sensor 10 that includes a glucose sensor, the continuous analyte sensor 10 may include other types of analyte sensors as well. Moreover, although some implementations refer to the glucose sensor as an implantable glucose sensor, other types of devices capable of detecting a concentration of glucose and providing an output signal representative of glucose concentration may be used as well. Furthermore, although the description herein refers to glucose as the analyte being measured, processed, and the like, other analytes may be used as well including, for example, ketone bodies (e.g., acetone, acetoacetic acid and beta hydroxybutyric acid, lactate, etc.), glucagon, acetyl-CoA, triglycerides, fatty acids, intermediaries in the citric acid cycle, choline, insulin, cortisol, testosterone, and the like.

Electronics of an Example Analyte Sensor System

Figure 2A:
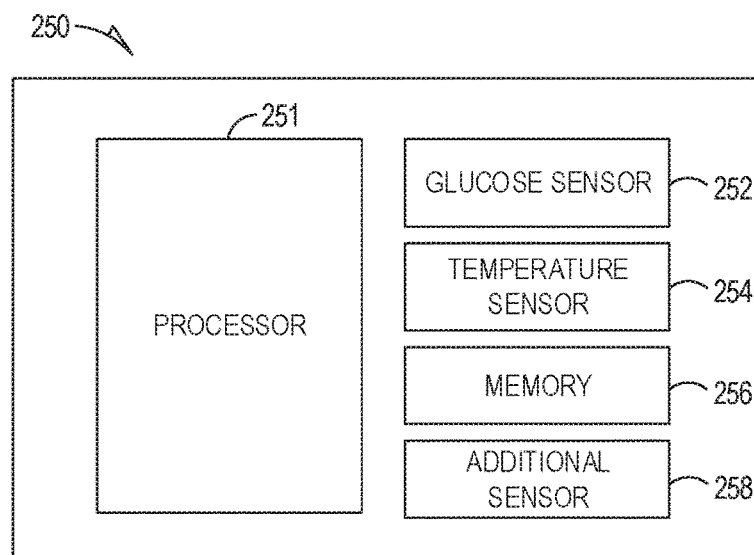
FIG. 2A is a schematic illustration of an example analyte sensor system.

FIG. 2A is a schematic illustration of an example analyte sensor system 250, which may for example, be the system 8 shown in FIG. 1. The analyte sensor system may include an analyte sensor such as a glucose sensor 252, one or more temperature sensors 254, a processor 251, and a memory 256. The processor may receive a glucose sensor signal indicative of a glucose concentration level from the glucose sensor 252 and receive a temperature sensor signal indicative of a temperature parameter (e.g. absolute or relative temperature, or a temperature gradient) from the temperature sensor 254. The sensor system 250 may also include one or more additional sensors 258, which may include, for example, a heart rate sensor, activity sensor (e.g. accelerometer), or a pressure gauge (e.g. to measure compression of the sensor against a host).

The processor 251 may determine a temperature-compensated glucose concentration level (or other analyte concentration level) based on the glucose sensor signal, the temperature sensor signal and optionally also based on one or more signals from additional sensor(s) 258. The processor 251 may determine a specific temperature-compensated sensitivity value (e.g., analyte sensor sensitivity value based on the temperature), or may determine a compensated estimated glucose value. The signal from the temperature sensor 254 may be used as an approximation of a temperature at an analyte sensor, or the signal from the temperature sensor 254 may be processed (e.g., using methods described in detail below) to determine an estimated analyte temperature sensor based on the signal from the temperature sensor 254. In some examples, the processor may retrieve instructions or information from a memory 256 to determine temperature-compensated glucose concentration level. For example, the processor may access a look-up table, or apply an algorithm based on the glucose sensor signal and temperature sensor signal or apply the glucose sensor signal and temperature signal to a model (e.g., use a state model or neural network). In some examples, the processor may retrieve executable instructions from the memory 256 (or a separate memory that may be operatively coupled to or integrated into the processor.) In some examples, the processor may include, or be part of, an application-specific integrated circuit (ASIC) that may be configured to determine a temperature-compensated glucose concentration level. In various examples, any one or more of the methods described herein or illustrated in FIGS. 6-14 may be executed by the processor 251 or temperature-compensated glucose sensor, either alone, or in combination with other processors or devices, such as the devices illustrated in FIG. 5.

Figure 2B:
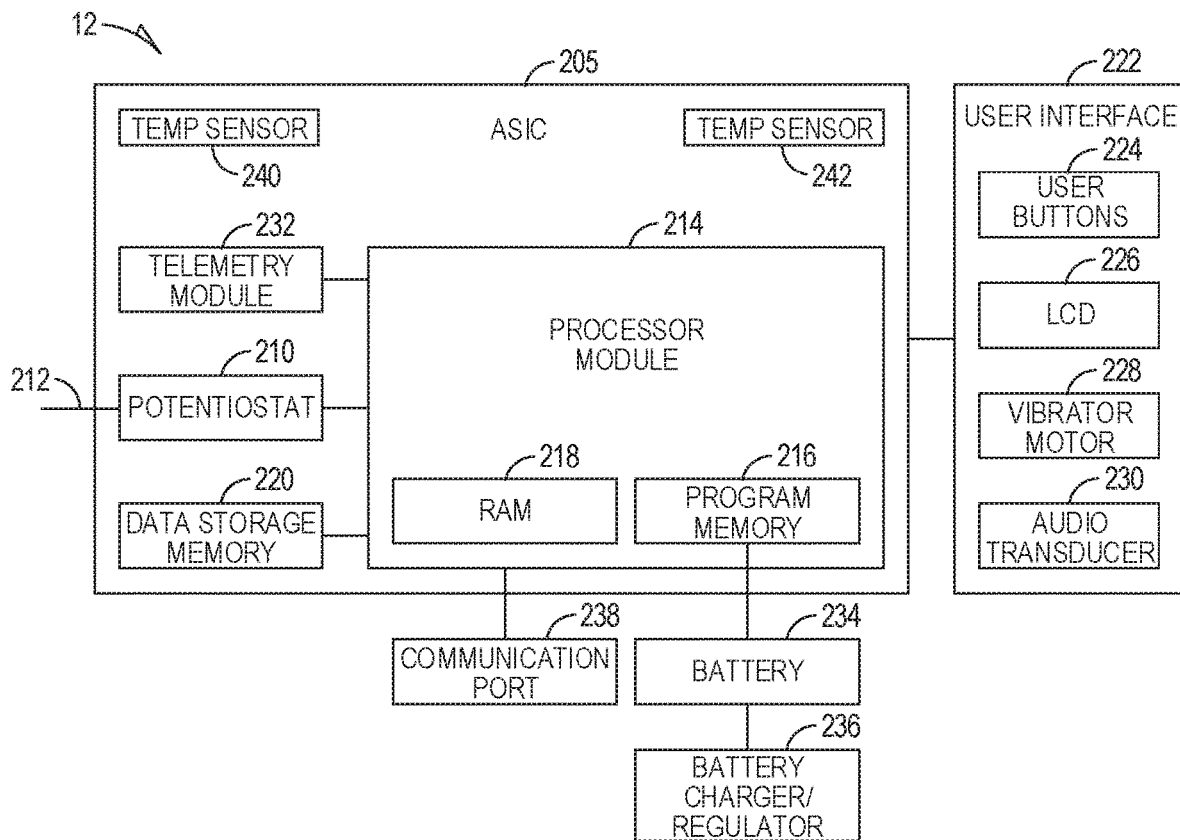
FIG. 2B is a schematic illustration of example sensor electronics portions of an analyte sensor system.

FIG. 2B depicts a more-detailed illustration of example sensor electronics 12. The sensor electronics may, for example, be part of a system of devices as shown in FIG. 1. The sensor electronics 12 may include sensor electronics that are configured to process sensor information, such as sensor data, and generate transformed sensor data and displayable sensor information, e.g., via a processor module 214. For example, the processor module 214 may transform sensor data into one or more of the following: temperature-compensated data, filtered sensor data (e.g., one or more filtered analyte concentration values), raw sensor data, calibrated sensor data (e.g., one or more calibrated analyte concentration values), rate of change information, trend information, rate of acceleration/deceleration information, sensor diagnostic information, location information, alarm/alert information, calibration information such as may be determined by calibration algorithms, smoothing and/or filtering algorithms of sensor data, and/or the like.

The sensor electronics 12 may include a first temperature sensor 240. In some examples, a signal from the temperature sensor 240 may be used for temperature compensation, e.g., to compensate for temperature effects on an analyte sensor. In some examples, the sensor electronics 12 may include an optional second temperature sensor 242. Signals from the first temperature sensor 240 and second temperature sensor 242 may be used to determine a heat flux or temperature gradient.

In some embodiments, a processor module 214 may be configured to achieve a substantial portion, if not all, of the data processing, including data processing pertaining to factory calibration or temperature compensation. A factory calibration may be a calibration of continuous analyte sensors that are capable of achieving high levels of accuracy, without (or with reduce) reliance on reference data from a reference analyte monitor (e.g., a blood glucose meter). Processor module 214 may be integral to sensor electronics 12 and/or may be located remotely, such as in one or more of devices 14, 16, 18, and/or 20 and/or cloud 490. In some embodiments, processor module 214 may include a plurality of smaller subcomponents or submodules. For example, processor module 214 may include an alert module (not shown) or prediction module (not shown), or any other suitable module that may be utilized to efficiently process data. When processor module 214 is made up of a plurality of submodules, the submodules may be located within processor module 214, including within the sensor electronics 12 or other associated devices (e.g., 14, 16, 18, 20 and/or 490). For example, in some embodiments, processor module 214 may be located at least partially within a cloud-based analyte processor 490 or elsewhere in network 406.

In some example implementations, the processor module 214 may be configured to calibrate the sensor data, and the data storage memory 220 may store the calibrated sensor data points as transformed sensor data. Moreover, the processor module 214 may be configured, in some example implementations, to wirelessly receive calibration information from a display device, such as devices 14, 16, 18, and/or 20, to enable calibration of the sensor data from sensor 12. Furthermore, the processor module 214 may be configured to perform additional algorithmic processing on the sensor data (e.g., calibrated and/or filtered data and/or other sensor information), and the data storage memory 220 may be configured to store the transformed sensor data and/or sensor diagnostic information associated with the algorithms. The processor module 214 may further be configured to store and use calibration information determined from a calibration.

In some example implementations, some or all of the sensor electronics 12 may be incorporated into include an ASIC 205, which may be coupled via a wired or wireless connection to a user interface 222. For example, the ASIC 205 may include a potentiostat 210, a telemetry module 232 for transmitting data from the sensor electronics 12 to one or more devices, such as devices 14, 16, 18, and/or 20, and/or other components for signal processing and data storage (e.g., processor module 214 and data storage memory 220). Although FIG. 2B depicts ASIC 205, other types of circuitry may be used as well, including field programmable gate arrays (FPGA), one or more microprocessors configured to provide some (if not all of) the processing performed by the sensor electronics 12, analog circuitry, digital circuitry, or a combination thereof. In addition, the ASIC 205 may include only a subset (one or more) of the devices, and any of the devices 210, 214, 216, 218, 220, 232, 240, 242 may be included in the ASIC or provided as discrete components or integrated together as a separate ASIC (e.g., as a second ASIC or third ASIC).

In the example depicted in FIG. 2B, through a first input port for sensor data, the potentiostat 210 may be coupled to a continuous analyte sensor 10, such as a glucose sensor, to generate sensor data from the analyte. The potentiostat 210 may also provide via data line 212 a voltage to an analyte sensor such as the continuous analyte sensor 10 (shown in FIG. 5) or the sensors shown in FIG. 2C, 3, 4, 5A, or 5B, to bias the sensor for measurement of a value (e.g., a current and the like) indicative of the analyte concentration in a host (also referred to as the analog portion of the sensor). The potentiostat 210 may have one or more channels depending on the number of working electrodes at the continuous analyte sensor 10.

In some example implementations, the potentiostat 210 may include a resistor that translates a current value from the sensor 10 into a voltage value, while in some example implementations, a current-to-frequency converter (not shown) may also be configured to integrate continuously a measured current value from the sensor 10 using, for example, a charge-counting device. In some example implementations, an analog-to-digital converter (not shown) may digitize the analog signal from the sensor 10 into so-called "counts" to allow processing by the processor module 214. The resulting counts may be directly related to the current measured by the potentiostat 210, which may be directly related to an analyte level, such as a glucose level, in the host.

The telemetry module 232 may be operably connected to processor module 214 and may provide the hardware, firmware, and/or software that enable wireless communication between the sensor electronics 12 and one or more other devices, such as display devices, processors, network access devices, and the like. A variety of wireless radio technologies that can be implemented in the telemetry module 232 include Bluetooth, Bluetooth Low-Energy, ANT, ANT+, ZigBee, IEEE 802.11, IEEE 802.16, cellular radio access technologies, radio frequency (RF), infrared (IR), paging network communication, magnetic induction, satellite data communication, spread spectrum communication, frequency hopping communication, near field communications, and/or the like. In some example implementations, the telemetry module 232 may include a Bluetooth chip, although Bluetooth technology may also be implemented in a combination of the telemetry module 232 and the processor module 214.

The processor module 214 may control the processing performed by the sensor electronics 12. For example, the processor module 214 may be configured to process data (e.g., counts), from the sensor, filter the data, calibrate the data, perform fail-safe checking, and/or the like.

In some example implementations, the processor module 214 may include a digital filter, such as for example an infinite impulse response (IIR) or a finite impulse response (FIR) filter. This digital filter may smooth a raw data stream received from sensor 10. Generally, digital filters are programmed to filter data sampled at a predetermined time interval (also referred to as a sample rate). In some example implementations, such as when the potentiostat 210 is configured to measure the analyte (e.g., glucose and/or the like) at discrete time intervals, these time intervals determine the sampling rate of the digital filter. In some example implementations, the potentiostat 210 may be configured to measure continuously the analyte, for example, using a current-to-frequency converter. In these current-to-frequency converter implementations, the processor module 214 may be programmed to request, at predetermined time intervals (acquisition time), digital values from the integrator of the current-to-frequency converter. These digital values obtained by the processor module 214 from the integrator may be averaged over the acquisition time due to the continuity of the current measurement. As such, the acquisition time may be determined by the sampling rate of the digital filter.

The processor module 214 may further include a data generator (not shown) configured to generate data packages for transmission to devices, such as the display devices 14, 16, 18, and/or 20. Furthermore, the processor module 214 may generate data packets for transmission to these outside sources via telemetry module 232. In some example implementations, the data packages may, as noted, be customizable for each display device, and/or may include any available data, such as temperature information or temperature-related information, temperature-compensated data, accelerometer data, motion data, location data, a time stamp, displayable sensor information, transformed sensor data, an identifier code for the sensor and/or sensor electronics 12, raw data, filtered data, calibrated data, rate of change information, trend information, error detection or correction, temperature information, or any combination thereof.

The processor module 214 may also include a program memory 216 and other memory 218. The processor module 214 may be coupled to a communications interface, such as a communication port 238, and a source of power, such as a battery 234. Moreover, the battery 234 may be further coupled to a battery charger and/or regulator 236 to provide power to sensor electronics 12 and/or charge the battery 234.

The program memory 216 may be implemented as a semi-static memory for storing data, such as an identifier for a coupled sensor 10 (e.g., a sensor identifier (ID)) and for storing code (also referred to as program code) to configure the ASIC 205 to perform one or more of the operations/functions described herein. For example, the program code may configure processor module 214 to process data streams or counts, filter, perform the calibration methods, perform fail-safe checking, and the like.

The memory 218 may also be used to store information. For example, the processor module 214 including memory 218 may be used as the system's cache memory, where temporary storage may be provided for recent sensor data received from the sensor. In some example implementations, the memory may include memory storage components, such as read-only memory (ROM), random-access memory (RAM), dynamic-RAM, static-RAM, non-static RAM, easily erasable programmable read only memory (EEPROM), rewritable ROMs, flash memory, and the like.

The data storage memory 220 may be coupled to the processor module 214 and may be configured to store a variety of sensor information. In some example implementations, the data storage memory 220 stores one or more days of continuous analyte sensor data. For example, the data storage memory may store 1, 2, 3, 4, 5, 6, 7, 8, 9, 10, 11, 12, 13, 14, 15, 20, and/or 30 (or more days) of continuous analyte sensor data received from sensor 10. The stored sensor information may include one or more of the following: temperature information or temperature-related information, temperature-compensated data, a time stamp, raw sensor data (one or more raw analyte concentration values), calibrated data, filtered data, transformed sensor data, and/or any other displayable sensor information, calibration information (e.g., reference BG values and/or prior calibration information such as from factory calibration), sensor diagnostic information, temperature information, and the like.

The user interface 222 may include a variety of interfaces, such as one or more buttons 224, a liquid crystal display (LCD) or organic light emitting diode (OLED) display 226, a vibrator 228, an audio transducer (e.g., speaker) 230, a backlight (not shown), and/or the like. The components that include the user interface 222 may provide controls to interact with the user (e.g., the host). One or more buttons 224 may allow, for example, toggle, menu selection, option selection, status selection, yes/no response to on-screen questions, a "turn off" function (e.g., for an alarm), an "acknowledged" function (e.g., for an alarm), a reset, and/or the like. The display 226 may provide the user with, for example, visual data output. The audio transducer 230 (e.g., speaker) may provide audible signals in response to triggering of certain alerts, such as present and/or predicted hyperglycemic and hypoglycemic conditions. In some example implementations, audible signals may be differentiated by tone, volume, duty cycle, pattern, duration, and/or the like. In some example implementations, the audible signal may be configured to be silenced (e.g., acknowledged or turned off) by pressing one or more buttons 224 on the sensor electronics 12 and/or by signaling the sensor electronics 12 using a button or selection on a display device (e.g., key fob, cell phone, and/or the like).

Although audio and vibratory alarms are described with respect to FIG. 2B, other alarming mechanisms may be used as well. For example, in some example implementations, a tactile alarm is provided including a poking mechanism configured to "poke" or physically contact the patient in response to one or more alarm conditions.

The battery 234 may be operatively connected to the processor module 214 (and possibly other components of the sensor electronics 12) and provide the necessary power for the sensor electronics 12. In some example implementations, the battery may be a Lithium Manganese Dioxide battery, however any appropriately sized and powered battery can be used (e.g., AAA, Nickel-cadmium, Zinc-carbon, Alkaline, Lithium, Nickel-metal hydride, Lithium-ion, Zinc-air, Zinc-mercury oxide, Silver-zinc, or hermetically-sealed). In some example implementations, the battery may be rechargeable. In some example implementations, a plurality of batteries can be used to power the system. In yet other implementations, the receiver can be transcutaneously powered via an inductive coupling, for example.

A battery charger and/or regulator 236 may be configured to receive energy from an internal and/or external charger. In some example implementations, a battery regulator (or balancer) 236 regulates the recharging process by bleeding off excess charge current to allow all cells or batteries in the sensor electronics 12 to be fully charged without overcharging other cells or batteries. In some example implementations, the battery 234 (or batteries) may be configured to be charged via an inductive and/or wireless charging pad, although any other charging and/or power mechanism may be used as well.

One or more communication ports 238, also referred to as external connector(s), may be provided to allow communication with other devices, for example a PC communication (com) port can be provided to enable communication with systems that are separate from, or integral with, the sensor electronics 12. The communication port, for example, may include a serial (e.g., universal serial bus or "USB") communication port, and allow for communicating with another computer system (e.g., PC, personal digital assistant or "PDA," server, or the like). In some example implementations, the sensor electronics 12 may be able to transmit historical data to a PC or other computing device for retrospective analysis by a patient and/or HCP. As another example of data transmission, factory information may also be sent to the algorithm from the sensor or from a cloud data source.

The one or more communication ports 238 may further include a second input port in which calibration data may be received, and an output port which may be employed to transmit calibrated data, or data to be calibrated, to a receiver or mobile device. It will be understood that the ports may be separated physically, but in alternative implementations a single communication port may provide the functions of both the second input port and the output port.

In some continuous analyte sensor systems, an on-skin portion of the sensor electronics may be simplified to minimize complexity and/or size of on-skin electronics, for example, providing only raw, calibrated, and/or filtered data to a display device configured to run calibration and other algorithms required for displaying the sensor data. However, the sensor electronics 12 (e.g., via processor module 214) may 31 be implemented to execute prospective algorithms used to generate transformed sensor data and/or displayable sensor information, including, for example, algorithms that: evaluate a clinical acceptability of reference and/or sensor data, evaluate calibration data for best calibration based on inclusion criteria, evaluate a quality of the calibration, compare estimated analyte values with time corresponding measured analyte values, analyze a variation of estimated analyte values, evaluate a stability of the sensor and/or sensor data, detect signal artifacts (noise), replace signal artifacts, determine a rate of change and/or trend of the sensor data, perform dynamic and intelligent analyte value estimation, perform diagnostics on the sensor and/or sensor data, set modes of operation, evaluate the data for aberrancies, and/or the like.

Although separate data storage and program memories are shown in FIG. 2B, a variety of configurations may be used as well. For example, one or more memories may be used to provide storage space to support data processing and storage requirements at sensor electronics 12.

In one preferred embodiment, the analyte sensor may be an implantable glucose sensor, such as described with reference to U.S. Pat. No. 6,001,067 and U.S. Patent Publication No. US-2005-0027463-A1. In another preferred embodiment, the analyte sensor may be a transcutaneous glucose sensor, such as described with reference to U.S. Patent Publication No. US-2006-0020187-A1. In still other embodiments, the sensor may be configured to be implanted in a host vessel or extracorporeally, such as is described in U.S. Patent Publication No. US-2007-0027385-A1, U.S. Patent Publication No. US-2008-0119703-A1 (now abandoned), U.S. Patent Publication No. US-2008-0108942 A1 (now abandoned) and U.S. Pat. No. 7,828,728. In one alternative embodiment, the continuous glucose sensor may include a transcutaneous sensor such as described in U.S. Pat. No. 6,565,509 to Say et al., for example. In another alternative embodiment, the continuous glucose sensor may include a subcutaneous sensor such as described with reference to U.S. Pat. No. 6,579,690 to Bonnecaze et al. or U.S. Pat. No. 6,484,046 to Say et al., for example. In another alternative embodiment, the continuous glucose sensor may include a refillable subcutaneous sensor such as described with reference to U.S. Pat. No. 6,512,939 to Colvin et al., for example. In another alternative embodiment, the continuous glucose sensor may include an intravascular sensor such as described with reference to U.S. Pat. No. 6,477,395 to Schulman et al., for example. In another alternative embodiment, the continuous glucose sensor may include an intravascular sensor such as described with reference to U.S. Pat. No. 6,424,847 to Mastrototaro et al.

Figure 2C:
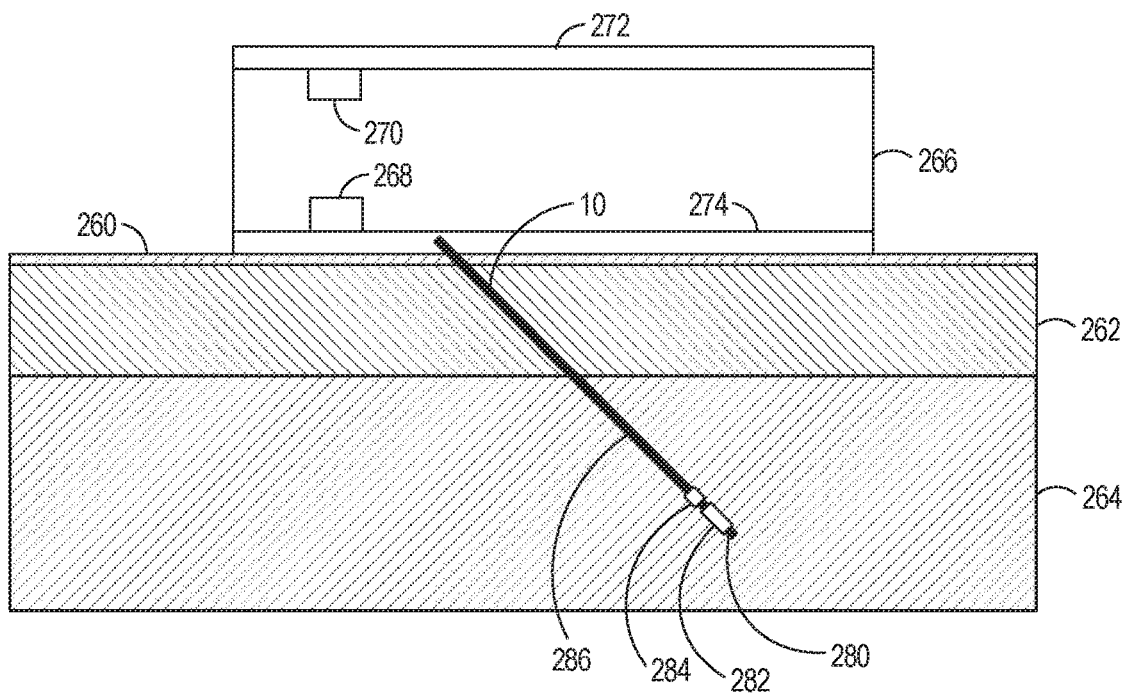
FIG. 2C is a schematic illustration of an example analyte sensor system engaged with tissue of a host.

FIG. 2C is a schematic illustration of an example analyte sensor system 8 that shows an analyte sensor 10 inserted into through the epidermis 260, dermis 262 and into a subcutaneous layer 264 so that a distal end 280 of the analyte sensor 10 is in the subcutaneous layer. In a human host, the epidermis layer 260 may typically be about 0.01 cm thick, the dermis layer 262 may typically be about 0.2 cm thick, and the subcutaneous layer may be substantially thicker, e.g., 1 cm to 1.5 cm. A working portion 282 (e.g., working electrode) of the analyte sensor 10 may be at or near the distal end 280 of the analyte sensor at a depth of about 0.5 cm. The working portion 282 may, for example, include a coating on a conductive portion 286 (e.g., conductive core). The working portion 282 may be configured, for example, to generate voltage that is proportional to a glucose concentration (e.g., the working portion may be part of a glucose sensor as is available from Dexcom, Inc.) In some examples, a temperature sensor 284 may be provided at or near the distal end 280 of the analyte sensor. The temperature sensor 284 may be used to compensate for temperature variations, using one or more of the various techniques described below. In addition, empirical measurements (discussed below and shown in FIG. 21) have shown that the conductance of an analyte sensor may depend strongly on temperature. In some examples, this relationship between conductance and temperature may be used to estimate a subcutaneous temperature, which may be used in a temperature compensation model or other method. In other examples, the relationship between conductance and temperature may be applied directly (e.g., without using an estimated temperature) to compensate for temperature variations.

The analyte sensor may be coupled to a base 274 that may be coupled to a housing 266. The housing may contain some or all of the components shown in FIG. 2A or the sensor electronics 12 shown in FIG. 2B.

In some examples, the housing may include a heat shield 272 on a top surface (and optionally additionally on one or more side surfaces) to reflect heat from the housing, which may, for example, reduce the impact of sunlight on the sensor 10.

In some examples, the sensor electronics 12 may include a first temperature sensor 268 near a bottom portion of the housing 266 and a second temperature sensor 270 near a top portion of the housing. A circuit such as processor 251 or processor module 214 may be configured to determine a compensated glucose concentration level based at least in part on the glucose signal, the first temperature signal, and the second temperature signal.

In some examples, a temperature gradient or heat flux may be determined (e.g., by processor 251 or processor module 214) from signals received from the first temperature sensor 268 and second temperature sensor 270. For example, if the housing is exposed to sunlight, the signal from the second temperature sensor 270 may indicate a higher temperature than the signal first temperature sensor 268. This information may, for example, be used to estimate a temperature at the analyte sensor 10 or may be used in a temperature compensation algorithm or model. In another example, the sensor may be exposed to a cold temperature, in which case the second temperature sensor 270 may show a lower temperature than the first temperature sensor. In another example, the system may be immersed in cold water, in which case the first temperature sensor 268 and second temperature sensor may initially show a gradient but quickly transition to approximately equal temperature values. This information may be used in temperature compensation directly, based upon relationships between one or more of the temperature sensors 268, 270 and a temperature at the analyte sensor 10, or the temperature information may be used indirectly as an indication of the environment of the analyte sensor or host (e.g., immersed in hot or cold water, exposed to cold air, exposed to sun) from which temperature or temperature compensation information may be inferred, or which may be applied to a model.

Figure 2D:
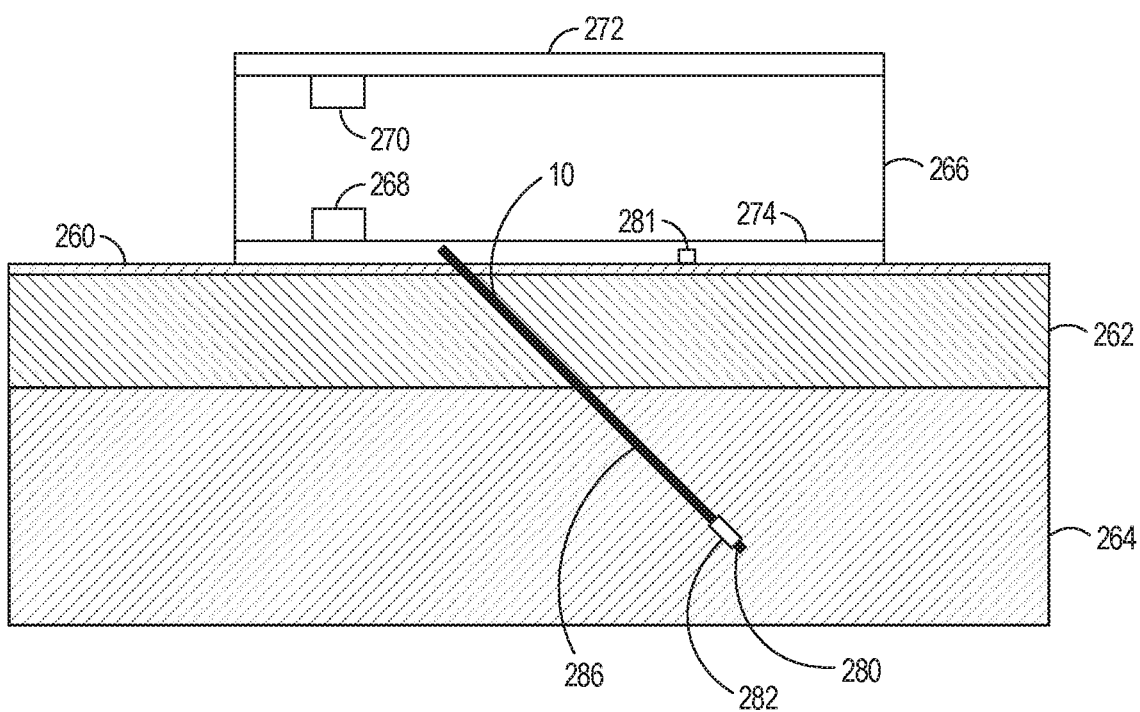
FIG. 2D is a schematic illustration of an example analyte sensor system engaged with tissue of a host.

FIG. 2D is a schematic illustration of another example configuration of the analyte sensor system 8 engaged with tissue of a host. In the example of FIG. 2D a temperature sensor 281 is positioned on the base 274 in contact with the epidermis 260 of the host's skin. For example, the temperature sensor 281 may be incorporated into an adhesive pad for securing the base 274 to the host's skin.

Figure 3:
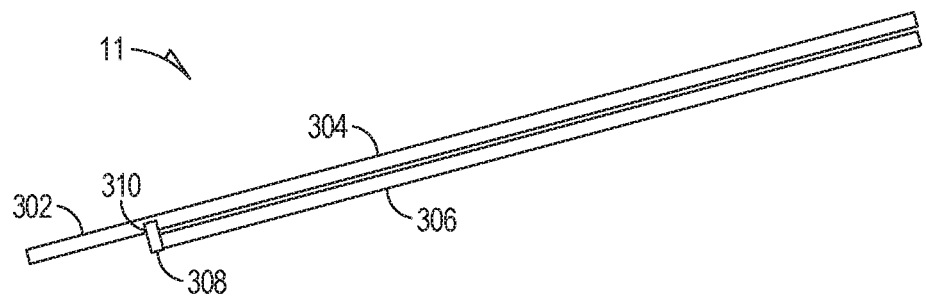
FIG. 3 is a schematic illustration of temperature sensor on a distal portion of an analyte sensor.

FIG. 3 is a schematic illustration of an example distal portion 11 of an analyte sensor 10 that may include an analyte sensor region 302 configured to generate a sensor signal indicative of a glucose concentration level of substance (e.g., interstation fluid) of a host. The signal may be conducted up one or more elongated members 304, 306 which may be wires, (e.g. platinum or tantalum or an alloy thereof). The sensor signal may be communicated to sensor electronics for processing. The analyte sensor 10 may also include a temperature sensor 308, which may be at or near the analyte sensor region 302. In an example, the temperature sensor 308 may, for example, be a thermocouple that may produce a voltage proportional to a temperature difference between a junction 310 of conductors 304, 306 and a second junction (not shown), which may be at a proximal end of the conductors (e.g., outside the host.) To form a working thermocouple, conductors 304, 306 may be formed of different materials. For example, one of conductors 304, 306 may be platinum and the other of the conductors 304, 306 may be tantalum. A signal generated by the thermocouple may be communicated to sensor electronics for processing (i.e., for use in compensating glucose sensor values for temperature.

In another example, the temperature sensor 308 may be a thermistor. A resistance value of the thermistor may be measured using conductors 304, 306 and communicated to sensor electronics for processing.

In an example, a sequential method may be used to measure a glucose concentration level and a temperature using a pair of conductors (e.g., a platinum conductor and a tantalum conductor as mentioned above, which may be 304, 306 in FIG. 3.) For example, an analyte concentration level may be measured by applying a voltage (e.g. 0.6 volts) across the conductors, and then a temperature measurement may be obtained by measuring an open circuit potential across the conductors, or by applying a low voltage input across the conductors and measuring a current (e.g. to determine a resistance of a thermistor and thereby determine a temperature parameter.)

In another example, a temperature sensor may be positioned at a proximal end of sensor wires, which may have a high thermal conductivity so that temperature measurements at the proximal end approximate the temperature near an analyte sensor (i.e., at a distal end). In various examples, such approximate temperature measurements may be used for temperature compensation.

Figure 4:
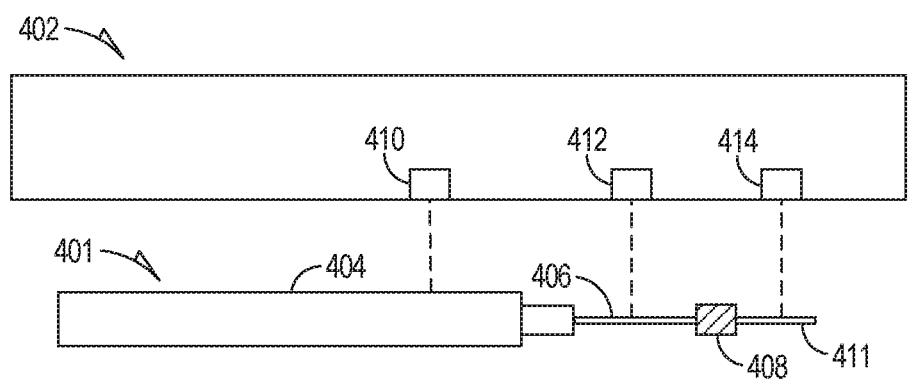
FIG. 4 is a schematic illustration of an example temperature sensor on a proximal portion of an analyte sensor.

FIG. 4 is a schematic illustration of an example proximal portion 401 of an analyte sensor 10 and an electrical contact portion 402, which may for example be a portion of sensor electronics or a transmitter (such as a transmitter produced by Dexcom and configured to couple with a base portion that includes a subcutaneous glucose sensor.) The proximal portion 402 of the analyte sensor may include a first conductor 404 and a second conductor 406, which may have distal ends (not shown) coupled to an analyte sensor (e.g., glucose sensor.) The electrical contact portion 404 may include a first contact 412 configured to contact with the first conductor 404 and a second contact configured to contact with the second conductor 406. The proximal portion may also include a thermistor 408 and a third conductor 411 coupled to the thermistor and configured to couple with a third contact 414 on the electrical contact portion. The temperature-sensitive resistance of the thermistor may be used to compensate for temperature effects on the glucose sensor.

Figure 5A:
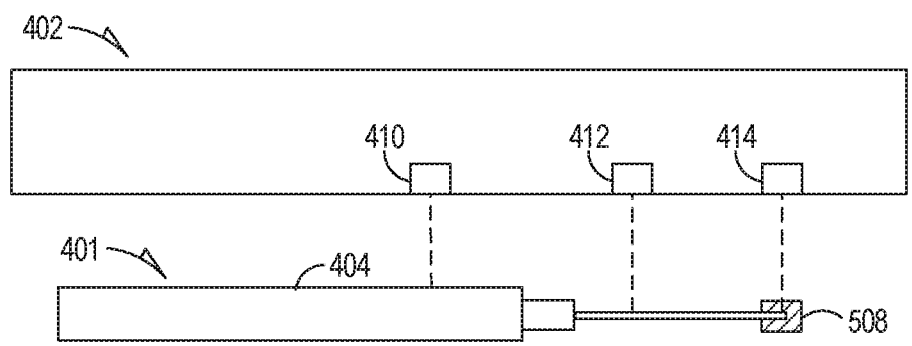
FIG. 5A is a schematic illustration of another example temperature sensor on a proximal portion of an analyte sensor.
Figure 5B:
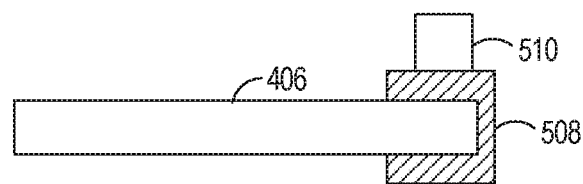
FIG. 5B is an enlarged view of a portion of the temperature sensor shown in FIG. 5A.

FIG. 5A is an illustration of a configuration similar to the construction of FIG. 4, but the thermistor of FIG. 4 has been replaced with a temperature-sensitive coating 508. FIG. 5B is an enlarged illustration of the temperature-sensitive coating 508, which may be on conductor 406. A conductive element 510 may be configured to couple with the coating, or connected to the coating, and configured to couple with the third contact 414, so that the resistance of the coating may be measured using by applying a voltage or driving a current across contacts 412, 414.

Overview of Example Temperature Compensation Methods

A system may compensate for the effects of temperature on an analyte sensor (e.g., glucose sensor), using a learned or defined relationship between inputs (e.g., a temperature sensor signal, or one or more other sensor signals) and analyte levels to provide estimated values (e.g., estimated glucose concentration values) that are less impacted by temperature variations. The relationship may, for example, be defined by a theoretical model, or determined from bench data, clinical trial data, or a combination thereof.

A variety of approaches and models or algorithms may be applied or combined to compensate for temperature signal variations caused by temperature changes. For example, a system may compensate for long-term trends or averages, or may compensate for short-term (e.g., real-time) changes, or a combination thereof.

In some examples, a linear relationship between temperature and glucose sensor signals may be determined and used to approximate the relationship between temperature and glucose sensor signal and compensate for temperature effects (e.g., Compensated Glucose Value=(Sensed Glucose Value)×Constant f(Tmeasured, Treference, Sensed Glucose Value.)

In some examples, a sensitivity (Mt) of a sensor to an analyte (glucose) concentration may be compensated for temperature effects by determining a compensated sensitivity value (Mt, comp) based on a programmed (e.g., factory-calibrated) sensitivity (Mt, pro) and a % sensitivity change per degree Celsius (Z). A temperature difference (Delta T) may be determined as a difference between a sensed or determined subcutaneous temperature (Tsubcu at time t) and a reference temperature (Tsubcu, reference), e.g., (Delta T=(Tsubcu at time t)−(Tsubcu, reference). The reference temperature (Tsubcu, reference) may for example be an average, or a predetermined subcutaneous temperature value. A compensated analyte sensitivity (Mt, comp) may be determined by solving an equation (Mt, comp−Mt, pro)/Mt, pro=Z*Delta T). The value for Z may be determined from bench testing for a particular sensor configuration. Solving the equation for Mt, comp yields a compensated analyte sensitivity, Mt, comp=Z*(Delta T)*(Mt, pro)+(Mt, pro). The compensated analyte sensitivity (Mt, comp) may be used to convert raw analyte sensor data into estimated glucose values, e.g., using an equation:

Estimated Glucose Value=Mt, comp*(Sensor value)+Offset. In some examples, the offset may be determined for a particular analyte sensor design configuration, as is routinely done with existing commercial sensors. In other examples, multiple blood glucose readings (or, in the case of other analytes, biological samples) may be obtained (e.g., via a user interface) and used to determine an Offset for a particular sensor.

In some examples, the temperature that is compared to a reference value is the long-term average temperature. In some examples, this is to account for body temperature differences among hosts (patients.) In other examples, real-time compensation for temperature may correct for temperature-based sensor variations that may be caused, for example, by exposure to hot water (e.g., a shower), cold water (e.g., swimming), air conditioning, sunlight, heat variations during sleep (e.g., contained heat due to warm blankets), or other hot or cold environments.) Some examples may combine long-term and real-time compensation methods.

In some examples, where a temperature sensor is not subcutaneous, a delay parameter may also be used (in combination with a linear model, or a more complex model as described below), to compensate for a delay between detection of a temperature change at a temperature sensor and an actual temperature change at an analyte sensor. Various example methods for determining a subcutaneous temperature based on a signal from a non-subcutaneous sensor are provided below.

Determining a Subcutaneous Temperature from a Non-Subcutaneous Temperature Sensor.

In some systems, devices, or methods, a subcutaneous temperature may be determined (e.g., estimated) using a temperature signal from a non-subcutaneous temperature sensor, such as temperature sensor in sensor electronics of an external device (e.g., transmitter) that may be coupled to a subcutaneous analyte (e.g., glucose) sensor. One or more of a variety of methods may be used to determine a subcutaneous temperature from a temperature signal received from a non-subcutaneous temperature sensor. In some examples, a linear relationship between non-subcutaneous and subcutaneous temperature values may be used to approximate a subcutaneous temperature. In some examples, a delay parameter may also be used (in combination with a linear model, or a more complex model as described below), to compensate for a delay between detection of a temperature change at a temperature sensor and an actual temperature change at an analyte sensor. In some examples, a non-linear relationship (e.g., quadratic equation or higher level polynomial or other relationship) may be determined and used to compensate for temperature, and may optionally include a delay parameter. In some examples, a relationship may be determined by solving a differential equation (e.g., a heat transfer relationship) to determine temperature compensation. For example, a sensor system may solve a differential equation each time an analyte value is needed (e.g., every 5 minutes or every 15 minutes) to provide a temperature-compensated analyte value. In another example, a filter or predetermined relationship based on a differential equation may be applied to compensate for temperature.

Linear Model Example

In some examples, a subcutaneous temperature may be determined from a non-subcutaneous temperature using a linear model. A linear model may, for example, be developed from a bioheat model (e.g., Pennes bioheat equation), known host tissue parameters (e.g., typical heat-transfer parameters for human skin and subcutaneous tissue), and sensor electronics (e.g., transmitter) parameters, which may be determined for example with bench testing. The tissue parameters may for example include thermal conductivity or heat flux across tissue.

A subcutaneous temperature (Tsubcu) may be determined from a measured non-subcutaneous temperature (Texternal) using a linear equation (e.g., Tsubcu=a*Texternal+b), where the gain/slope (a) and offset (b) may be determined for example using empirical data, theoretical or model data, or a combination thereof.

In some examples, when an analyte temperature sensitivity is well known, the gain (a) and offset (b) for the above equation may be determined or updated based upon an analyte calibration value (e.g., blood glucose value): In other words, if confidence in glucose sensitivity is high, a temperature may be estimated based upon a blood glucose value from a finger-stick and a signal received from a glucose sensor. A system may calculate the real analyte sensitivity from using the entered glucose value, then determine a subcutaneous temperature from the real analyte sensitivity, and then determine a relationship (e.g., value of gain and offset) between the subcutaneous temperature and a signal from a non-subcutaneous temperature sensor. The system may determine or receive a temperature sensor value (e.g., from a temperature sensor in external sensor electronics) at the time of calibration to assure that an updated temperature sensor signal is used in determining the sensitivity, gain and offset. In some examples, rather than using the new gain and offset, a weighted average or probabilistic model may be used so that the gain and offset are not overly influenced by independent factors that may change the sensitivity, such as a period of inaccuracy after initial placement of a sensor (e.g., a "dip and recover" phenomenon where sensor signal generates low sensor signals (dip) during an initial "warm-up" period followed by more accurate (recovered) readings after warm-up).

Delay Between Non-Subcutaneous Sensor Detection and Subcutaneous Temperature Change In some examples, a system may account for a delay between the time a temperature change is registered at a non-subcutaneous temperature sensor and the time a temperature change actually occurs at a subcutaneous analyte (glucose) sensor: If an analyte sensing system includes a subcutaneous temperature sensor, a direct subcutaneous temperature measurement may be used for temperature compensation, but if the system relies on a non-subcutaneous (e.g., external) temperature sensor, the accuracy of a temperature compensation method may be improved by accounting for delayed temperature change at the subcutaneous glucose sensor.

For example, the linear model described above assumes that the subcutaneous temperature matches the external temperature (e.g., sensor electronics or transmitter temperature), but the skin tissue warms and cools much more slowly than the transmitter does, so there is a delay between the time an external sensor registers a temperature change and the time a change occurs at a subcutaneous location. For example, if a person walks from a cold air-conditioned room to a warmer location, the external sensor will register a temperature change rapidly, but the subcutaneous temperature will take much longer to warm up. In another example, when a host and sensor are immersed in cold water (e.g., in a pool, ocean, or lake having a temperature lower than an ambient temperature), a drop in temperature will be detected first in a sensor in external sensor electronic (e.g., in a CGM transmitter), and some time later the temperature at a subcutaneous sensor will drop, due to heat loss through the sensor or through tissue of the host. The accuracy of the subcutaneous temperature estimation may be improved by building in a delay to reflect this reality.

In some examples, the delay may account for a delay in registration of a temperature change in the non-subcutaneous temperature sensor, based upon other temperature information, or a model or estimate of the time delay for the non-subcutaneous sensor to register the temperature change. For example, when an environmental temperature change occurs, it may take a relatively short period of time (e.g., 1 minute) for the non-subcutaneous temperature sensor to register the change, especially if the sensor is embedded in a sensor electronics housing through which heat must conduct to register the temperature change. Some time later (e.g., 6 minutes), the subcutaneous temperature change may be observed), and the net delay is the difference between the two readings (e.g., 5 minutes).

In some examples, a constant delay may be used. For example, a temperature compensation method may assume a delay time period (d) and compensate for a temperature effect using a temperature from a prior time period based on the assumed delay (e.g., use temp at time t−d). In other examples, compensation may be made using both a temperature at a current time (t) and a temperature from a prior time period based on the assumed delay (e.g., use temp at time t−d). In yet other examples, compensation may be made using a plurality of temperature measurements from different time periods associated with assumed delay (e.g., use both temp at $t-d_1$ and temp at $t-d_2$. In some examples, the delay may, for example, be from 30 seconds to 4 minutes (e.g., 1 minute), from 1 minute to 10 minutes (e.g., 5 minutes), from 5 minutes to 15 minutes (e.g., 10 minutes), or from 20 minutes to an hour (e.g., 30 minutes). In some examples, the delay may be determined based upon information known about the host, such as average body temperature or body mass index.

In some examples, a variable delay time period may be used. In some examples, the variable delay period may, for example, be based at least in part upon a variation between a detected temperature and a baseline. In another example, the delay may be based at least in part on a difference or rate of change of detected temperature and a previous detected temperature (e.g., a longer delay may be used when a larger temperature change is observed because the heat transfer process will take longer to complete to bring the subcutaneous temperature up to a steady state). In some examples, a delay may be implemented only when a temperature change satisfies a condition, for example, when a sudden temperature change in excess of a threshold occurs (e.g., a change larger than 5° C., or 10° C.)

In some examples, the variable delay may be based upon a temperature gradient, e.g., a difference between a sensed temperature and a determined subcutaneous temperature. In some examples, the variable delay may be based upon a heat transfer equation or model that may account, for example, for temperature gradients (e.g., between ambient and subcutaneous temperatures) and one or more rates of heat transfer, and may optionally also account for biological processes (e.g., heat transfer via blood flow).

A delay may be computed or used in various other example methods (e.g., partial differential equation model, polynomial models, state models, time series models, models with sub-groups or conditions).

Figure 6:
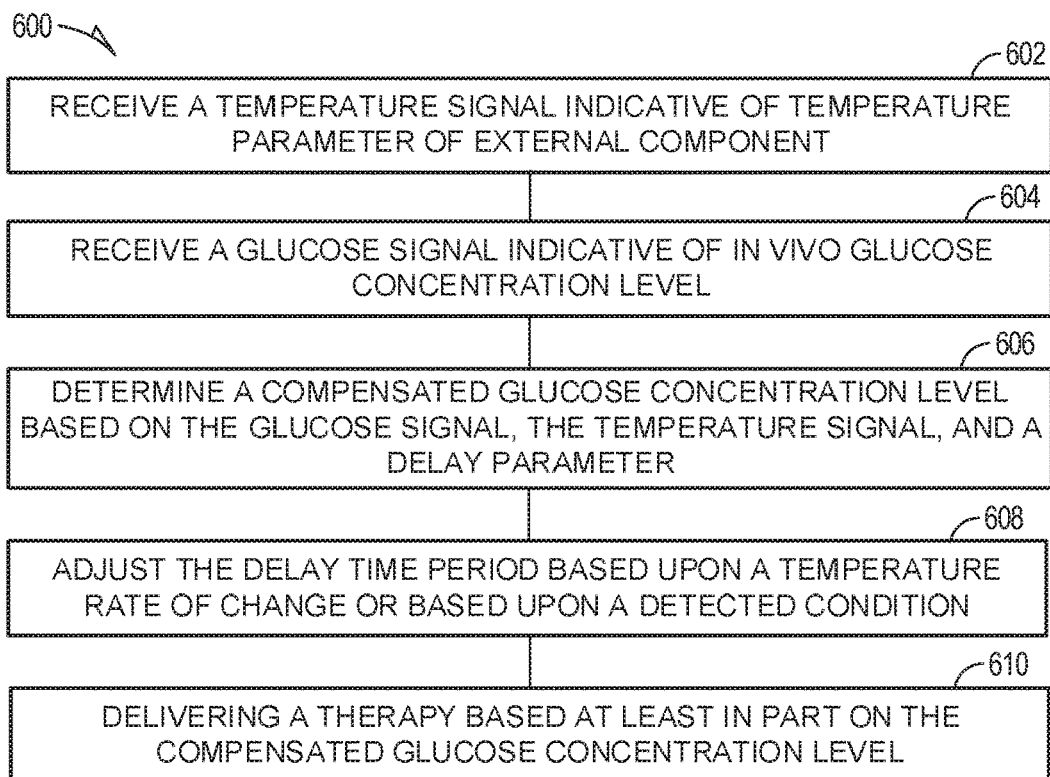
FIG. 6 is a flowchart illustration of an example method of determining a temperature-compensated glucose concentration level using a delay parameter.

FIG. 6 is a flowchart illustration of an example method 600 of determining a temperature-compensated glucose concentration level using a delay parameter. The method 600 may include at 602 receiving a temperature signal indicative of a temperature parameter of an external component. The temperature parameter may for example be a temperature, a temperature change, or a temperature offset. Detecting a temperature signal may include, for example, measuring a temperature parameter of a component of a wearable glucose sensor. The method 600 may include at 604 receiving a glucose signal indicative of an in vivo glucose concentration level. Receiving a glucose signal may include, for example, receiving a glucose signal from a wearable glucose sensor.

The method 600 may include at 606 determining a compensated glucose concentration level based on the glucose signal, the temperature signal, and a delay parameter. In some examples, a temperature compensated sensor sensitivity value may be determined based on the temperature signal and the delay parameter, and an estimated glucose concentration value may be determined using the sensor sensitivity value and the glucose signal. In some examples, a model or neural network may be used to determine an estimated glucose concentration level based (at least in part) on the glucose signal, the temperature and the delay parameter.

In various examples, the delay parameter may be constant, or may be variable based on temperature or information about the host or other factors, as described above. In some examples, the temperature parameter may be detected at a first time and the glucose concentration level may be detected at a second time after the first time. The delay parameter may include a delay time period between the first time and the second time that accounts for a delay between a first temperature change at the external component and a second temperature change proximate a glucose sensor. In some examples, determining a compensated glucose concentration level may include executing instructions on a processor to receive the glucose signal and the temperature signal and determine the compensated glucose concentration level using the glucose signal, the temperature signal, and the delay parameter. The method may also include storing a value corresponding to the temperature parameter in a memory circuit and retrieving the stored value from the memory circuit for use in determining the compensated glucose concentration level. In some examples, the temperature-compensated glucose concentration level, an estimated subcutaneous temperature, or a delay parameter (or any combination thereof) may be determined using a linear model (e.g., linear equation), a nonlinear model, a partial differential equation model, a time series model, a linear or non-linear model with subgroups, or any other technique described herein.

The method may further include at 608 adjusting the delay time period based upon a temperature rate of change, or temperature gradient (or other factor or technique as described above) or based upon a detected condition. In some examples, the detected condition may include a sudden change in temperature, a location, or an exercise state or session (e.g., using an accelerometer).

Optionally, the method may further include at 610 delivering a therapy based at least in part on the compensated glucose concentration level.

Partial Differential Equation (PDE) Model Example

In some examples, a subcutaneous temperature may be determined from a non-subcutaneous temperature sensor signal using a partial differential equation (PDE) model. A PDE approach to temperature compensation may make the system more accurate, for example by accounting for the fact that the rate of change of temperature in external electronics (e.g., a CGM transmitter) is higher than the rate of change of temperature of subcutaneous tissue or fluids. The temperature of subcutaneous tissue and fluids may change more slowly in part because the body acts as heat sink. The use of a PDE model may be particularly advantageous in instances of rapid temperature change.

In an example, sensor electronics, a subcutaneous sensor, and skin layers may be treated as a multi-layer model. A sensor and skin layers (epidermis 260, dermis 262, and subcutaneous tissue 264) are shown in FIG. 2C. In an example, the multilayer structure may be deemed a one-dimensional (ID) system, where the 1D space is depth relative to the skin surface.

The distribution of temperature in space and time can be described by a heat equation:

$$\rho \bar{c} \frac{\partial u}{\partial t} = \nabla \cdot (K \nabla u) + m_b c_b (u_b - u) + S(u - u_a) \quad \text{(Equation 1)}$$

The variables and parameters in Equation (1) are defined as follows in Table 1.

TABLE 1

| Variable | Physical Meaning | Example Values |
| --- | --- | --- |
| u | Temperature as function of x and t | To be solved, u(x, t) |
| ρ | Tissue density | 1.05 g/cm$^3$ |
| c̄ | Specific heat of tissue | 0.83 cal/g = 3.47 J/g |
| K | Thermal conductivity | Different constant value for each layer |
| S | Rate of metabolic heat generation | 0.018 cal/min/° C./cm$^3$ = 1254.6 J/sec/K/m$^3$ |
| m$_b$ | Mass blood flow | m$_b$c$_b$ = 0.018 cal/min/ |
| c$_b$ | Specific heat of blood | ° C./cm$^3$ = 1254.6 J/sec/K/m$^3$ |
| u$_b$ | Core body temperature | 37° C. |
| u$_a$ | Ambient temperature | 30° C. (or as determined by sensor) |

The thermal conductivity for each layer in the 1D model can be determined or estimated. For example, the thermal conductivity for each skin layer may be determined by empirical or theoretical methods. The thermal conductivity of sensor electronics (including battery and epoxy adhesive) may be also determined. Example values are provided in Table 2:

TABLE 2

| Notation | Layer | Thickness | Depth Interval | K Thermal Conductivity | K in IS Unit |
| --- | --- | --- | --- | --- | --- |
| K$_{Tx}$ | Electronics | 0.4 cm | −0.4 cm~ 0 cm | 0.0571 cal/min/° C./cm | 0.400 J/sec/K/m |
| K$_{epi}$ | Epidermis | 0.01 cm | 0 cm~ 0.01 cm | 0.0336 cal/min/° C./cm | 0.235 J/sec/K/m |
| K$_{derm}$ | Dermis | 0.2 cm | 0.01 cm~ 0.21 cm | 0.0571 cal/min/° C./cm | 0.400 J/sec/K/m |
| K$_{subq}$ | Subcutaneous | 1.29 cm | 0.21 cm~ 1.5 cm | 0.0257 cal/min/° C./cm | 0.180 J/sec/K/m |

The outer boundary condition (BC) of this PDE is set to be the time-varying temperature as measured by the non-subcutaneous temperature sensor, and the inner BC is set to be the constant core body temperature.

Based on these assumptions, Equation 1 can be solved, so that a temperature at the sensor (e.g., at a working electrode) may be estimated. In some examples, the equation may be solved each time a temperature value is needed. In some values, a lookup table may be developed by solving the PDE across a range of plausible values, and the lookup table may be consulted to determine an approximate subcutaneous temperature. In some examples, a linear correlation between the temperature at the subcutaneous sensor and the temperature of an external sensor may be determined from a PDE model. In some examples, a PDE model may be used to perform temporospatial filtering to capture the transient process of temperature changes and time lags.

The estimated temperature at the subcutaneous sensor may be used to correct for sensitivity changes in the subcutaneous sensor. In an example, the temperature at the electrochemically reactive surface of an analyte sensor (e.g. glucose sensor) may be estimated and used to determine an estimated sensitivity of the electrochemical sensor at the estimated temperature.

Time Series Model Example

In some examples, a time series model may be used to estimate a subcutaneous temperature using a signal from a non-subcutaneous temperature sensor, or to compensate for temperature effects on analyte sensor sensitivity. In some examples, a temperature-compensated sensitivity may be determined directly, i.e. without estimating a subcutaneous temperature.

In an example, a $4^{th}$-order polynomial may be used as a model. For example, the following model may be used:

$$y = \frac{m_t^{point\_wise} - m_t^{factory\_cal}}{m_t^{factory\_cal}} \times 100 = p_1 x^4 + p_2 x^3 + p_3 x^2 + p_2 x^1 + p_5 x^0$$

where, $p_i$ (i=1, . . . , 5): Model parameters y: Sensitivity error $m_t^{point\_wise}$: Point wise sensitivity at time t calculated from glucose meter data (e.g., finger sticks)

$m_t^{factory\_cal}$: Point wise sensitivity at time t calculated from factory calibrated algorithm x: Measured temperatures Model parameters may be determined from an empirical data set, for example using a curve-fitting or optimization technique.

After the model parameters have been determined, the model may be used to compensate for temperature variations. For examples, the compensated sensitivity may be determined using the following equation:

$$m_t^{Compensated} = m_t^{factory\_cal} \left( \frac{p_1 x^4 + p_2 x^3 + p_3 x^2 + p_2 x^1 + p_5 x^0}{100} + 1 \right)$$

In some examples, the model parameters may be updated when a calibration entry (e.g., based on blood glucose meter data) is available. For example, the time series model may be converted to a recursive version of the model, so the model can be updated in real time when a finger stick measurement is available. The value for the constants may be determined based on population data, patient-specific data. The values may, for example, be as follows: $p_1$: −0.0004334, $p_2$: 0.04955, $p_3$: −2.035, $p_4$: 36.7 $p_5$: −259.7

While a $4^{th}$ order polynomial has been provided as an example, a $3^{rd}$ order or $5^{th}$ or higher order polynomial may also be used. Higher order polynomials may provide higher accuracy in compensation, but may require more time, input data, or processing power to determine and update model parameters.

Temperature Compensation Examples

An algorithm or model may be used to determine temperature-compensated analyte sensor values (e.g., glucose concentration level). In some examples, a neural network, state model (e.g., hidden Markov), probabilistic model, or other model may be used to develop a temperature compensation model. A model may, for example, be learned for a particular subject (e.g., patient) based upon data from the subject, and the model may be used to determine compensated estimated glucose concentration levels. In some examples, a model may be learned from a data from a population of patients (e.g., clinical trial data), and the model may be used for a population of patients. In some examples, the same model may be used for most or all patients (subject to exclusion criteria.) In some examples, a patient may be matched to a model that was developed from a population of similar patients (e.g., based upon average temperature, age, sex, BMI, or other factors.) Inputs to a model may include temperature measurements, time, sensor sensitivity, estimated glucose values, insulin sensitivity, accelerometer data (e.g., to detect activity or posture), heart rate, respiration rate, meal status, size, or type, insulin on board or insulin delivery amounts or patterns, body mass index (BMI), or other factors. An output from the model may include a sensor sensitivity, a local glucose level, a compartment bias value, a nonenzyme bias level (any of which may be combined to determine a glucose concentration level), or the model may output a compensated glucose/analyte concentration level. A model-based approach may be particularly effective because the various temperature effects (e.g., sensor sensitivity, a local glucose level, a compartment bias value, a nonenzyme bias level) may be linear, nonlinear, or dynamic (e.g., dependent on a combination of both time and temperature).

Long-Term Average Methods

A temperature compensation system may account for a long-term average temperature average or trends. For example, a long-term average may be used to compensate for temperature variations. A long-term average may, for example, account for body or skin temperature variation between a host and a reference value. In some examples, a long-term average method may be used in combination with one or more of the short-term (e.g., real-time) temperature compensation methods described below.

The average subcutaneous temperature for an individual may be determined and updated in a number of different ways. For example, a subcutaneous temperature may be determined as an average (e.g., mean or median) over an entire sensor session, or an average of a rolling window (e.g. last 12 hours or 24 hours). In some examples, the subcutaneous temperature may be updated at an interval, e.g. remeasured or updated every 6, 9, 12, 18, or 24 hours. In some examples, the subcutaneous temperature may be determined as a weighted average, with more recent values (e.g. previous 6 hours, 12 hours, or 24 hours) being weighted more heavily and past intervals being weighted less heavily.

In an example, a temperature sensor may initially be calibrated for an initial reference value (e.g., 35° C.), which may represent an average temperature for a population. During a learning period, a temperature sensor may determine an actual temperature of the host. The learning period may be selected to be long enough (e.g., 6-12 hours) to screen out temperature excursions (e.g., so that the average is not determined during a heat/cold event such as a shower.) The learned average may be used to compensate for temperature of the host being different than a population average. For example, if a population were assumed to have an operational temperature of 35.0° C. but detected temperature from a particular host showed on average a temperature of 35.5° C., the half-degree variation may be used to compensate analyte values. In some examples, an initial average may be determined (e.g., on a first day) and a working average may be updated with subsequent temperature measurements (e.g., using average temperatures on a second day, or over a two-day period.) Other time windows can also be used, as described above.

If a system has a subcutaneous temperature sensor, a series of temperature measurements may be obtained from the subcutaneous temperature sensor and used to determine a long-term average. In other examples, a subcutaneous temperature may be determined based on a sensed non-subcutaneous temperature using one of a variety of methods described below (e.g., based on a linear or higher-level relationship). After the subcutaneous temperature for an individual (Tsubcu, ind) is established, a temperature-corrected analyte sensitivity may be determined based on a deviation from a reference temperature (Tsubcu, reference), for example using the equations provided above.

Glucose Rate of Change

In some examples, the rate of change of estimated glucose values or the rate of change of a signal from a glucose sensor may be used as an input for determining temperature compensation. For example, when the rate of change satisfies a condition (e.g., exceeds a specified value), temperature compensation may be suspended, or temperature compensation may be shifted to a different model. For some subcutaneous glucose sensors, glucose concentration levels determined from the subcutaneous sensor reflect a time lag relative to blood glucose levels, because of a physiological delay in changes in glucose levels in interstitial fluid compared to changes in blood (e.g., it can take up to several minutes for a change in blood glucose level to be reflected in interstitial fluid measured by a subcutaneous glucose sensor.) Delays may also be introduced by periodicity of sensor readings (e.g., if a sensor reading is taken every 5 minutes, the estimated glucose level could be 4+ minutes old at certain points in the cycle.) When a time lag error that is present in the system during times of fast glucose change, temperature compensation may be performed on inaccurate (out-of-date) estimates of glucose: In some instances, temperature compensation on an out-of-date glucose level could make the estimate worse, so it may be useful to suspend or change temperature compensation during periods of high rate of change. For example, when a glucose concentration level is dropping rapidly (e.g., due to vigorous exercise), an estimate from a subcutaneous temperature sensor may be "behind" the blood glucose concentration level (e.g., as determined from a blood glucose meter), so the subcutaneous sensor will show a higher estimated glucose concentration level than the blood glucose level. If temperature compensation raises the estimated blood glucose concentration level of the subcutaneous sensor, it may exacerbate this discrepancy. This may be avoided by suspension of temperature compensation or shifting to a different model. In some examples, when a high rate of change condition is satisfied, temperature compensation may be applied only when the temperature compensation increases the rate-of-change (e.g., to avoid exacerbation of discrepancies caused by physiologic delays.)

In some examples, deviations in the output of an analyte sensor relative to the output of temperature sensor may be used to evaluate a signal from a temperature sensor. These correlations or deviations may be used to establish confidence in the temperature signal, the analyte sensor signal, or both. During times when glucose levels satisfy a stability condition, temperature and glucose concentration levels may be expected to exhibit correlations. A stability condition may, for example, be determined based on rate of change of a glucose concentration level. In some examples, a stability condition may include multiple sub-conditions, such as a short-term condition and long-term condition. For example, a glucose level may be deemed as stable when a rate of change, and/or average rate of change over a specified period of time satisfies a condition (e.g., not increasing or decreasing more than 1 mg/dL per minute, and/or not increasing or decreasing more than 15 mg/dL in 15 minutes). A glucose level may be deemed moderately stable (e.g., increasing or decreasing at a moderate rate, be indicated) when a rate of change and/or average rate of change or a specified period of time satisfies a condition (e.g., glucose level rising (or falling) 1-2 mg/dL per minute and/or rising (or falling) 15-30 mg/dL in 15 minutes.

Figure 15A:
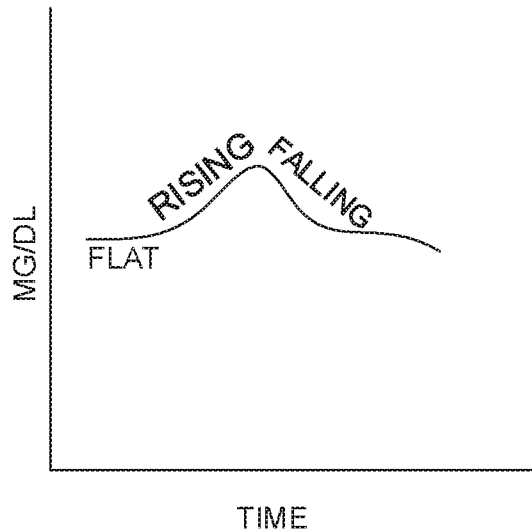
FIG. 15A shows output of a glucose sensor plotted against time.
Figure 15B:
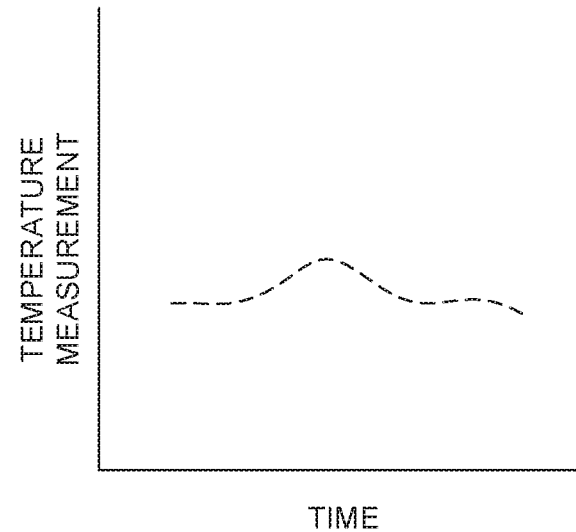
FIG. 15B shows output of a temperature sensor plotted against time.
Figure 15C:
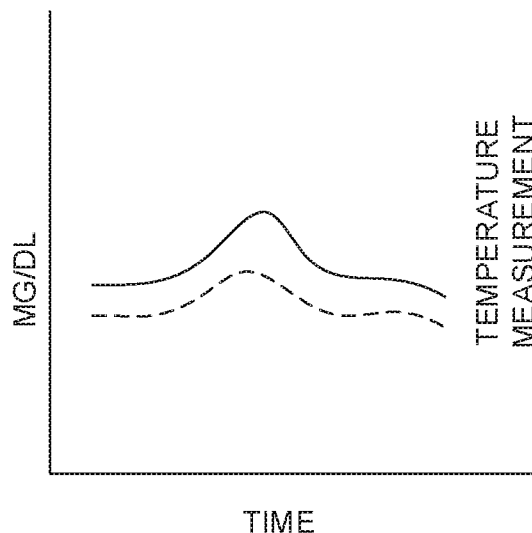
FIG. 15C shows the temperature overlaid onto glucose sensor output, where a correlation is apparent.
Figure 15D:
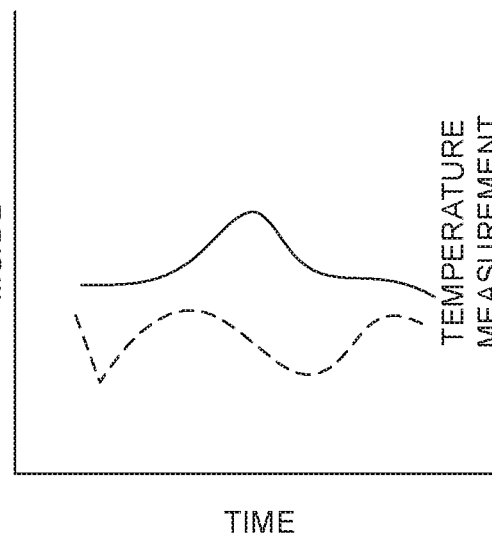
FIG. 15D shows the temperature overlaid onto glucose sensor output, where a correlation is not apparent.

As illustrated in FIGS. 15A-15C, the slope of a temperature curve and glucose curve should be correlated when glucose levels are stable (or, in some examples, moderately stable), because the changes in the glucose curve reflect temperature-generated variations in the output of the analyte sensor. FIG. 15A shows output of a glucose sensor plotted against time. The gain on mg/dL is relatively high to show variations in slope in a time period of relative glucose stability. FIG. 15B shows output of a temperature sensor plotted against time. FIG. 15C shows the temperature overlaid onto glucose sensor output (i.e., FIG. 15B combined with FIG. 15A.) The analyte sensor output correlates with the temperature sensor output: The analyte sensor has rising values (positive slope) when the temperature sensor is rising, the analyte sensor has falling values (negative slope) when the temperature sensor output is falling, and the analyte sensor values are flat when the temperature sensor output is flat. Confidence in the temperature signal may be inferred from this correlation. In contrast, FIG. 15D shows an example where the temperature sensor output (dotted line) does not correlate well with the glucose sensor output during a time of relatively stable glucose values, suggesting that the temperature sensor output may not be reliable.

In various examples, when confidence in a temperature sensor output is low, temperature compensation may be suspended, reduced, or modified, or other information (e.g., detection of exercise as described below) may be used or solicited to increase the accuracy of temperature compensation.

Figure 7:
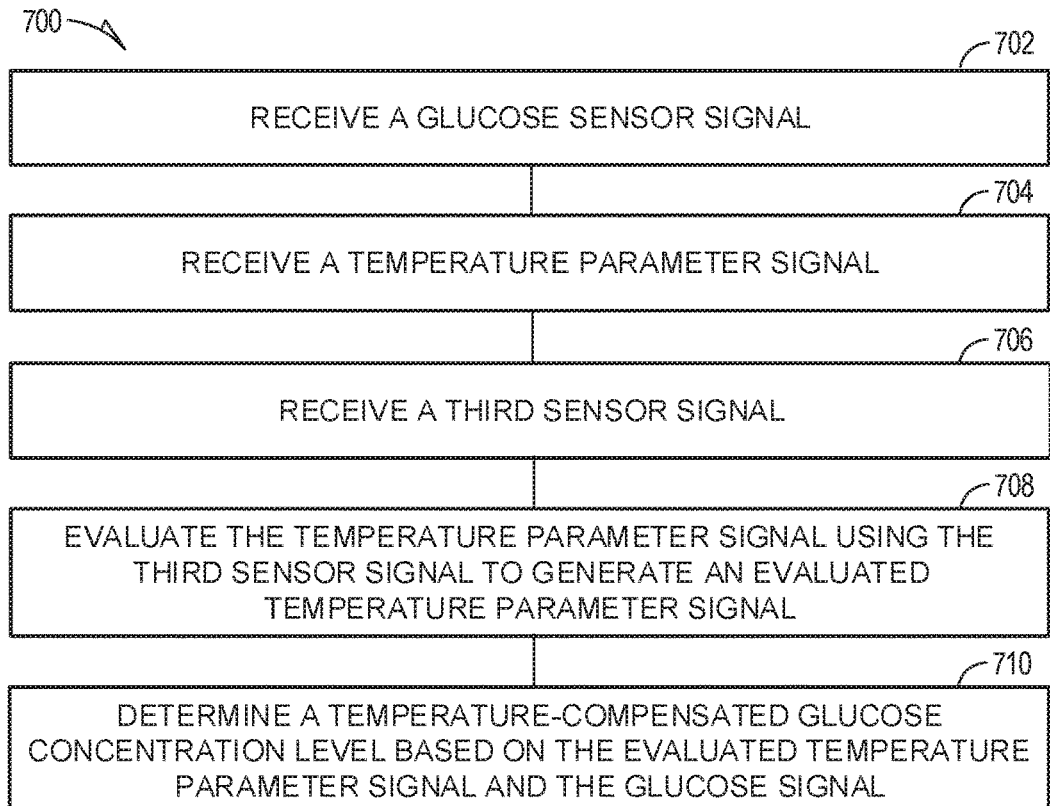
FIG. 7 is a flowchart illustration of an example method of determining a temperature-compensated glucose concentration level based upon an evaluated (e.g., corroborated) temperature value.

FIG. 7 is a flowchart illustration of an example method 700 of determining a temperature-compensated glucose concentration level based upon an evaluated (e.g., corroborated) temperature value. The method 700 may include at 702 receiving a glucose sensor signal. For example, a glucose sensor signal may be received from a continuous glucose monitor (CGM.)

The method 700 may include at 704 receiving a temperature parameter signal. Receiving a temperature parameter signal may, for example, include receiving a signal indicative of a temperature, a temperature change, or a temperature offset.

The method 700 may include at 706 receiving a third sensor signal. Receiving a third sensor signal may include, for example, receiving a heart rate signal, receiving a pressure signal, receiving an activity signal or accelerometer signal (e.g., to detect exercise), or receiving a location signal (e.g., to infer proximity to a hot or cold environment such as a pool, beach, or air-conditioned facility.) In some examples, receiving the third sensor signal may include receiving temperature information from an ambient temperature sensor. In some examples, receiving the third sensor signal may include receiving information from a wearable device, such as a watch. In some examples, receiving the third sensor signal may include receiving temperature information from a physiologic temperature sensor, which may for example be integrated into a watch or other wearable device. In some examples, the third signal may include a heart rate signal, respiration signal, pressure signal, or activity signal, and an exercise state may be detected from a rise in the heart rate signal, respiration signal, pressure signal, or activity signal.

The method 700 may include at 708 evaluating the temperature parameter signal using the third sensor signal to generate an evaluated temperature parameter signal. In some examples, evaluating the temperature parameter signal may include determining a presence at a location having a known temperature characteristic. For example, a low or high temperature signal may be corroborated by a location signal that indicates a presence at location having a known ambient temperature characteristic (e.g., a hot or cold environment) such as a pool, beach, air-conditioned facility or area with a known weather characteristic, which may be determined for example by reference to a network resource (e.g., website) or stored look-up table. In some examples, the method may include determining a presence at a location having an immersive water environment, such as a pool or beach. In some examples, evaluating the temperature parameter signal may include determining that a change in temperature parameter signal is consistent with an exercise session. For example, evaluating the temperature parameter signal may include determining that the temperature parameter signal is consistent with an occurrence of an elevated body temperature due to exercise.

The method 700 may include at 710 determining a temperature-compensated glucose concentration level based on the evaluated temperature parameter signal and the glucose sensor signal. In some examples, determining a temperature-compensated glucose concentration level may include applying the temperature parameter signal to an exercise model. In some examples, the method may include using an exercise model (e.g., outdoor or convectively cooled exercise model) when exercise is detected and a change in the temperature parameter signal indicates a reduction in temperature. For example, temperature compensation based on an non-subcutaneous temperature sensor (e.g., in sensor electronics) may be suspended when a detected temperature goes down, but exercise is detected (e.g., when HR or activity goes up), because during an exercise session the subcutaneous temperature may be stable, or even go up, when a patient conducts vigorous exercise (e.g., running) outside in a cooled environment (e.g., when convectively cooled by a fan, or when exercising outdoors in a cold weather environment).

Figure 8:
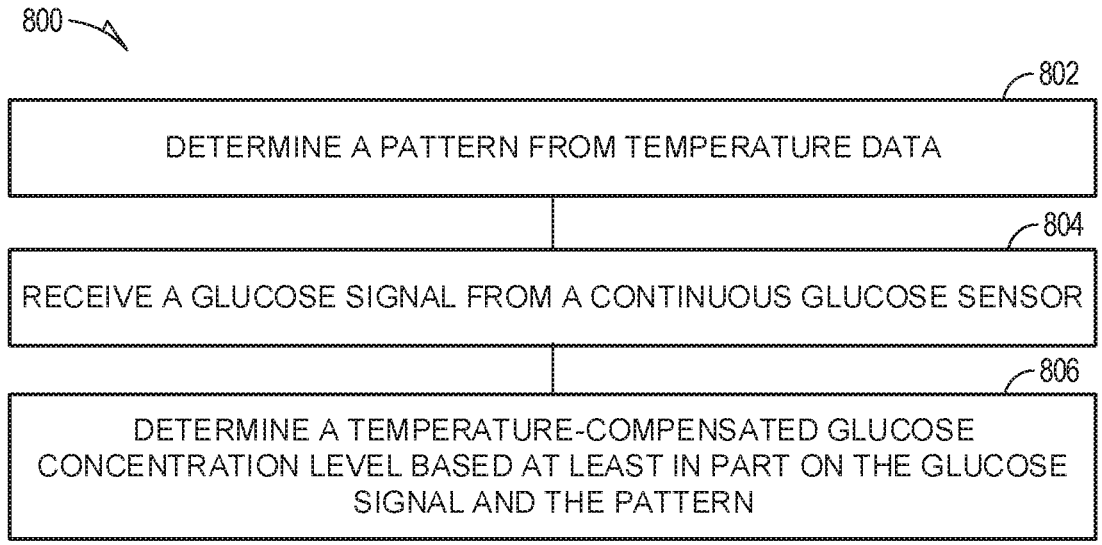
FIG. 8 is a schematic illustration of an example method for temperature-compensating a continuous glucose sensor that includes determining a pattern from temperature information.

FIG. 8 is a schematic illustration of an example method 800 for temperature-compensating a continuous glucose sensor that includes determining a pattern from temperature information. The method 800 may include at 802 determining a pattern from temperature data. In some examples, determining a pattern may include determining a pattern of temperature variations, and the method may include compensating the glucose concentration level according to the pattern.

The method 800 may include at 804 receiving a glucose signal from a continuous glucose sensor, the glucose signal indicative of a glucose concentration level.

The method 800 may include at 806 determining a temperature-compensated glucose concentration level based at least in part on the glucose signal and the pattern. For example, the method may include receiving a temperature parameter, comparing the temperature parameter to the pattern, and determining the temperature-compensated glucose concentration level based at least in part on the comparison. In some examples, the pattern may include a temperature pattern correlated to a physiological cycle, such as a circadian rhythm. In some examples, the method 800 may include determining whether the temperature parameter is reliable based on the comparison to the pattern and using the temperature parameter to temperature-compensate the glucose concentration level when the temperature parameter is determined to be reliable.

In some examples, a degree of compensation may be determined based at least in part on the comparison of the temperature parameter to the pattern. For example, the degree of compensation may be based on defined ranges or confidence intervals.

In some examples, a pattern may be determined by determining a state, and determining a temperature-compensated glucose concentration level may be based at least in part on the determined state. For example, the method 800 may further include receiving a temperature parameter and determining a state may include applying the temperature parameter to a state model. In some examples, determining a state may include applying one or more of a glucose concentration level, carbohydrate sensitivity, time, activity, heart rate, respiration rate, posture, insulin delivery, meal time, or meal size to a state model. In some examples, determining a state may include determining an exercise state, the method may include adjusting a temperature compensation based model upon the exercise state.

Conditional Temperature Compensation

In some examples, a model may be selected or modified based upon a detected condition. For example, a group of different linear models may be developed, and a model may be selected from the group based upon a detected condition. In some examples, a condition may be determined using a state model.

In some examples, the condition may include a location or geographic characteristic. The location may for example include a geographic location parameter (e.g., longitude, latitude, or altitude), or a city or place or point of interest (e.g., beach or mountain). In various examples, location information, geographic information, or physiologic sensor information (e.g., activity or heart rate as described below) may be collected from a patient's smart device such as cellular phone, watch, or other wearable sensor.

In some examples, the condition may include the deviation of a temperature reading from an average. For example, a rolling mean temperature value and rolling standard deviation may be determined from a sequence of temperature values, and a model (e.g., a linear model) may be used depending on whether the temperature is $+1\sigma$ away from the mean, $-1\sigma$, $+2\sigma$, $-2\sigma$, $+3\sigma$, $-3\sigma$. In some examples, the rolling mean may be determined from a predetermined number of previous temperature values. In various examples, a current reading may be included, or excluded from the rolling mean. In some examples, the rolling mean may be exponentially weighted.

In some examples, the condition may include a patient demographic. For example, the demographic may include sex (e.g., use a different model for male vs. female host/patient), diagnosis (e.g., Type 1 diabetic or Type 2 diabetic or nondiabetic), age (e.g., age in years, or youth, adolescent, adult, elderly), biological cycle (e.g., circadian rhythm or menstrual cycle), medical condition (e.g., pregnancy or health/sickness or chronic illness).

In some examples, the condition may be determined from a wearable sensor or physiologic sensor, such as a heart rate sensor, accelerometer, pressure gauge, or temperature sensor. The condition may include a state determined based upon one or more sensor inputs. In some examples, the condition may include an activity condition, which may be determined for example from heart rate or an accelerometer. In some examples, the condition may include a wake-sleep condition, which may be determined from one or more physiologic sensors (e.g., based on biorhythms) or from a posture sensor (e.g., 3-axis accelerometer). In some examples, the condition may include a compression condition, which may for example be determined from a pressure sensor or temperature sensor or combination thereof. For example, when a patient lies on a wearable glucose sensor, which may happen for example during sleep, the sensor may generate inaccurate glucose sensor readings (e.g., a "compression low" that suggests a lower glucose value). In some examples, each of these inputs or conditions may trigger a different temperature relationship (e.g., application of a particular temperature compensation model.)

In some examples, temperature compensation, or the application (or suspension) thereof, may be based at least in part on a rate of change of temperature (e.g., the condition may be rate of change of temperature.) Because the external (e.g., sensor electronics) detected temperature can change much faster than a subcutaneous temperature, it may be difficult to correctly predict a subcutaneous temperature during times of rapid temperature change. In some examples, temperature compensation may be suspended or reduce when a detected rate of temperature change satisfies a condition (e.g., the rate of change exceeds a specified value). In another example, a first model (e.g., a linear model) may be used when a first condition is satisfied (e.g., temp rate of change below a specified value), and a second model (e.g. a linear delay model) may be used when a second condition is satisfied (e.g., rate of change is above the specified value.)

In some examples, temperature compensation, or the application (or suspension) thereof, may be based on a magnitude of heat flux or temperature gradient (e.g., the condition may be based on heat flux or temperature gradient.) Heat flux may be determined (e.g., approximated) from a determined subcutaneous temperature (e.g., prior temperature determination) and a detected non-subcutaneous (e.g., external in sensor electronics) detected temperature. In an example, when a temperature gradient or heat flux condition is satisfied (e.g. a temperature gradient or heat flux in excess of a threshold), a model may be adjusted, for example to reflect the reality that external temperature changes faster than subcutaneous temperature. In an example, a "gain" in a linear model (as described above) may be reduced, which may have the effect of reducing the rate of change of determined subcutaneous temperature, to more accurately track the actual rate of temperature change. In another example, temperature compensation may be suspended when a temperature gradient or heat flux condition is satisfied. In some examples, temperature compensation or application thereof may be based on a temperature gradient direction, e.g., temperature compensation when the external temperature is higher than the subcutaneous temperature may be different than temperature compensation when the external temperature is lower than the determined subcutaneous temperature.

In some examples, the condition may be exercise. For example, one or more wearable sensors (e.g., accelerometer, heart rate sensor, respiration sensor) may be used to determine whether a subject is performing some type of cardio exercise (e.g., running, biking, or metabolic conditioning). In an example, it may be assumed that the subject's core body temperature (and subcutaneous temperature) is elevated, e.g., from 37 to 38° C. During a mobile exercise such as running or biking, it may also be assumed that a convection coefficient is increased (e.g., ×10) due to the motion of the subject. An appropriate exercise model may be applied that takes these parameter changes into account. For example, the "gain" (slope) of a linear model may be increased and the offset (constant) may be changed, to reflect the impact of exercise (e.g., a base linear model: Tsubcu=0.395*Texternal+22.346 may shift to a cardio exercise linear model, such as: Tsubcu=0.416*Texternal+22.178.)

In some examples, the amount of temperature compensation applied may be limited when cool temperatures and exercise are detected. For example, during exercise, the transmitter temperature may be colder than when the subject is at rest, for example, because the subject is outside, the sensor electronics are exposed to increased convection due to motion, or because the subject's skin is colder due to sweating. However, subcutaneous temperature may be elevated because of the increased heat production, so a standard temperature compensation model (that does not account for exercise/cold combination) may lead to inaccuracies. This "cold exercise" condition may be detected, for example, through a combination of temperature sensor input and accelerometer, heart rate, respiration rate, or location input. When exercise by a subject is detected, temperature compensation may be modified at cold temperatures, e.g., temperature compensation may be suspended, capped, or tapered, or an alternate compensation model may be applied. In an example, during exercise, any temperature colder than a threshold value may be treated for temperature compensation purposes as the threshold value (e.g., sensor temperature <29° C. get replaced by 29° C. for the purpose of temperature compensation), or temperature compensation may be limited by an algorithm. In another example, tapering compensation may be accomplished by decreasing a temperature sensitivity factor (Z), such that a smaller change is made to subcutaneous temperature for a given detected sensor temperature (e.g., Mt, comp=Mt, pro*(Z)*(Tsubcu–Tsubcu, reference); or Mt, comp=Mt, pro*(Z)*(Tsubcu–Tsubcu, reference)+Mt, pro.) For example, if a typical temperature sensitivity factor is 3.3%, during exercise, the temperature sensitivity factor may be changed to 1.5% based on a detected condition.

In some examples, a compensation model may be selected or determined based at least in part upon the individual's average subcutaneous temperature. In an example, an average subcutaneous temperature may be established the first few hours of a session (e.g., during a warm-up period or after a warm-up period), or in the first day of a session. The long-term average methods described above may be used to determine compensation. In some examples, an average subcutaneous temperature may be updated periodically or recurrently, e.g., every 6 or 12 or 24 hours.

In some examples, a determination may be made (e.g., using an algorithm, model, or look-up table) as to whether temperature compensation is likely to increase the accuracy of estimated glucose concentration levels. For some patients or some conditions, temperature compensation may actually decrease accuracy: Identification of these patients or identifying factors, and suspension or withholding of temperature compensation may increase sensor performance or decrease MARD. Identifying factors may, for example, include surface or body temperature of a host, BMI, gender, age, or any combination of the other conditions identified above.

Figure 9:
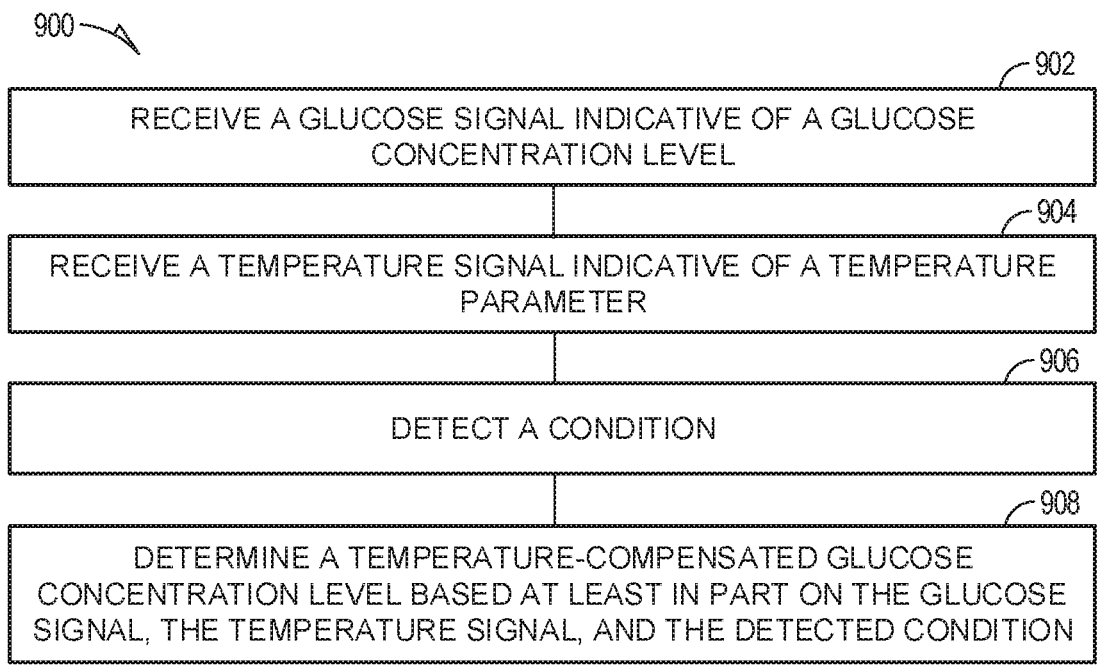
FIG. 9 is a flowchart illustration of an example method for temperature-compensating a continuous glucose monitoring system based at least in part on a detected condition.

FIG. 9 is a flowchart illustration of an example method 900 for temperature-compensating a continuous glucose monitoring system based at least in part on a detected condition. The method 900 may include at 902 receiving a glucose signal indicative of a glucose concentration level.

The method 900 may include at 904 receiving a temperature signal indicative of a temperature parameter.

The method 900 may include at 906 detecting a condition. In some examples, the condition may include a high rate of change in the glucose signal, wherein temperature compensation may be reduced or suspended during a period during which the glucose signal is undergoing a high rate of change. In some examples, the condition may include a body mass index (BMI) value. For example, a host with a high BMI may be assumed to be naturally warmer or change temperature more slowly than a host with a low BMI. In some examples, the condition may include a detected fever, and temperature compensation may be reduced, suspended, capped, or tapered responsive to detection of the fever. In some examples, the detected condition may include the presence of a radiant heat on the continuous glucose monitoring system. In some examples, the condition may include detected exercise. The method may for example include decreasing, tapering, capping, or suspending temperature compensation when a condition (e.g., exercise) is detected.

In some examples, the glucose signal may be received from a continuous glucose sensor, and the condition may include compression on a continuous glucose sensor. For example, compression on the sensor may be detected based at least in part upon a rapid drop in the glucose signal. In some examples, the condition may include sleep. In some examples, the condition may include compression during sleep. Sleep may be detected, for example, using one or more of temperature, posture, activity, and heart rate, and the method may include applying a specified glucose alert trigger based upon the detected sleep.

The method 900 may include at 908 determining a temperature-compensated glucose concentration level based at least in part on the glucose signal, the temperature signal, and the detected condition.

In some examples, the condition may include a sudden change in the temperature signal. Temperature compensation may, for example, be reduced or suspended in response to detection of the sudden change in temperature. A sudden change in temperature has likely not occurred at an analyte sensor site in subcutaneous location, where temperature changes tend to occur more gradually as heat is conducted to or away from the sensor site through the skin, so when a sudden temperature change occurs at an external sensor, it may be appropriate to suspend temperature compensation for a period of time or to "phase in" temperature compensation over a time period to reflect the gradual temperature change at the sensor site. One or more of a variety of techniques may be used to determine a temperature-compensated glucose level after a sudden change in temperature or other rapid change or signal discontinuity is detected. In some examples, a temperature-compensated glucose concentration level may be determined using a previous temperature signal value in lieu of a temperature signal value that associated with a sudden change in temperature. In some examples, a temperature-compensated glucose concentration level may be determined an extrapolated temperature signal value based on prior temperature signal values and using the extrapolated temperature signal value in lieu of a temperature signal value that associated with a sudden change in temperature. In some examples, a delay model may be invoked in response to detection of a sudden change in temperature. For example, the delay model may specify a delay period for use in determining the temperature-compensated glucose level.

One or more of a variety of techniques may be used to determine a temperature-compensated glucose concentration level based on the glucose signal, the temperature signal, and the detected condition. For example, a linear model may be used to determine the temperature-compensated glucose concentration level. In another example, a time series model may be used to determine the temperature-compensated glucose concentration level. In some examples, a partial differential equation may be used to determine a temperature-compensated glucose concentration level. In some examples, a probabilistic model may be used to determine the temperature-compensated glucose concentration level. For example, a state model may be used to determine the temperature-compensated glucose concentration level.

In some examples, the method may include determining a long-term average using the temperature signal, and the temperature-compensated glucose concentration level may be determined using the long-term average.

In some examples, the method may further include receiving a blood glucose calibration value and updating a temperature compensation gain and offset may when a blood glucose calibration value is received.

The method may further include delivering an insulin therapy. The insulin therapy (e.g., via pump or smart pen) may be determined at least in part based upon the temperature-compensated glucose level.

Other Factors to be Considered in Temperature Compensation

In some examples, temperature compensation may be based at least in part on body mass index (BMI). In an example, height and weight may be received from a subject, for example via an interface of a smart phone app. Temperature compensation parameters may be determined or adjusted based at least in part on the BMI. In some examples, temperature compensation may be based on preloaded models, which may be associated with specified BMI windows. For example, a standard temperature compensation model may assume a certain distance from the subcutaneous layer (where the working electrode is designed to sit during use) and tissue that is at core body temperature. In people with high BMI, thicker layers of adipose tissue (body fat) may increase the distance from the subcutaneous layer to the tissue that is at core body temperature, which may result in lower subcutaneous or skin surface temperatures. In some examples, a group of models may be available and a model (e.g., PDE models where the distance to core body temperature is varied), and a model would be selected from the group based at least in part on the person's BMI. In some examples, additional information in addition to BMI may be used to select a model, as BMI does not perfectly predict adipose tissue thickness, especially not at the location of the analyte sensor (e.g., CGM).

In some examples, a temperature compensation model could be based at least in part on the core body temperature of a subject. For example, body temperature tends to correlate with BMI, so the average body temperature may be estimated based upon BMI.

Other physiological factors or affects such as local glucose concentration variations (as opposed to systemic glucose levels), compartment bias (differences in glucose concentration in interstitial fluid vs. blood), and non-enzyme sensor bias may also be considered in determination of a compensated analyte concentration level.

In some examples, a sensor signal from an optical sensor with a light source and a light sensor may be as input for a temperature compensation method. For example, an optical sensor may be used to detect blood flow or perfusion in the skin of a subject. An optical sensor with a light source and light detector near the skin of a subject can detect blood flow velocity and number of red blood cells in the area immediately under the sensor. Blood flow near the skin changes with temperature, activity, and stress level. In some examples, an amount of effort (e.g., exercise exertion) may be determined through the use of blood perfusion information obtained from an optical sensor. For example, when running uphill or downhill, steps will be about the same, but uphill requires more exertion and blood perfusion would be higher. During a downhill section, blood perfusion would be lower. Specific exertion detection may be used for a more refined temperature compensation algorithm to be used during exercise. In some examples, an optical sensor may detect exercise that is less apparent from an accelerometer (e.g., weight training) because the exercise involves less or slower movement. In some examples, an optical sensor may be used in combination with an accelerometer to detect an exercise state and an amount of exertion during the exercise.

In some examples, location information (e.g., global positioning sensor data or network connectivity) may be used as an input for determining temperature compensation or determining confidence in a temperature measurement. For example, location may be used to establish confidence in the temperature measurement by comparing a temperature measurement to temperature characteristics of location. For examples, an activity (e.g., swimming, sunbathing, running, skiing) associated with a location may establish confidence in a low, high, or rapidly changing temperature measurement. In another example, a weather characteristic (e.g., ambient temperature) at a location may establish confidence in a temperature measurement. In another example, a temperature measurement may be confirmed using location information that correlates with the circadian rhythm (e.g., usually sleeping at a home location), or a deviation from a circadian rhythm may be confirmed by a deviation from a pattern in location information (e.g., confidence in a nighttime cold temperature may established if the subject is away from home, e.g., outside at night, camping, at a location that may have different temperature characteristics.)

In some examples, the detection of fever (e.g., using a sensor) or reporting of fever (e.g., through an app on a smart device) may be used as an input for determining temperature compensation. For example, temperature compensation may be suspended during a fever because the normal patterns may not apply. In another example, a model may be modified or a different model may be applied to compensate for the change in temperature caused by the fever. In some examples, fever may be corroborated with other information. For example, the correlation in rate-of-change of sensor output illustrated in FIGS. 15A-C may be used to corroborate a detected fever. In another example, a patient may be queried, for example by a smart device with an inquiry about a fever ("Do you have a fever?") or other events that may cause a temperature change ("Did you recently take a bath").

Example Model

Figure 19:
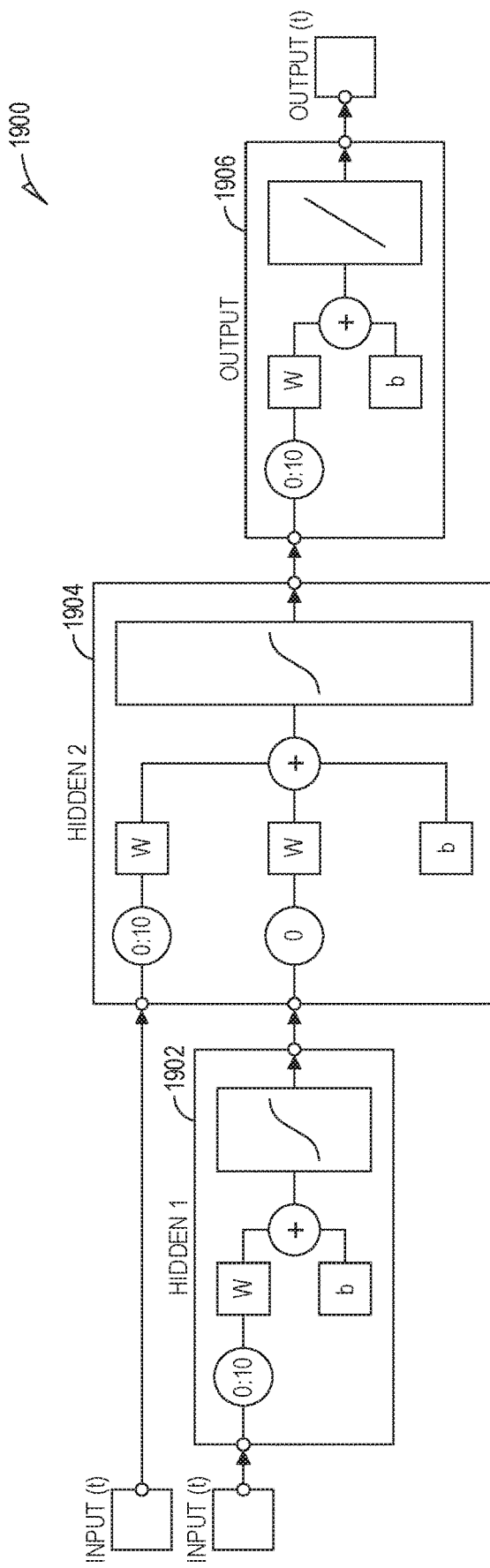
FIG. 19 is a schematic illustration of an example model that may be used to determine an output from two or more inputs that may be received at different points in time.

FIG. 19 is a schematic illustration of an example model that may be used to determine an output from two or more inputs. For example, the model may learn patterns or relationships from prior data and apply learned patterns or relationship in determination of an output. This may include, for example, learning from previous data from the particular host, or from a population, or from one or more clinical trials.

In various examples, the inputs may be received or sensed simultaneously, or at different points in time. In some examples, two inputs (e.g., temperature and analyte sensor output) may be applied to a model. The model may also receive additional inputs, such as time (e.g., from a clock circuit), or sensitivity (e.g., a factory-calibrated sensitivity.) In an example, the model may include sub-models 1902, 1904, 1906. The sub-models may account for temperature-dependent factors such as local glucose level, a compartment bias value, a non-enzyme sensor bias level, and sensor sensitivity. In an example, each model may define a different relationship (e.g., linear, non-linear) between inputs and temperature-dependent factors. For example, model 1902 may be based upon a first non-linear relationship, model 1904 may be based upon a second non-linear relationship, and output model may be based upon a linear relationship. In various examples, a processor may retrieve model information or input data from a look-up table in memory or may store and retrieve past values or states from memory or may retrieve a function or other aspect of the model from memory. Retrieved information may be combined with recent or real-time information and applied to a model to generate an output, which may be a compensated glucose concentration level, or the output may be used to determine a compensated glucose concentration level.

Figure 20A:
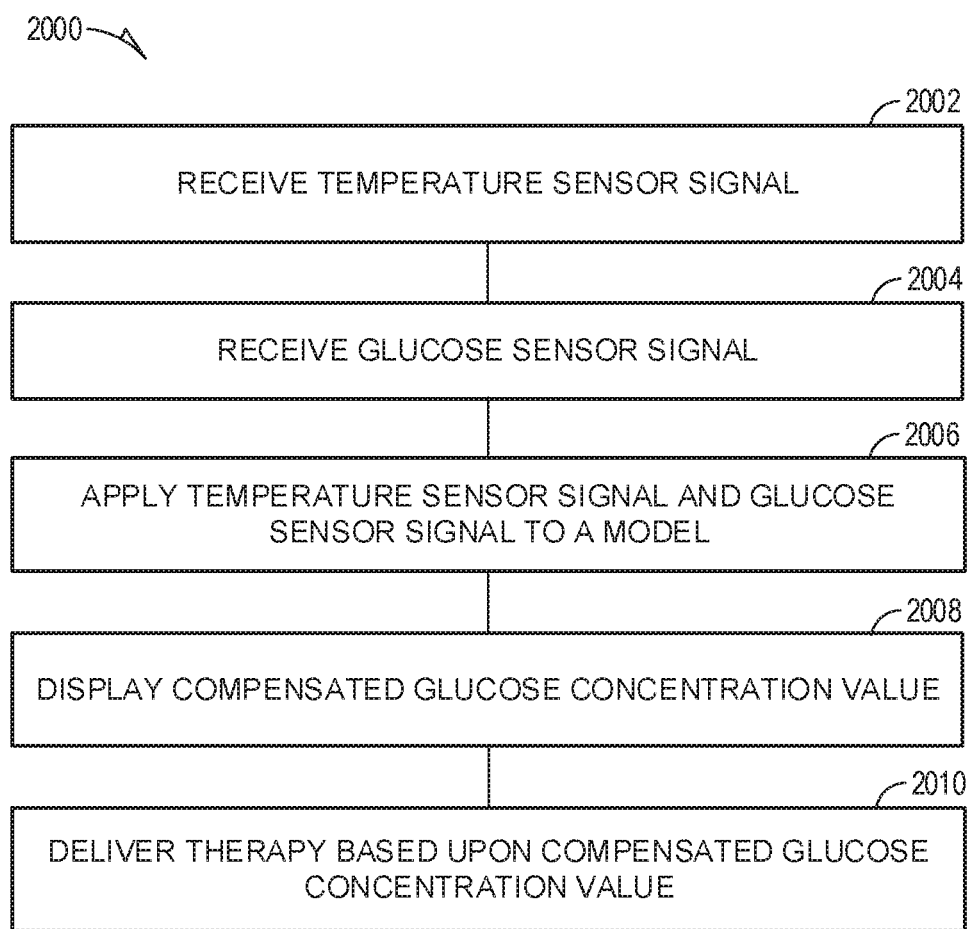
FIG. 20A is a flowchart illustration of an example method of determining a compensated glucose concentration value using a model.

FIG. 20A is a flowchart illustration of an example method 2000 of determining a compensated glucose concentration value using a model. The method 2000 may include at 2002 receiving a temperature sensor signal. For example, a temperature sensor signal may be received from a subcutaneous temperature sensor proximate an analyte sensor, or a temperature sensor signal may be received from a non-subcutaneous sensor (e.g. on external sensor electronics, e.g. a CGM transmitter). At 2004, the method 2000 may include receiving an analyte sensor signal, such as a signal from a glucose sensor. At 2006, the temperature sensor signal and glucose sensor signal may be applied to a model. For example, the temperature sensor signal and glucose sensor signal may be applied to a state model (e.g., hidden Markov model) or neural network. In some examples, multiple temperature sensor signals may be applied to the model. The signals may be processed or analyzed to determine a pattern (e.g., one or more linear or non-linear trends). A defined or learned relationship between temperature and glucose sensor values and compensated glucose concentration values may be used to return a compensated glucose concentration value using the model. At 2008, a compensated glucose concentration value may optionally be displayed on a user device. At 2010, a therapy may be delivered based at least in part upon the compensated glucose concentration value. For example, insulin delivery via a pump may be controlled based at least in part on the compensated glucose concentration value. In some examples, a processor may determine an insulin dosage, delivery time, or delivery rate (or any combination thereof) based at least in part on the glucose concentration value. In some examples, the pump may automatically deliver insulin, or the pump may suggest insulin time, rate, and dosage to a user. In other examples, a smart pen may receive the compensated glucose concentration value and determine a dose or deliver time, which may be displayed to a user or automatically loaded for delivery, or both.

In the example of FIG. 20A, the model is trained to provide a compensated glucose concentration as its output. In other examples, as described, herein, the model is trained to generate an output that includes one or more compensated properties of the glucose sensor. For example, as described herein, temperature compensation can be applied to sensor properties to generate one or more compensated sensor properties. The one or more compensated sensor properties can then be applied to a raw sensor data to generate a compensated glucose concentration. Example sensor properties that may be compensated using the trained model include, for example, sensitivity, sensor baseline, etc.

Figure 20B:
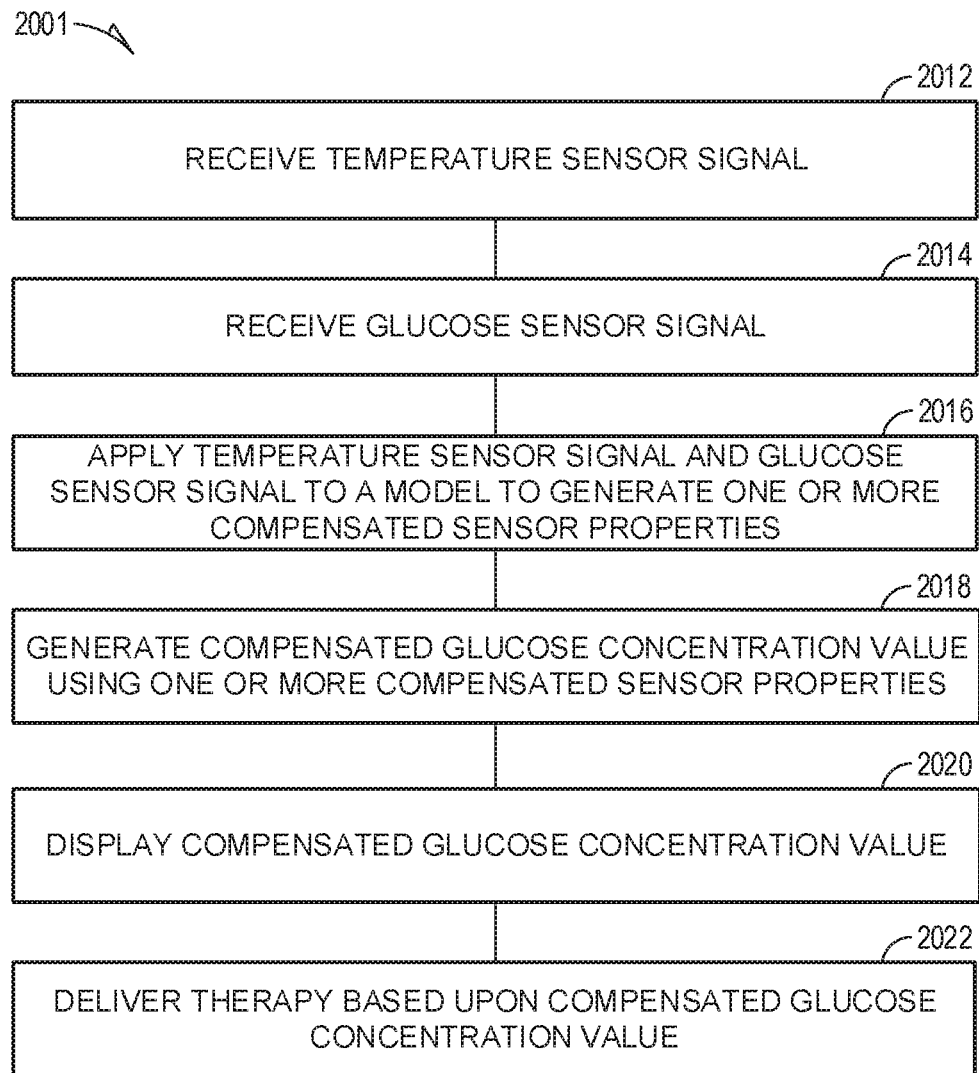
FIG. 20B is a flowchart illustration of another example method of determining a compensated glucose concentration value using a model.

FIG. 20B is a flowchart illustration of another example method 2001 of determining a compensated glucose concentration value using a model. The method 2001 may include at 2012 receiving a temperature sensor signal. For example, a temperature sensor signal may be received from a subcutaneous temperature sensor proximate a glucose sensor, or a temperature sensor signal may be received from a non-subcutaneous sensor (e.g. on external sensor electronics, e.g. a CGM transmitter). At 2014, the method 2001 may include receiving a glucose sensor signal, such as a signal from a glucose sensor. The glucose sensor signal received at 2014, in some examples, includes a raw sensor signal related to the current at the working electrode, such as a count or counts related to current at the working electrode of the glucose sensor. In some examples, includes an analyte concentration, such as a glucose concentration, for example, derived from a raw sensor signal. In some examples, the glucose sensor signal includes a raw sensor signal and an analyte concentration.

At 2016, the temperature sensor signal and glucose sensor signal may be applied to a model. For example, the temperature sensor signal and glucose sensor signal may be applied to a state model (e.g., hidden Markov model), a neural network model, or other suitable model. In some examples, multiple temperature sensor signals may be applied to the model. The signals may be processed or analyzed to determine a pattern (e.g., one or more linear or non-linear trends). A defined or learned relationship between temperature and glucose sensor values and one or more glucose sensor properties such as sensitivity, baseline, etc., may be used to return values for the one or more compensated glucose sensor properties.

At 2018, the compensated glucose sensor properties are used to generate a compensated glucose concentration. At 2020, a compensated glucose concentration value may optionally be displayed on a user device. At 2022, a therapy may be delivered based at least in part upon the compensated glucose concentration value. For example, insulin delivery via a pump may be controlled based at least in part on the compensated glucose concentration value. In some examples, a processor may determine an insulin dosage, delivery time, or delivery rate (or any combination thereof) based at least in part on the glucose concentration value. In some examples, the pump may automatically deliver insulin, or the pump may suggest insulin time, rate, and dosage to a user. In other examples, a smart pen may receive the compensated glucose concentration value and determine a dose or deliver time, which may be displayed to a user or automatically loaded for delivery, or both.

Compensation Based on Electrical Conductance

In some examples, temperature compensation or estimated subcutaneous temperatures may be based at least in part on electrical conductance (or electrical resistance, the reciprocal of conductance) of an analyte sensor, or portion thereof. For example, a measured conductance of the analyte sensor 10 or the conductive portion 286 of the analyte sensor shown in FIG. 2C may be used for temperature compensation or estimation of a subcutaneous temperature.

Empirical measurements (discussed below and shown in FIG. 21) have shown that the conductance of an analyte sensor may depend strongly on temperature. In some examples, this relationship between conductance and temperature may be used to estimate a subcutaneous temperature, which may be used in a temperature compensation model or other method. In other examples, the relationship between conductance and temperature may be applied directly (e.g., without using an estimated temperature) to compensate for subcutaneous temperature variations.

Figure 21:
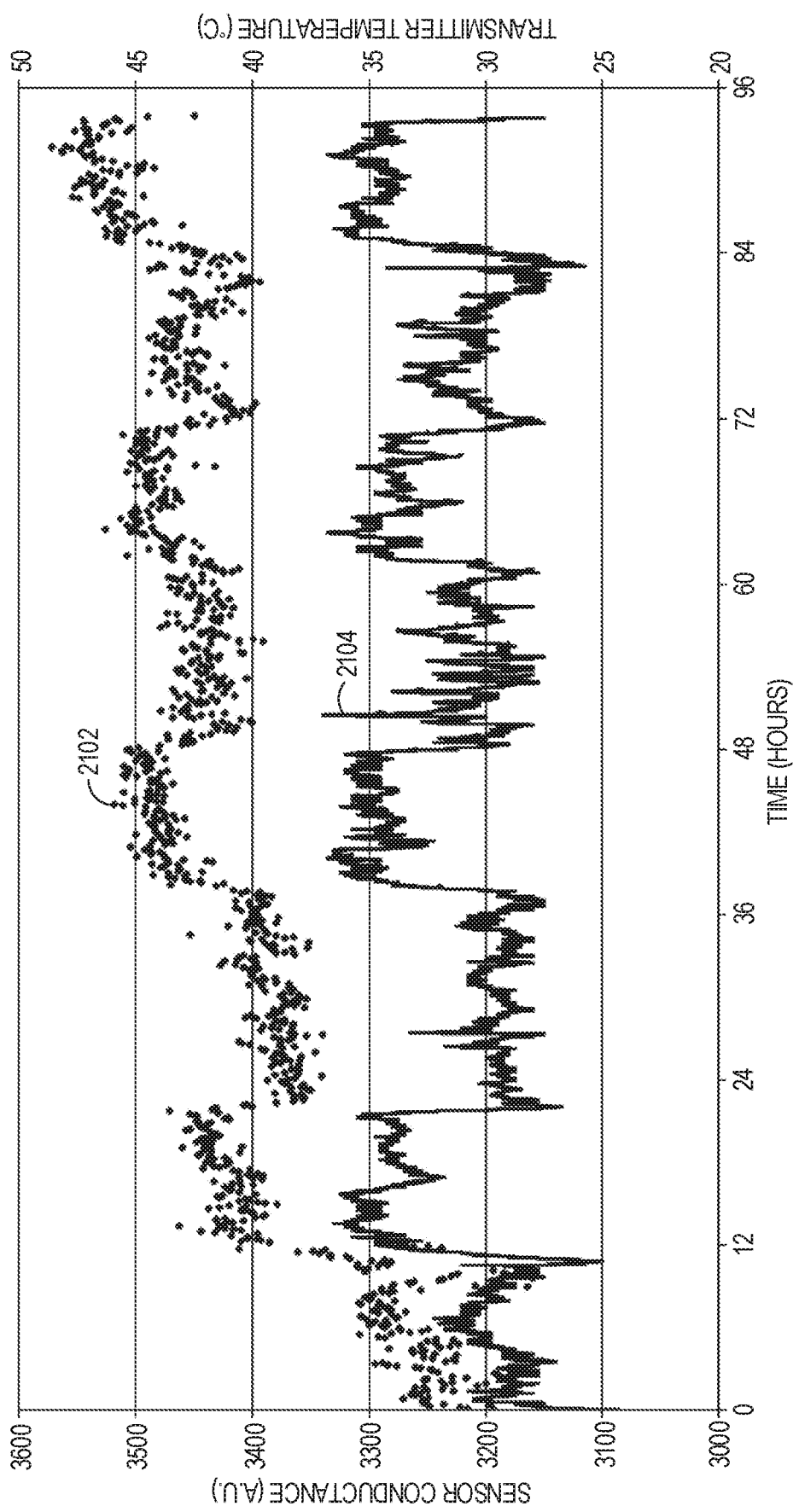
FIG. 21 is a graph showing temperature and impedance plotted against time.

FIG. 21 is a plot of sensor conductance 2102 and transmitter temperature 2104 against time. A strong correlation is observable between temperature and conductance: When the transmitter temperature goes up, the sensor conductance goes up (about 6% per degree Celsius), and vice versa. While the data shown is for transmitter temperature, the same correlation exists between subcutaneous temperature and conductance.

The correlation between temperature and sensor conductance may be used to determine an estimate of the temperature at the working electrode temperature (e.g., to determine a subcutaneous temperature at the analyte sensor). In various examples, a system or method may use a non-subcutaneous temperature (e.g., transmitter temperature), or a system or method may compensate without using a non-subcutaneous temperature (e.g., as described above, a system may use an assumed reference temperature or factory-calibrated temperature.)

An initial estimate for the working electrode temperature may be made using one (or more) of a variety of models (e.g., linear model), delay model, partial differential equation model, time series model). The initial estimate may also be based on a predetermined referenced value, or other methods as described herein. This initial estimate may then be used to determine an adjusted temperature using one or more sensor conductance measurements. For example, as the conductance changes, a corresponding temperature change may be calculated, and this temperature change may be applied (e.g., added to or subtracted from) an initial temperature estimate or reference temperature to determine a temperature at the time of sensor conductance measurement.

In various examples, conductance-based temperature compensation techniques may be combined with any of the examples described herein for determining an estimated subcutaneous temperature, or an estimated impact of subcutaneous temperature on a signal from an analyte sensor. For example, an estimated subcutaneous temperature (e.g., temperature at the working electrode of an analyte sensor) may be determined from a measured non-subcutaneous temperature (e.g., a transmitter temperature) at a first time, and a conductance of the analyte sensor or a portion thereof may be measured contemporaneous with the non-subcutaneous temperature measurement. At a later time, a second subcutaneous temperature may be estimated based on a difference between a conductance value (single point, or average) at the later time and a conductance value (single point, or average) from the first time.

The conductance values 2012 plotted in FIG. 21 show an upward drift over time. This drift component may be related to sensor sensitivity drift, as described in U.S. Patent Publication No. US20150351672, which is incorporated by reference.

In some examples, a system may implement one or more techniques to account for the drift and avoid or reduce the impact of conductance drift on subcutaneous temperature estimates or compensated data. Such techniques to address drift may, for example, resetting of temperature estimates (e.g., recalculating an estimated temperature and a conductance baseline against which future values are compensated), compensation based on an average (e.g., compensating against a moving baseline conductance based on a long-term average, weighted average, or rolling window.)

In various examples, a subcutaneous temperature estimate or conductance baseline may be periodically refreshed. For example, a new subcutaneous temperature estimate (e.g., working electrode temperature) may be recurrently (e.g., periodically) refreshed (e.g., reset) by recalculating an estimate (e.g., using a technique discussed above). Future analyte concentration values may be compensated against a conductance value (or average) that is time-correlated (e.g., contemporaneous) with the new subcutaneous temperature estimate. This refreshing (resetting) of the conductance-based temperature estimate may remove or reduce the impact of the drift component, resulting in more accurate temperature estimates.

In some examples, a reset, refresh, or error status may be triggered based upon satisfaction of a condition. A condition may, for example, be based upon a comparison conductance-compensated temperature estimate with a subcutaneous temperature estimate that is determined in a different manner (e.g., that is not based on conductance), such as a newly-calculated subcutaneous temperature estimate based on a transmitter temperature and a linear model, delay model, or other model discussed herein). The condition may be satisfied, for example, when the two values differ by more than a set threshold. In some examples, when the comparison satisfies an error condition, an error status may be changed (e.g., an error state may be declared. In some examples, a conductance baseline may be reset (e.g., the baseline may be updated to a new value or to an average), or a new temperature estimate may be correlated with a particular conductance value. In some examples, a tiered approach may be applied, such that a reset procedure may be applied when the difference exceeds a reset threshold, and an error condition may be applied when the difference is above an error threshold that is larger than the reset threshold (in which case the reset may still occur, or may not occur.) This resetting of the conductance-based temperature estimate may remove or reduce a drift component that is visible in the conductance signal in FIG. 21 (e.g., the conductance value drifts up over time).

In some examples, a digital high pass filter may be applied to block the low frequency drift component from the conductance signal, and only pass the temperature related changes. Filter characteristics such as cut off frequency, may be based on actual measured temperature data, preferably subcutaneous temperature measurement data (e.g. by frequency analysis such as Fourier decomposition).

While the discussion above is focused on conductance and resistance, it is understood that temperature compensation or temperature estimates may alternatively be based on other electrical conductive properties (e.g., impedance or admittance), depending on the configuration of the analyte sensor system and the type of signal applied.

Figure 22:
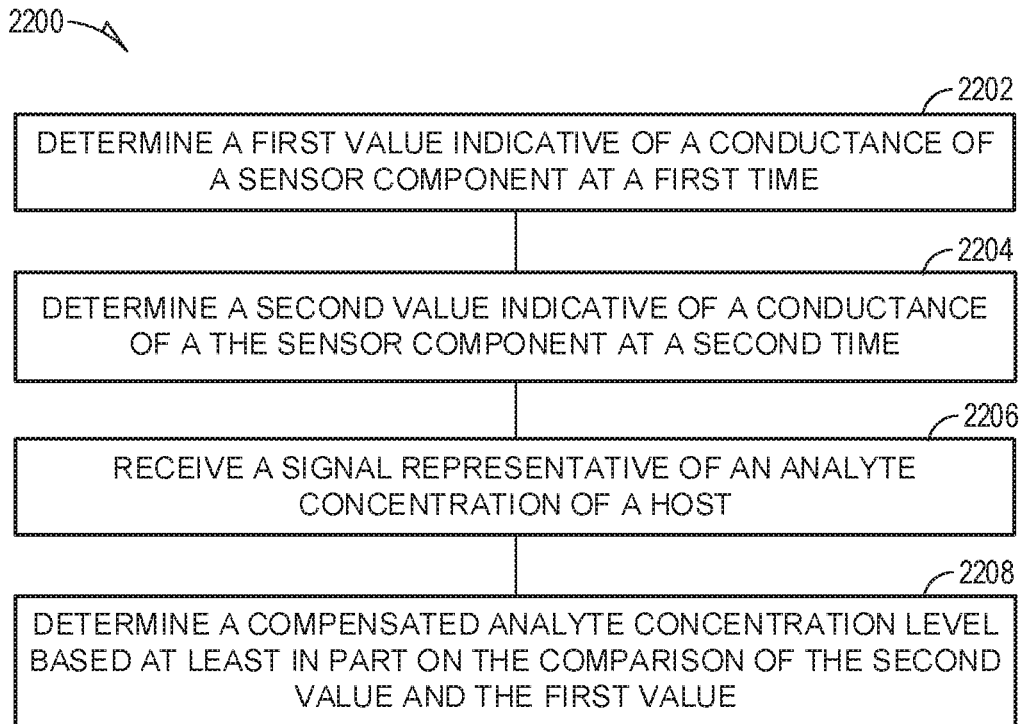
FIG. 22 is a flowchart illustration of an example method of temperature compensation using conductance or impedance.

FIG. 22 is a flowchart illustration of an example method 2200 of temperature compensation using conductance or impedance. At 2202, a first value indicative of a conductance of a sensor component at a first time is determined. At 2204, a second value indicative of a conductance of the sensor component at a later time is determined. At 2206, a signal representative of an analyte concentration of a host is received. At 2208, a compensated analyte concentration level is determined based at least in part on a comparison of the second value and the first value. In some examples, determining the first value may include determining an average conductance over a period proximate or including the first time. In some examples, the method may further include determining a first estimated subcutaneous temperature that is time-correlated with the first value and determining a second estimate subcutaneous temperature that is time-correlated with the second value, wherein the second estimated subcutaneous temperature is determined based at least in part on a comparison of the second value with the first value. In some examples, the method may include determining a third estimated subcutaneous temperature that is time-correlated with the second value, determining whether a condition is satisfied based upon a comparison of the third estimated subcutaneous temperature and the second estimated subcutaneous temperature, and declaring an error or triggering a reset responsive to satisfaction of the condition. The method may include triggering a reset, wherein triggering a reset includes determining subsequent estimated subcutaneous temperatures based upon the third estimated temperature and the second value or based upon a third value indicative of a conductance at a subsequent time and a fourth estimated subcutaneous temperature that is time-correlated with the third value.

In some examples, the method 2200 may include compensating for drift in the conductance value, for example by applying the methods described above, or by applying a filter.

Figure 23:
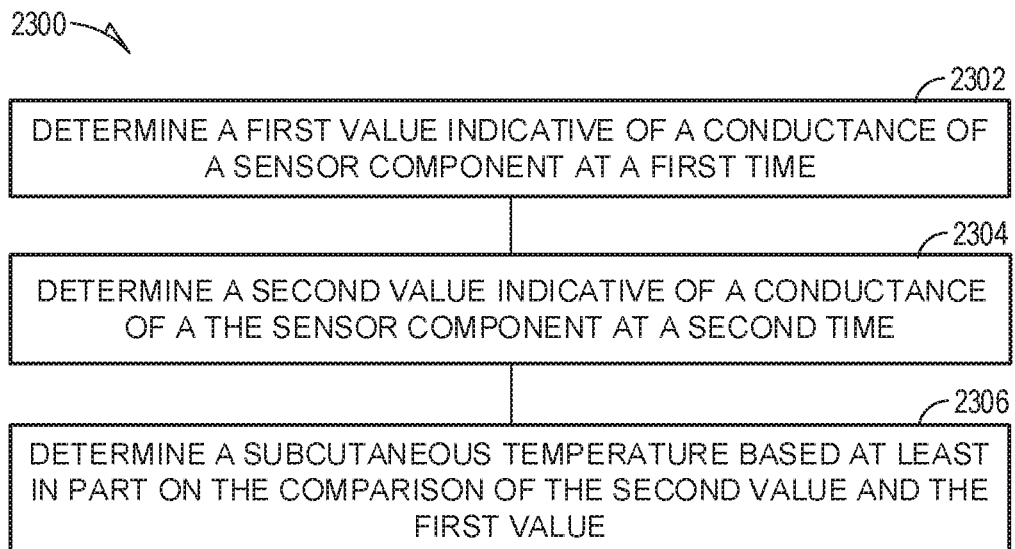
FIG. 23 is a flowchart illustration of an example method of determining an estimated subcutaneous temperature using conductance or impedance.

FIG. 23 is a flowchart illustration of an example method 2300 of determining an estimated subcutaneous temperature using conductance or impedance. At 2302, a first value indicative of a conductance of a sensor component at a first time may be determined, for example by measure a conductance or impedance of the sensor component. At 2304, a second value indicative of a conductance of the sensor component at a later time may be determined, for example by taking a second measurement to determine conductance, or impedance. At 2306, an estimated subcutaneous temperature may be determined based at least in part on a comparison of the second value and the first value. As described above, an estimated temperature for the first time may be determined using a non-subcutaneous temperature measurement, and subsequent estimated subcutaneous temperatures may be determined based upon changes in the value indicative of conductance. An error condition may be declared or a reset triggered when variations in excess of a threshold, or a comparison otherwise satisfies an error condition or reset condition). It should be understood that any of the estimated temperatures described herein could be used as an input for any of the temperature compensation models described herein.

Temperature Sensor Calibration

In some examples, a temperature sensor may be calibrated during a manufacturing step where a process temperature is known or controlled. For example, some sensor electronics packages using an adhesive or structural agent such as epoxy that may be cured at a known or controlled temperature. A temperature sensor may be calibrated during the curing step. In another example, a temperature sensor may be calibrated when an analyte sensor is calibrated. In another example, a temperature sensor may be calibrated during an initial period of wear. For example, the temperature sensor output during an initial period (e.g., the first one or two hours after initiation of an analyte sensor) may be calibrated to a pre-determined average (e.g., 37° C.).

Figure 10:
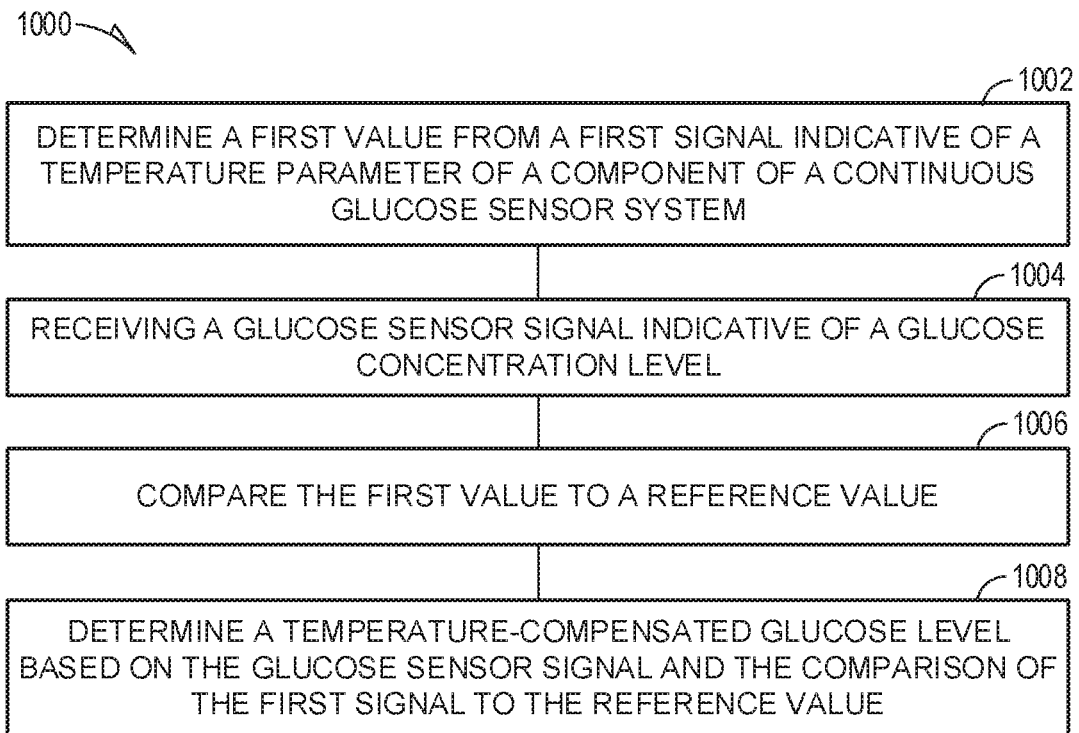
FIG. 10 is a schematic illustration of a method for temperature-compensating a continuous glucose sensor system using a reference temperature value.

FIG. 10 is a schematic illustration of a method 1000 for temperature-compensating a continuous glucose sensor system using a reference temperature value. The method may include at 1002 determining a first value from a first signal indicative of a temperature parameter of a component of a continuous glucose sensor system. The method may include at 1004 receiving a glucose sensor signal indicative of a glucose concentration level. The method may include at 1006 comparing the first value to a reference value.

The method may include at 1008 determining a temperature-compensated glucose level based on the glucose sensor signal and the comparison of the first signal to the reference value.

In some examples, the method may further include determining the reference value. For example, the reference value may be determined from the first signal. For example, the continuous glucose sensor system may include a glucose sensor that is insertable into a host, and the reference value may be determined during a specified time period after insertion of the glucose sensor in a host or a specified time period after activation of the glucose sensor. In other examples, the reference value may be determined during a manufacturing process.

In some examples, the reference value may be during a first time period, and the first value may be determined during a second time period after the first time period (e.g., a reference value may be established after insertion of the sensor and subsequent sensor readings may be compensated in relation to the reference value.) In some examples, the reference value may be a long term average and the first value may be a short term average. In some examples, the reference value may be updated based upon subsequently received temperature values. For example, the reference value may be updated based on one or more temperature signal values obtained in a third time period after the second time period.

In some examples, a reference value may be determined based on an average of a plurality of sample values obtained from the first signal.

Figure 11:
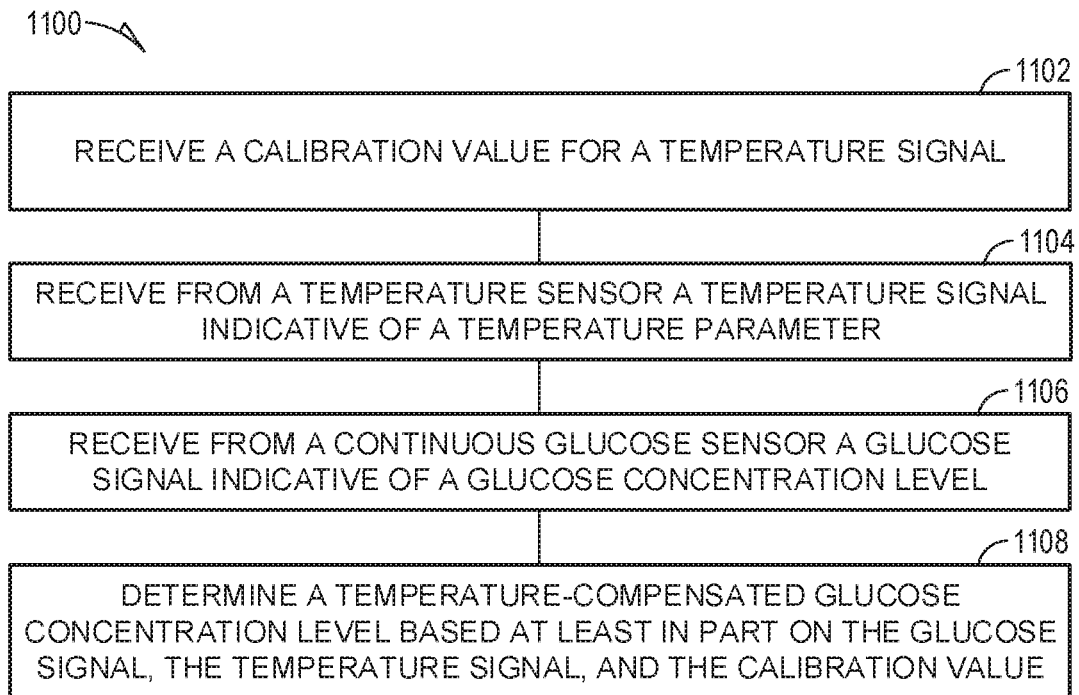
FIG. 11 is a flowchart illustration of an example continuous glucose sensor temperature-compensation method.

FIG. 11 is a flowchart illustration of an example continuous glucose sensor temperature-compensation method 1100. The method may include, at 1102, receiving a calibration value for a temperature signal. In some examples, the calibration value may be obtained during a manufacturing step having a known temperature. In some examples, a calibration value for the temperature signal may be obtained during a specified period of time after insertion of the continuous glucose sensor in a host. For example, a calibration value may be determined after a warm-up period, which may, for example, be a two-hour period after insertion or activation of a sensor. For example, a calibration value may be determined during a subsequent time period (e.g., hours 2-4 after insertion) after the warm-up period. The method may include, at 1104, receiving from a temperature sensor a temperature signal indicative of a temperature parameter. The method may include, at 1106, receiving from a continuous glucose sensor a glucose signal indicative of a glucose concentration level. The method may include, at 1108, determining a temperature-compensated glucose concentration level based at least in part on the glucose signal, the temperature signal, and the calibration value.

Methods Involving Relative Temperature Differences

In some examples, relative temperature variations may be used for temperature compensation. For example, an uncalibrated temperature sensor or a temperature with low absolute accuracy may be used for temperature compensation by basing temperature compensation on a deviation from a reference, as opposed to knowledge of an absolute temperature. This may include, for example, using an individualized dynamic reference temperature (e.g., a reference temperature determined for a particular sensor or session, which may be periodically refreshed or recomputed), and using deviations from that reference temperature to apply compensation.

In some examples, a temperature difference may be determined from a reference state based upon a variation of the first value from a reference value without, calibrating a temperature for the reference value. This may enable, for example, compensating for a temperature difference from the reference value, even if an absolute temperature is not determined, which may be useful when a temperature sensor is not factory calibrated, to assure accurate absolute temperatures, or when using a sensor that has good relative accuracy or precision but less reliable absolute accuracy or precision. In some examples, the temperature-compensated glucose level may be determined based at least in part on a temperature-dependent sensitivity value that varies based on a deviation of the first value from the reference value.

In some examples, temperature compensation may be performed using a temperature sensor that has low absolute accuracy. For example, even though a sensor is not accurate in an absolute sense (e.g., +−3° C. or 5° C. variation in absolute temperature), the sensor may be sufficiently accurate in a relative sense (e.g., accurately detect that a sensor is 1° C. warmer than at a previous (reference) time point). The use of these types of sensor may be advantageous because the sensor may be built in to sensor electronics for other reasons (e.g., to detect overheating), and may require simpler or less expensive calibration steps.

In an example, a reference temperature may be obtained when a blood glucose value (e.g., blood glucose meter using a finger stick) is received. For example, when the blood glucose value is received, glucose sensitivity may be determined (e.g., calculated) based on a signal from an analyte sensor (glucose sensor), and a signal from a temperature may be taken (e.g., declared) as a reference temperature. Later, a signal from the temperature sensor may be used to determine a temperature difference from the reference temperature, and temperature compensation may be based upon the difference. For example, later the temperature may be determined to be 1.5° C. warmer than the reference temperature, and temperature compensation may be applied based upon the 1.5° C. difference. In some examples, the temperature compensation may be based upon a raw or processed signal from a temperature sensor, as opposed to a computed temperature difference.

In various examples, a reference temperature may be determined during a specified time period, e.g., the first two hours or first 24 hours after a sensor session is initiated. In an example, the reference temperature may be an average (e.g., mean or median) temperature during the specified time period. In some examples, the reference temperature may be used for the remainder of the session. In other examples, the reference temperature may be recurrently or periodically updated. For example, the reference may be updated every 24 hours, and the reference temperature may be used for the subsequent 24 hours. In some examples, for the purpose of temperature compensation, the reference temperature may be assumed to a specific value (e.g., 35 C, which may be assumed as the average subcutaneous temperature for a general population of subjects). In some examples, a temperature sensor value at a time of calibration (during manufacture or after insertion) may be taken as a reference value.

Real-time temperature compensation may be determined using a real-time (or recent) temperature signal and the reference temperature value, using any of the compensation methods described herein (linear, linear with delay, polynomial, etc.) In some examples, temperature compensation using relative temperatures may obtain 75% (or more) of the MARD improvement achieved using a calibrated temperature sensor.

Exercise

Exercise, or conditions indicative, may be detected and used to determine temperature compensation. Exercise may, for example, be detected based on temperature data, accelerometer data (e.g., to detect walking or running), location data (e.g., based on presence at a location associated with exercise, or based on locational movement associated with walking, running, or biking), physiological data (e.g., respiration, heart rate, or a skin surface condition).

In some examples, a method may include detecting a rise in the first temperature signal and a drop in the second temperature signal and adjusting a temperature compensation model based upon the detected rise and drop. In some examples, an exercise session (e.g., outdoor exercise or convectively cooled exercise) may be detected based at least in part on the detected rise in the first signal and drop in the second signal. For example, a drop in a second signal may indicate the beginning of an exercise session in a cool environment (e.g., outside on a cold day, or an exercise session in an actively cooled environment, e.g., near a fan): A drop in a temperature signal from a second sensor that is external (e.g., in sensor electronics) may indicate a drop in temperature responsive to an ambient temperature outdoors being lower than an ambient temperature indoors, or responsive to convective cooling (e.g., from running or biking or from a fan, e.g. adjacent a treadmill or other workout space). A rise in temperature (or steady temperature) in the first temperature signal, which may for example be received from an external sensor positioned closer to the body than the second sensor or from a sensor that is subcutaneous (e.g., on or integrated into a glucose sensor), may indicate warming of the body due to exercise, or the absence of a drop in temperature despite the change in ambient temperature, because of heat generated by exercise.

Figure 12:
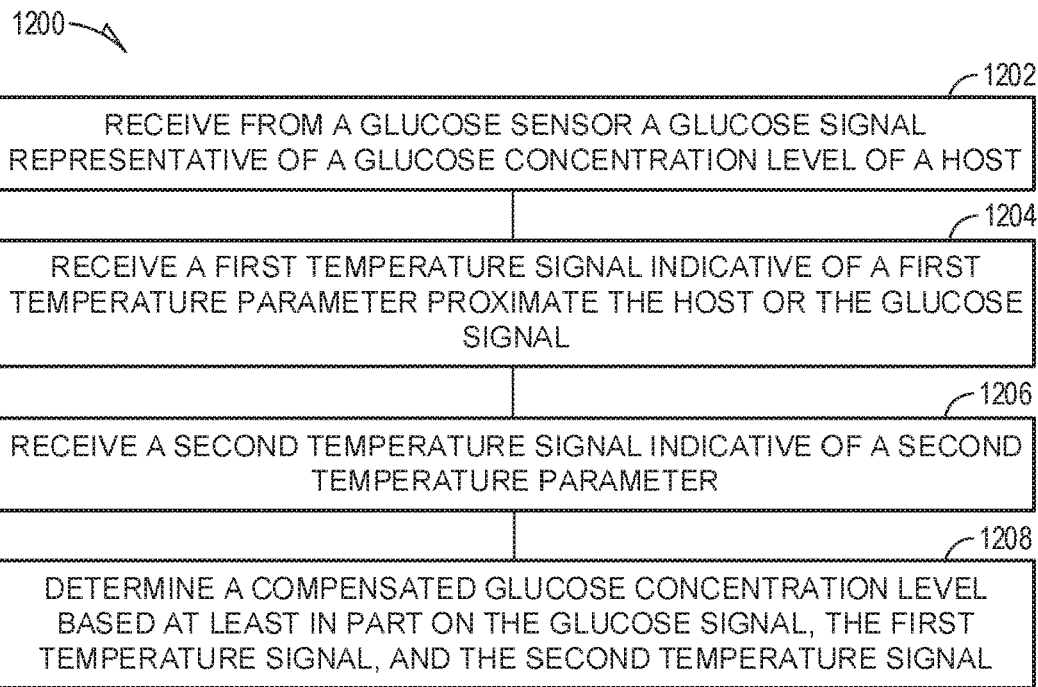
FIG. 12 is a flowchart illustration of an example method of temperature compensation using two temperature sensors.

FIG. 12 is a flowchart illustration of an example method 1200 of temperature compensation using two temperature sensors. The method 1200 may, for example, be implemented in the system shown in FIG. 2C. The method 1200 may include at 1202 receiving from a glucose sensor a glucose signal representative of a glucose concentration level of a host.

The method 1200 may include at 1204 receiving a first temperature signal indicative of a first temperature parameter proximate the host or the glucose sensor. The method 1200 may include at 1206 receiving a second temperature signal indicative of a second temperature parameter. In some examples, the first temperature signal may be received from a first temperature sensor coupled to the glucose sensor, and the second temperature signal may be received from a second temperature sensor coupled to the glucose sensor.

The method 1200 may include at 1208 determining a compensated glucose concentration level based at least in part on the glucose signal, the first temperature signal, and the second temperature signal. In some examples, the compensated glucose concentration level may be determined based at least in part on a temperature gradient between the first temperature sensor and the second temperature sensor or based at least in part on a heat flux between the first temperature sensor and the second temperature sensor. In some examples, the method 1200 may include detecting an exercise session based on the two temperature signals, as described above (e.g., based on divergence of detected temperatures), and compensating accordingly (e.g., applying an exercise model.

In some examples, the method 1200 may further include determining that a temperature change is due to radiant heat or ambient heat based at least in part on the second temperature signal and adjusting a temperature compensation model based upon the determination. For example, when the second temperature signal is from a sensor near an outer surface of a wearable sensor, and the second temperature signal is significantly higher than the first temperature signal, it may be inferred that the sensor is being exposed to radiant heat. In some examples, a rate of change may also be considered. For example, a rapid rate of change may indicate immersion in hot water, wherein as more gradual rate of change may indicate exposure to radiant heat. In some examples, a state model may include one or more of a radiant heat state, a water immersion state, an exercise state, an ambient air temperature state, or an ambient water temperature state, and the state model may be used to for temperature compensation of an estimated glucose concentration value.

Other Uses for Temperature Sensors

A temperature sensor may be used for a variety of other purposes. In some examples, a BMI may be estimated from temperature. For example, lower temperatures tend to correlate with higher BMI. An estimated BMI value may be shared with other applications. For example, a decision support system may use BMI as an input for a model or algorithm to determine guidance for a subject (e.g., glucose correction dose, recommendation to exercise, or eat an amount or type of carbohydrates or food.)

In some examples, an alarm or alert may be triggered when a temperature sensor indicates a temperature that satisfies a condition. For example, an alarm or alert may be triggered when a temperature sensor indicates a temperature that meets a statistical condition (e.g., the temperature is more than one standard deviation away from an average or reference value, or more than a specified number of standard deviations away from an average or reference value). For example, a potentially dangerous or hazardous condition of a patient (e.g., high fever, heat stroke, hypothermia, etc.) may be detected using a subcutaneous temperature sensor, or using a temperature sensor in sensor electronics, and the condition may be communicated via the alarm or alert (e.g., via the subject's smart device, or communicated to a caretaker's smart device through a wireless network or the internet.) In other examples, a potentially overheating or excessively cold sensor or sensor electronics may be detected. In some examples, a potentially faulty temperature sensor may be identified based upon a temperature sensor signal satisfying a condition (e.g., when the temperature sensor indicates a temperature in an unlikely range.)

In various examples, temperature compensation, as described herein, may be utilized in conjunction with analyte sensors for measuring analytes other than glucose. The temperature compensation techniques may be used with analyte sensors for measuring any analytes, including the example analytes described herein.

Also, in some examples, the temperature measured by a subcutaneous temperature sensor, or using a temperature sensor in sensor electronics as described herein may be used to determine an insulin dosage recommendation. For example, the host's body may utilize insulin differently depending on temperature. A temperature related adjustment may be made to the host's insulin dose based on the measured temperature.

Detecting Sensor Disconnection or Re-Use of a Disposable Sensor.

Disconnection of a sensor, or reuse ("restart") of a disposable sensor, may be detected based at least in part on a temperature change, or absence thereof. Some analyte-based sensor systems may be configured with a disposable (replaceable) sensor component and a reusable sensor electronics package, e.g., CGM transmitter, that may be mechanically and electrically coupled to the disposable sensor component. The disposable sensor component may be designed to extend into a subcutaneous layer of a host, and to work for a period of days (e.g., 7, 10, or 14 days), after which the disposable sensor component is to be removed and replaced with a new disposable sensor component. As described in detail in discussion of FIG. 1, the reusable transmitter may be wirelessly coupled to a control device (e.g., smart device), which may include a user interface for entering commands that may be sent to the transmitter. The user interface on the control device may allow for stopping a sensor session, and starting a new sensor session.

A sensor session may be programmed for a defined time period (e.g., 7 days), after which the session expires (if not manually stopped via the user interface). After a sensor session expires or is stopped, a new session may be started via the user interface.

In some instances, a subject (e.g., patient) may start a new sensor session without replacing the disposable sensor component, i.e. the subject may "restart" a session with the same disposable component that was in use prior to stopping the session. For a variety of reasons, it may be useful to detect such a restart event.

A sensor "restart" may be detected based at least in part on a signal from a temperature sensor in a sensor electronics package (e.g., CGM transmitter). For example, if a subject intends to reuse a disposable sensor component, the subject typically will stop a sensor session and start a new session without removing the transmitter from the disposable component. This "restart" scenario may be detected from the absence of a temperature signature associated with removal of the transmitter from a sensor.

Figure 18A:
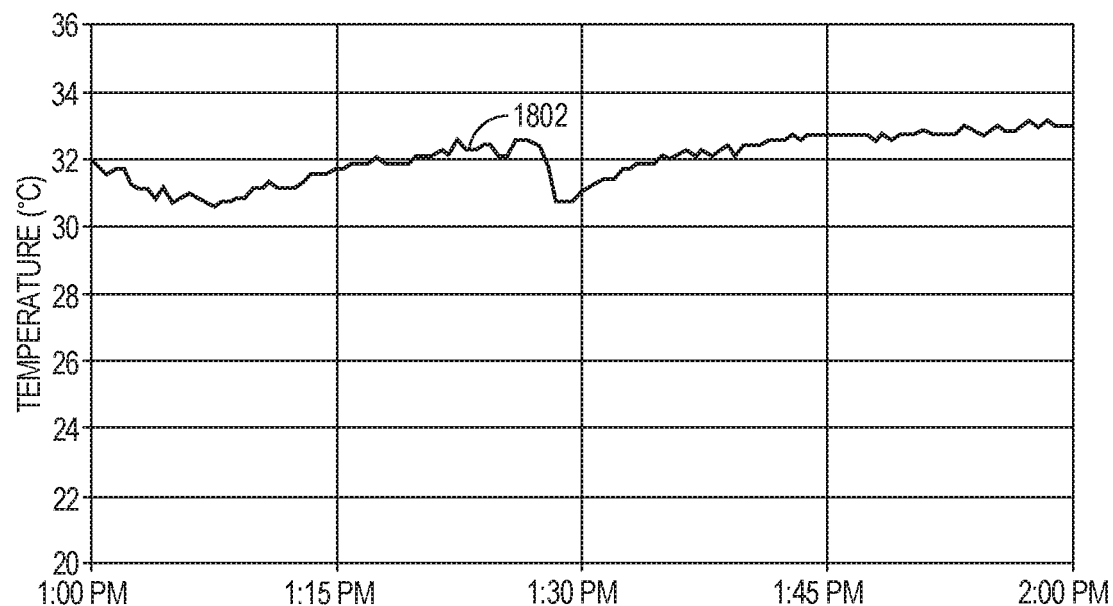
FIG. 18A is a plot of temperature vs. time, where a sensor electronics package was removed from a sensor for a period of one minute.
Figure 18B:
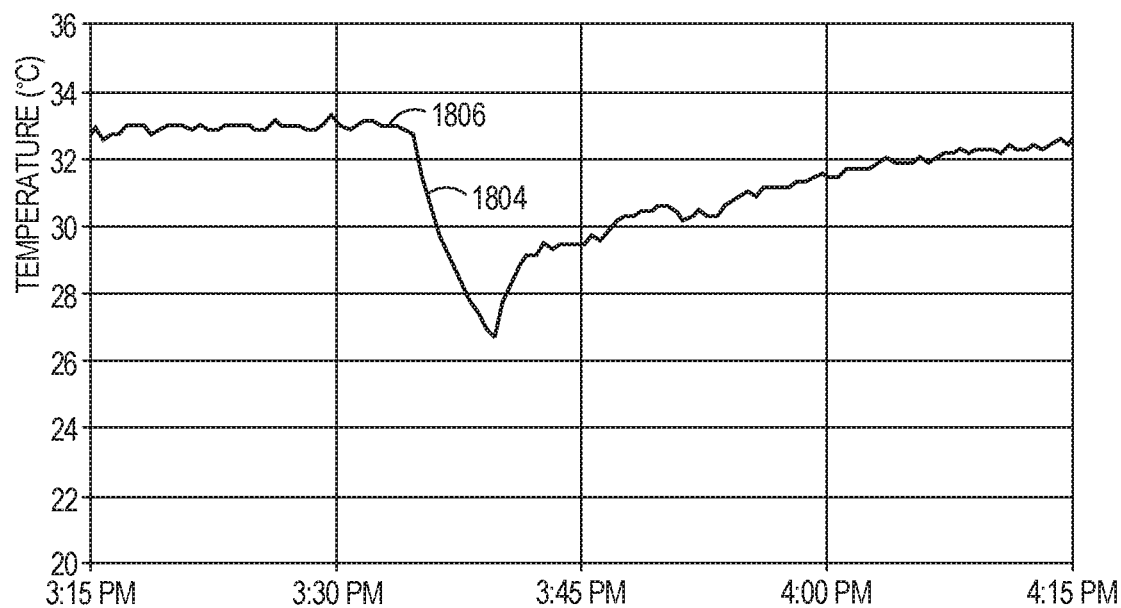
FIG. 18B is a plot of temperature vs. time, where a sensor electronics package was removed from a sensor for a period of five minutes.

When the transmitter is removed from a host and reconnected to a new sensor, a temperature signature that includes a temperature drop is observable if the sensor electronics are off the host for a sufficient period of time (e.g., one minute). FIG. 18A is a plot of temperature vs. time, where a sensor electronics package (Dexcom CGM transmitter) was removed from a sensor (Dexcom glucose sensor) for a period of one minute at 1:27 PM. A temperature drop 1802 is visible in the temperature plot. FIG. 18B is a similar graph, in which the sensor electronics package was removed for five minutes at 3:34 PM. A larger temperature drop 1804 is visible in the temperature plot, and the sensor takes over half an hour to trend back to the steady state temperature 1806 (about 33° C.) that was detected prior to the change.

In various examples, a disconnection event (e.g., removing a CGM transmitter from a sensor) may be identified based upon an amount of temperature drop (e.g., 3° C. or 5° C. in a short period), the slope of the drop, or the consistency (smoothness or lack of variability) in a signal during the drop, or a combination thereof.

A sensor restart may be identified from an absence of a disconnection event around the time of a session stop or start. In some examples, a disconnection event may be determined from a temperature signature (e.g., temperature drop) in combination with other information, such as a stopping of a sensor session. For example, when a temperature signature associated with disconnection occurs soon after (or shortly before) a session is ended, it may be inferred that the sensor electronics was removed from a disposable sensor. And when a sensor session is stopped and started, but a temperature drop, as described above and illustrated in FIGS. 18A and 18B, is not present, it can be inferred that a disposable sensor was re-used, because changing to a new sensor requires removal of the sensor electronics (CGM transmitter) from the sensor. In some examples, sensor removal may be determined from a temperature signature in combination with accelerometer data (e.g., rapid or large movements, which may occur during disconnection of a transmitter, followed by a temperature drop) or other sensor data.

Figure 13:
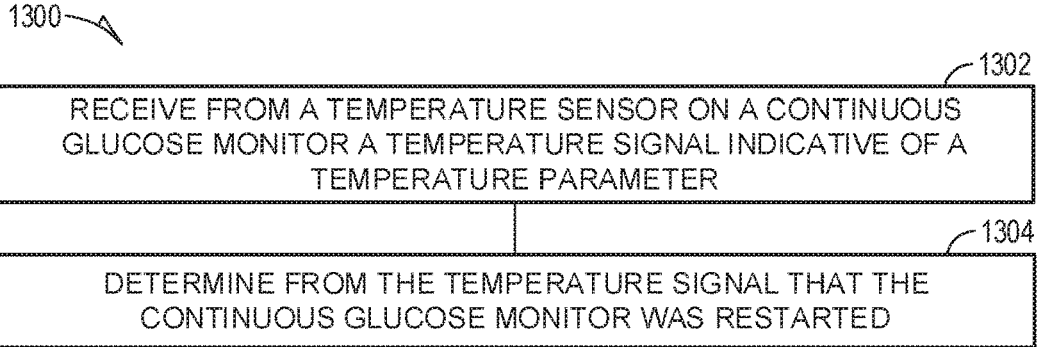
FIG. 13 is a flowchart illustration of an example method of determining that a continuous glucose (or other analyte) monitor was restarted.

FIG. 13 is a flowchart illustration of an example method 1300 of determining that a continuous glucose (or other analyte) monitor was restarted. The method 1300 may include, at 1302, receiving from a temperature sensor on a continuous glucose monitor a temperature signal indicative of a temperature parameter. The method 1300 may further include determining from the temperature signal that the continuous glucose monitor was restarted. For example, as described above, a restart may be identified from a lack of a disconnection event in a temperature signature, optionally in combination with other sensor information.

A restart may also be detected using a subcutaneous temperature sensor. When a temperature sensor is on a subcutaneous analyte sensor, the temperature reading from the sensor will typically be lower than body temperature (e.g., closer to an ambient air temperature) when the sensor is first inserted, and the detected temperature may be expected to gradually ramp up to body temperature as the sensor absorbs heat from the body. In an example, determining from the temperature signal that the continuous glucose monitor was restarted may include comparing a first temperature signal value prior to a sensor initiation to a second temperature signal value after sensor initiation, and declaring that the continuous glucose monitor was restarted when comparison satisfies a similarity condition. The similarity condition may include a temperature range. For example, when a sensor is restarted (as opposed to replaced), the temperature at the subcutaneous sensor will typically not change, or any change will be gradual. When a sensor is replaced, a more significant temperature change may occur (e.g., the new sensor may show a different temperature than the old sensor.)

Determining Anatomical Location

Figure 16:
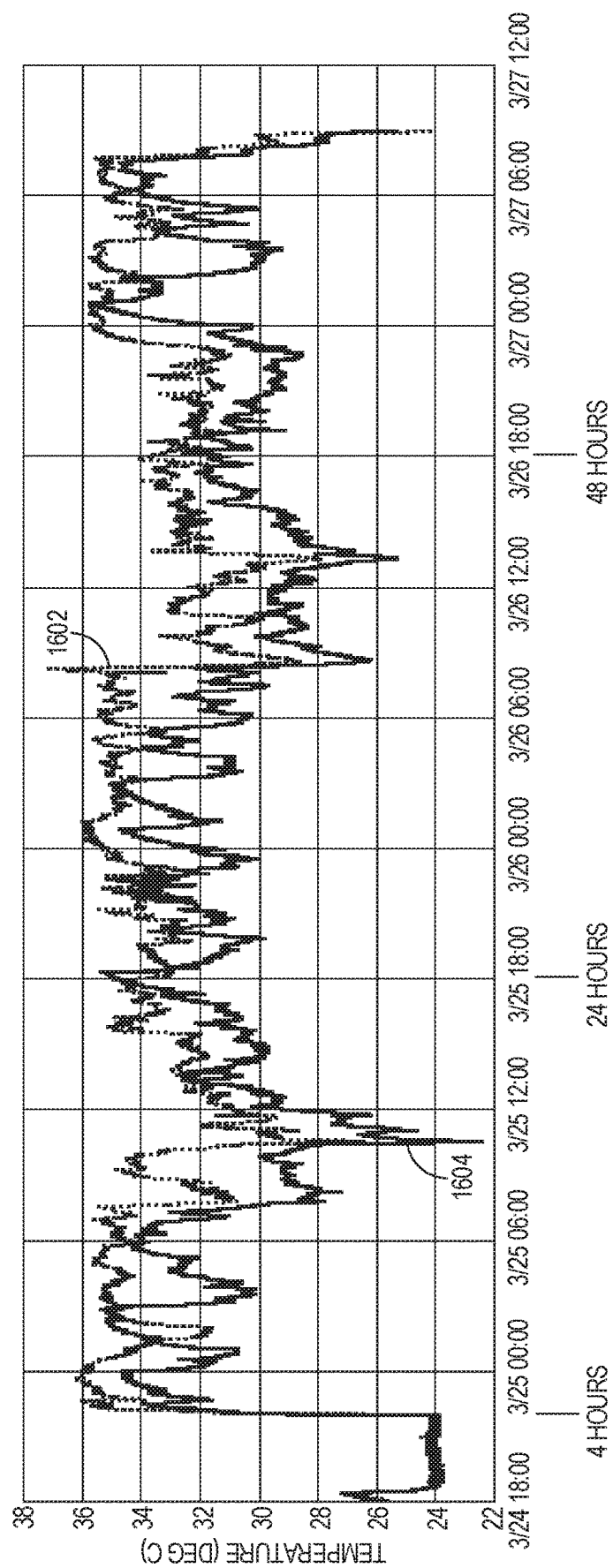
FIG. 16 is a graphical illustration that shows plots of temperature vs. time for a sensor on an abdomen of a host and a sensor on an arm of the host.
Figure 17:
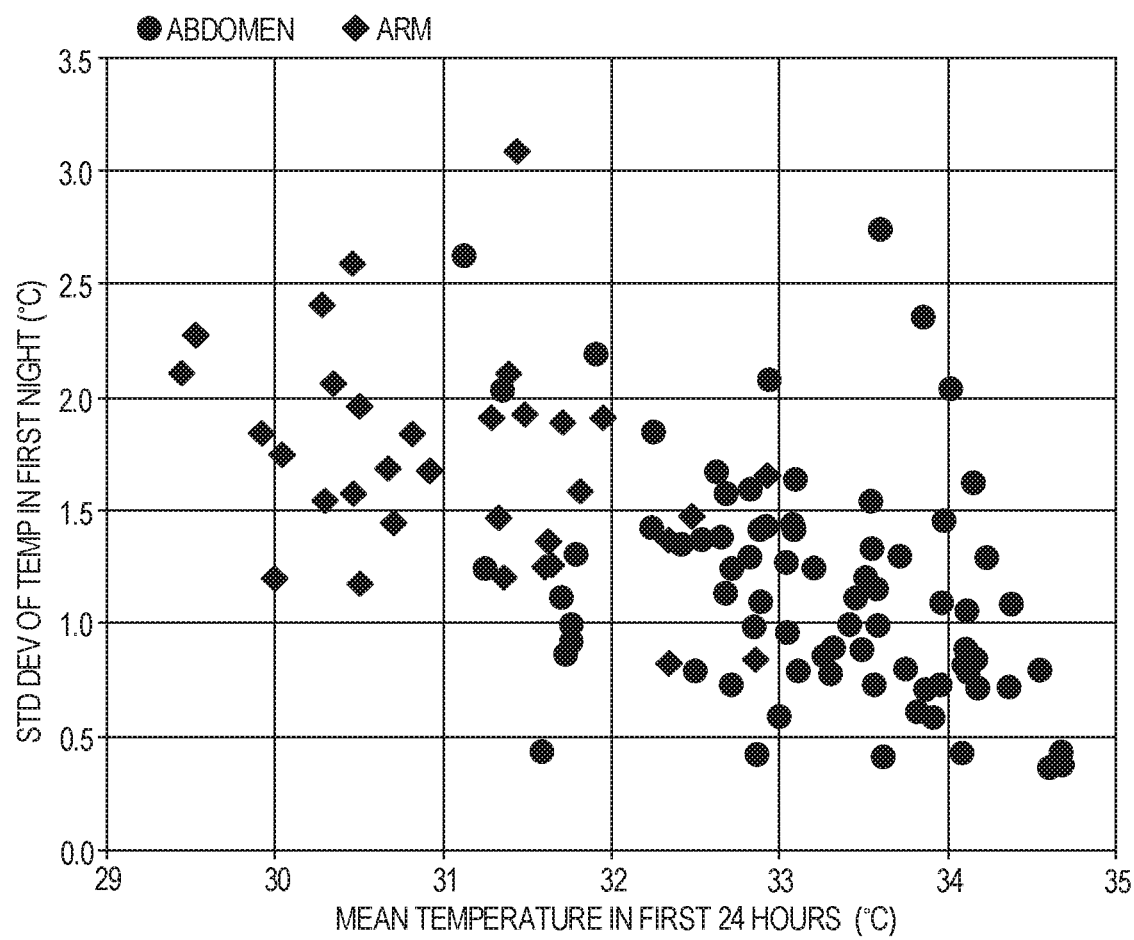
FIG. 17 is a plot of standard deviation vs. mean temperature over the first 24 hours for a number of sensor devices.

In some examples, temperature information may be used to determine an anatomical location where a sensor is worn, or a type of anatomical location. For example, a sensor may be worn on an arm, or on an abdomen. A sensor (or sensor electronics) may experience colder temperatures when worn on the arm compared to the abdomen. This may, for example be driven by the fact that the upper arm is farther away from the core body, or the fact that that the arm is more likely to be exposed to air, e.g., when short sleeve clothing is worn. A sensor worn on an arm may also experience more variability in temperature, especially during sleep (e.g., when the arm is more likely than the abdomen to be outside of any sheets or blankets at least part of the night). In some examples, an anatomical location may be determined based on an average (e.g., mean or median) temperature during a specified period (e.g., during the first 24 hours of wear.) For example, a sensor device location may be declared as on the abdomen when an average temperature satisfies a condition, such as when the average temperature exceeds a specified temperature threshold (e.g., 32° C.). In another example, e.g., an abdomen sensor location may be detected based upon a variability condition, e.g., a first standard deviation of temperature variation during a specified period (e.g., a night or a period of sleep) being less than a specified amount (e.g., less than 1° C.). In some examples, an abdomen location may be detected based upon a combination of a temperature condition and a variability condition, e.g., an abdomen location may be declared when the average temperature exceeds a specified temperature threshold (e.g., 32° C.) or when a first standard deviation of temperature variation during a specified period is less than a specified amount (e.g., less than 1° C.) FIG. 16 is a graphical illustration that shows plots of temperature (y-axis) vs. time (x-axis) for two sensors. A first plot 1602 (dotted line) shows data from a sensor placed on the abdomen. A second plot 1604 (solid line) shows data from a sensor placed on an arm. For the first four hours, the sensor is not worn by a host (e.g., not yet inserted), and the data from the sensors is roughly correlated. After 4 hours, the sensor is inserted into a host, and the temperature rapidly rises. After this transition, variations between the first plot 1602 and second plot 1604 are evident, as the second plot 1604 (which corresponds with the arm-mounted sensor) shows lower temperatures, and higher variability. FIG. 17 is a plot of standard deviation vs. mean temperature over the first 24 hours for several dozen sensor devices. Using the method discussed above (SD>1.0 and mean temp <32° C.) identified sensor devices located on an arm with high sensitivity (all but five arm-mounted sensors identified as such) and good specificity (just six abdomen-mounted sensors identified as on the arm according to the method.) In some examples, the example temperature methods may be combined with information from other sensors (e.g., accelerometer data) to further increase the sensitivity and specificity. In some examples, a learned model (e.g., using a neural network) may be used to identify patterns or relationships and the model may be applied to determine location. Such an approach may achieve higher sensitivity or specificity. While specific "arm" and "abdomen" locations are shown, other locations or classes may also be used (e.g., a lower back location may be determined, or a "torso" location may include both abdomen and lower back)

Figure 14:
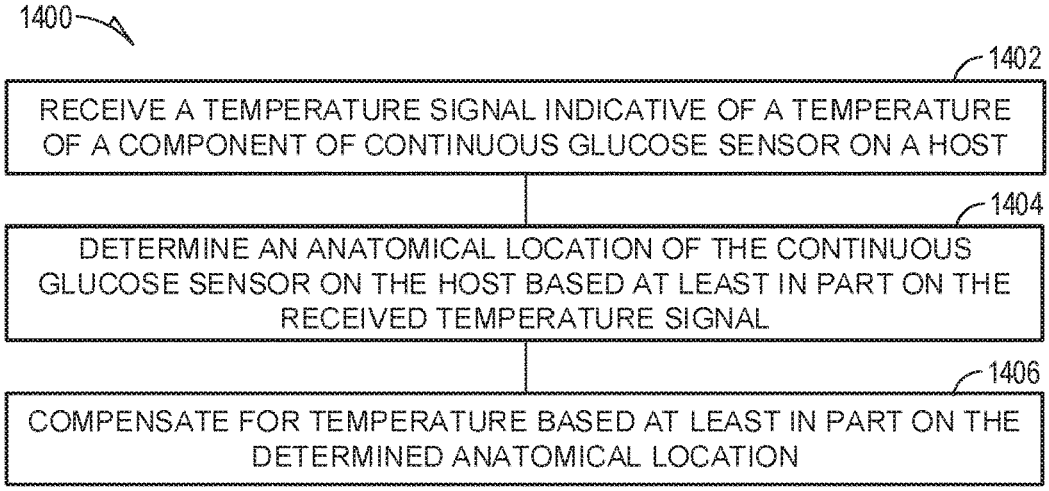
FIG. 14 is a flowchart illustration of an example method of determining an anatomical location of a sensor.

FIG. 14 is a flowchart illustration of an example 1400 method of determining an anatomical location of a sensor. The method may include at 1402 receiving a temperature signal indicative of a temperature of a component of a continuous glucose sensor on a host. The method may include at 1404 determining an anatomical location of the continuous glucose sensor on the host based at least in part on the received temperature signal. In some examples, the anatomical location may be determined at least in part based on a sensed temperature. In some examples, the anatomical location may be determined based at least in part on a variability of the temperature signal. For example, greater temperature variability may be seen in a sensor inserted at a peripheral location (e.g., on an arm) or inserted at a location that is less likely to be covered on clothing than a sensor inserted on the abdomen or lower back. In some examples, the method may further include receiving an accelerometer signal, and determining an anatomical location may include determining the anatomical location based on the accelerometer signal. For example, a higher activity level or more frequent change in posture (either of which may be determined from accelerometer signal) may indicate a peripheral location (e.g., on the back of an arm), and a lower activity level, or less frequent change in posture, or more cyclical change in posture (e.g., correlating with sleep or sitting) may indicate an abdominal or lower back location. In some examples, a distribution of rate of change of position may be used to identify an anatomical location. For example, a distribution biased toward a higher rate of change may suggest a peripheral location (e.g. on an arm), and a distribution biased toward a lower rate of change may suggest a location on the torso (e.g., abdomen.) In another example, a neural network or other learned model may be used to learn patterns or relationships that may be used to determine or predict an anatomical location (e.g., using sensor data and optionally based on user-entered data indicating a specified anatomical location.)

At 1406, in some examples, temperature compensation may be based at least in part on the anatomical location. For example, a temperature compensation algorithm may account for the fact that a subcutaneous temperature in the abdomen or lower back may change more slowly than a subcutaneous temperature in an arm, which may have a lower mass to act as a heat sink or heat source.

Compression Detection.

In some examples, compression may be detected based at least in part on a signal from a temperature sensor. Compression of a sensor may occur, for example, when a person lies or leans on a sensor, which may happen during sleep, for example. Compression of a glucose sensor can generate lower-than-actual estimated glucose values. When a subject lies on a glucose sensor, the temperature of the sensor may be raised. Compression of the sensor may be detected based at least in part on a rise in temperature of the sensor. In an example, a rapid drop in a glucose level that is simultaneous with or followed by an increase in temperature may indicate that the sensor is being compressed. In some examples, additional information, such as activity information may be used in combination with temperature. For example, a rapid drop in estimated glucose in combination with low activity (suggesting the subject is not exercising) and a rise in sensor temperature (suggesting that the subject is lying on the sensor) may indicate a compression low. In some examples, an alert may be triggered in response to a possible compression low. For example, a notification may be delivered via a smart device, or a sound may be emitted from a smart device or from a sensor, which may prompt the subject to move off the sensor to permit accurate estimated glucose concentration levels to be obtained.

Sleep Detection

In some examples, sleep may be detected based at least in part on temperature sensor information. For example, warmer temperatures may be observed during sleep. More consistent temperatures or temperature patterns may be observed in sleep. Sleep may be detected by applying a model or algorithm to detect periods of warm temperature, consistent temperatures, or temperature patterns (e.g., a binary pattern corresponding to a covered or not covered arm sensor), optionally in combination with other sensor information. In some examples, temperature information may be used in combination with posture information from a 3D accelerometer, activity information, respiration, or heart rate, or any combination thereof, to detect sleep. In some examples, alert behaviors may be changed in response to sleep detection. For example, alert threshold may be adjusted to reduce the number of alerts during sleep, or alert triggers may be adjusted to provide time to treat hypoglycemic events, or only certain types of alerts (e.g., more urgent alerts) may generate sound when sleep is detected.

In some examples, compression detection, compensation, or alerts may be provided or modified during sleep. For example, when a person is sleeping and an estimated glucose value suddenly drops rapidly, compression may be inferred based on the sleeping state and the sudden drop in estimated glucose value, optionally in combination with other information, such as a discontinuity in a glucose curve, a rise in temperature, or other information.

Additional Example Temperature Sensors

In some examples, it is desirable to reduce the cost of hardware included in an analyte sensor system, such as the analyte sensor system 8 of FIG. 1. For example, components of the analyte sensor system 8, such as all or part the sensor electronics 12 and/or continuous analyte sensor 10 may be disposable products used for a sensor session lasting a few days and then discarded. Accordingly, it may be desirable to obtain highly accurate temperature values from inexpensive temperature sensors.

Various examples described herein are directed to systems and methods that utilize a trained temperature compensation model to generate compensated temperature values from a system temperature sensor. The trained temperature compensation model, in some examples, can compensate for factors leading to error in raw temperature data such as, for example, noise or other nonlinearities. Utilizing a trained model to compensate temperature values from a system temperature sensor, as described herein, may generate acceptably accurate temperature values using less expensive or more readily available system temperature sensors. For example, using a trained model, as described herein can, in some examples, can allow the use of a less expensive or more readily available temperature sensor, such as a sensor that is included with or generated from a suitable diode at an Application Specific Integrated Circuit (ASIC) or other component of the analyte sensor system 8.

The temperature compensation model can be any suitable type of model including, for example, a neural network, state model, or any other suitable trained model. Inputs to the temperature compensation model can include, for example, raw temperature data and uncompensated temperature data. Raw temperature data includes data generated by the system temperature sensor to indicate temperature such as, for example, a current, a voltage, a count, etc. Uncompensated temperature data can include data that indicates an uncompensated temperature. For example, a temperature sensor, in some examples, provides data indicating a temperature derived from raw temperature data. In some examples, input to the temperature compensation model can include both raw temperature data and uncompensated temperature data. In some examples, the output of the temperature compensation model can include a compensated temperature value.

In some examples, in addition to or instead of a compensated temperature value, the output of the temperature compensation model can include sensor properties that describe a relationship between raw temperature data generated by the system temperature sensor and corresponding temperature values. For example, the output of the temperature compensation model can include a slope and an offset. The slope and offset can be applied to raw temperature data generated by the system temperature sensor to generate the compensated temperature value.

Figure 24:
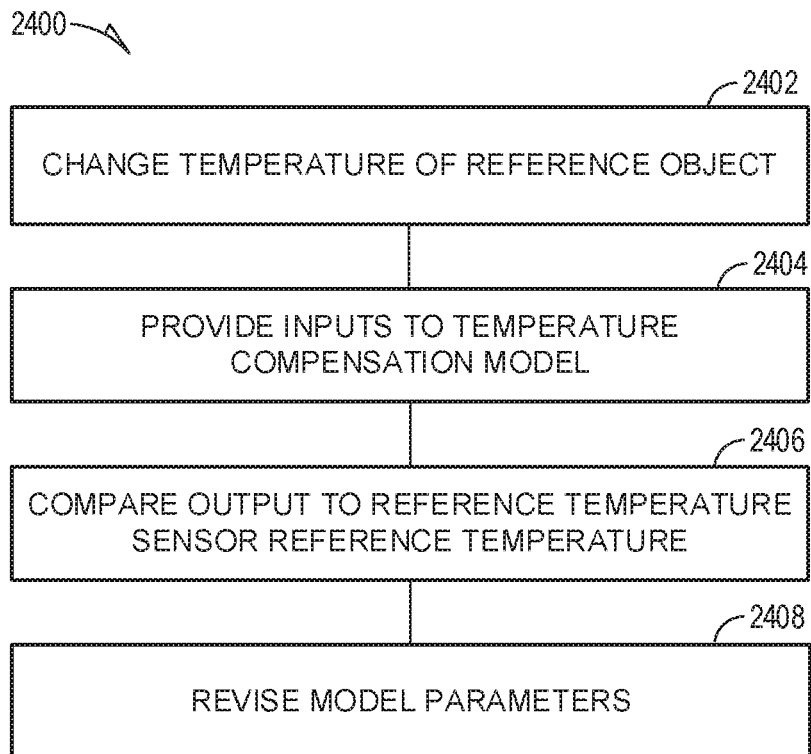
FIG. 24 is a flowchart illustration of an example method for training a temperature compensation model.

The temperature compensation model can be trained, for example, utilizing a reference temperature sensor that is more accurate than the system temperature sensor. FIG. 24 is a flowchart illustration of an example method 2400 for training a temperature compensation model. The system temperature sensor and reference temperature sensor can be positioned to measure the temperature of an object such as, for example, a surface, an amount of liquid in a container, etc. At 2402, the object is heated and/or cooled to a first temperature. When the object is at various temperatures, inputs may be provided to the temperature compensation model at 2404. In response to the inputs, the temperature compensation model generates one or more model outputs. The one or more model outputs are compared to a reference temperature measured by the reference temperature sensor at 2406.

At 2408, the model parameters are modified based on an error between the reference temperature and the output of the temperature compensation model. The error indicates a difference between a compensated temperature value that is a model output and/or is generated using the model outputs and the reference temperature. The error is used to modify parameters of the model. The method 2400 may be executed and repeated, for example, until the model converges. The model may converge when the error for the temperature compensation model is consistently within an acceptable range. In some examples, a temperature compensation model is trained for each analyte sensor system 8. In other examples, analyte sensor systems 8 and associated system temperature sensors may have similar properties allowing a temperature compensation model trained on one analyte sensor system 8 to be used on other analyte sensor systems 8, such as, for examples, other analyte sensor systems 8 having similar components to the analyte sensor system 8 used to train the model, other analyte sensor systems 8 manufactured in the same batch as the analyte sensor system 8 used to train the model, etc.

Figure 25:
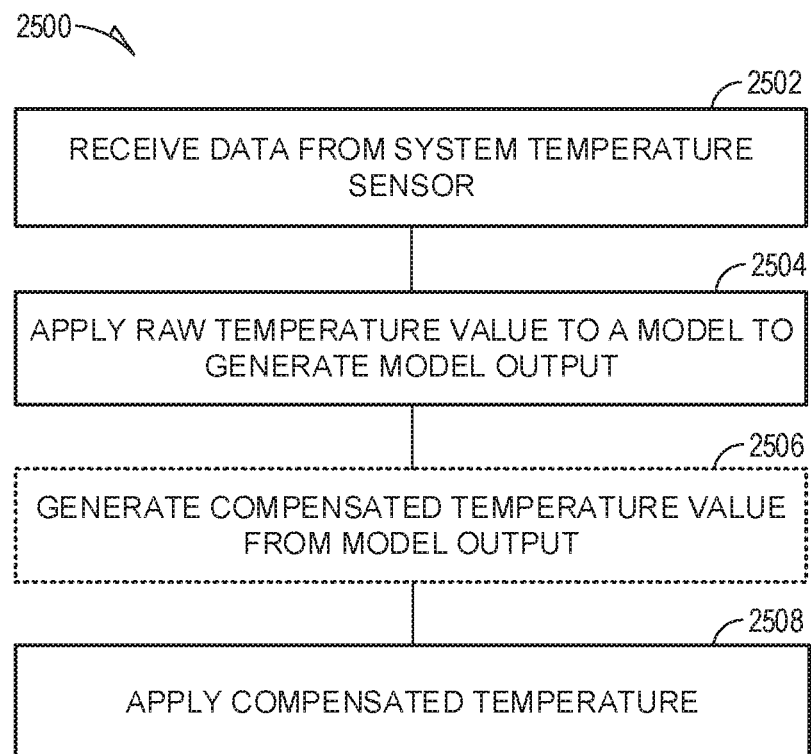
FIG. 25 is a flowchart illustration of an example method for utilizing a trained temperature compensation model.

FIG. 25 is a flowchart illustration of an example method 2500 for utilizing a trained temperature compensation model. At 2502, data is received from the system temperature sensor. The data can include, for example, raw temperature data and/or uncompensated temperature data. At 2504, the data received from the system temperature sensor is applied to the model to generate one or more model outputs. Model outputs can include compensated temperature values and/or system temperature sensor parameters, such as slope and offset, that may be used to generate compensated temperature values.

Optionally, at 2506, model outputs are used to generate a compensated temperature value. Generating the compensated temperature value at operation 2506 can be omitted, for example, if the model outputs include a compensated temperature value and/or if the model outputs do not include system temperature sensor parameters. At 2508, the compensated temperature value is applied. For example, the compensated temperature value may be applied in any of the ways described herein for utilizing temperature in conjunction with an analyte sensor.

In some examples, operations 2502 and 2504 are performed, for example, at the beginning of a sensor session using a portion of raw sensor data received from the sensor. Applying the raw temperature value to the model may yield system temperature parameters, such as slope and offset. The system temperature parameters are applied to subsequently received raw sensor data to generate subsequent compensated temperature values.

As described herein, the exercise state of the host can affect the temperature compensation model to be applied to generate a temperature compensated glucose concentration. The exercise state of the host can be determined in various different ways including, for example, utilizing a third sensor signal as described herein with respect to FIG. 7. In some examples, other techniques may be used to detect an exercise state in addition to or instead of using a third sensor.

Figure 26:
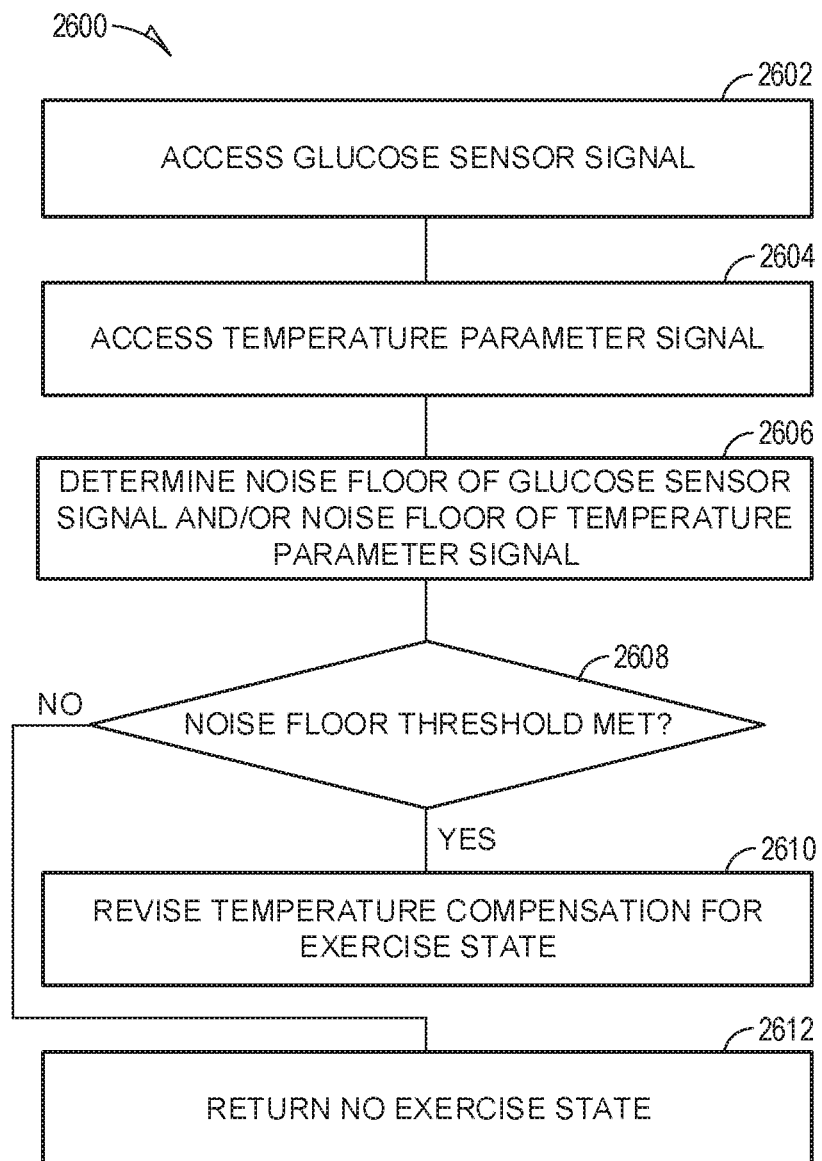
FIG. 26 is a flowchart illustration of an example method for detecting an exercise state.

FIG. 26 is a flowchart illustration of an example method 2600 for detecting an exercise state. The example method 2600 detects an exercise state of the host by examining a noise floor of the glucose sensor signal, a noise floor of the temperature parameter signal, or both. A noise floor is a level of noise associated with a signal. For example, the noise floor may be the sum of noise sources in a signal other than the value of interest. For example, the noise floor of a glucose sensor signal is the sum of noise sources in the signal other than glucose. The noise floor of a temperature parameter signal is the sum of noise sources in the temperature parameter other than indications of temperature. In some examples, when the host is in an exercise state, the physiological behavior associated with exercise manifest in additional noise sources that affect the glucose sensor signal and/or the temperature parameter signal. Accordingly, the method 2600 detects an exercise state by measuring the respective noise floors. The method 2600 can be executed at an analyte sensor system 8 such as, for example, at sensor electronics 12 and/or at a display device 14, 16, 20.

The method 2600 may include, at 2602, accessing a glucose sensor signal. For example, the glucose sensor signal may be received from a continuous glucose monitor (CGM). The method 2600 may include at 2604 accessing a temperature parameter signal. Accessing the temperature parameter signal may include, for example, receiving a signal indicative of a temperature, a temperature change, and/or a temperature offset.

The method 2600 may include, at operation 2606, determining a noise floor of the glucose sensor signal, the temperature parameter signal, or both. The noise floor or floors may be determined in any suitable way. In some examples, the noise floor of a signal can be approximated by finding the lowest value of the signal. In another example, the noise floor of a signal can be found using spectral analysis.

The method 2600 may include, at 2608, determining if a noise floor threshold is met. In some examples, the threshold at 2610 is met if noise floor of the glucose sensor signal is greater than a first threshold or if the noise floor of the temperature parameter signal is greater than a second threshold. In some examples, the threshold at 2610 is met if noise floor of the glucose sensor signal is greater than a first threshold and the noise floor of the temperature parameter signal is greater than a second threshold.

If the noise floor threshold is met, then the host is in an exercise state. Accordingly, the method 2600 includes, at 2610, revising a temperature compensation based on the temperature parameter signal to account the exercise state. Examples of how this can be performed is described herein with respect to the method 700 (e.g., 708 and 710) as well the method 800 (806). For example, as described herein, the temperature parameter signal may be applied to an exercise model before it is used to generate a temperature compensated glucose concentration. If the noise floor threshold is not met, the host may not be in an exercise state, and an indication of no exercise state may be returned at 2612. Alternatively, in lieu of sending an indication of no exercise state, the method 2600 at 2612 may instead refrain from revising temperature compensation.

Figure 27:
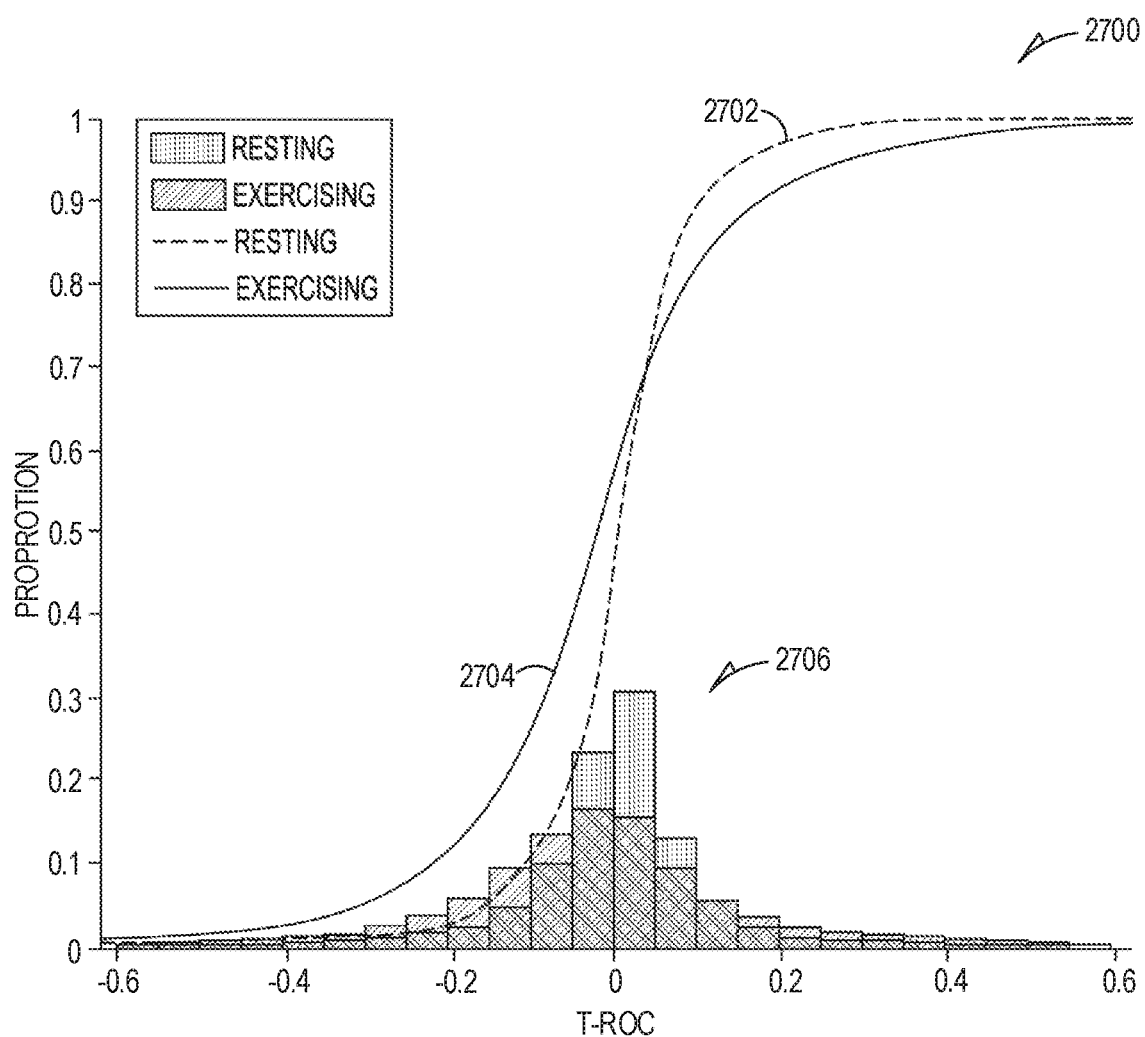
FIG. 27 is graph showing a first change distribution function showing a host in a resting (e.g., not exercise) state and a second change distribution function showing a host in an exercise state.

As described herein, detecting that the host is in an exercise state based on a rate of change of a temperature parameter. In some examples, this can be performed using a change distribution function. A change distribution function indicates a distribution of rates of change over successive samples of a signal. FIG. 27 is graph 2700 showing a first change distribution function 2702 showing a host in a resting (e.g., not exercise) state and a second change distribution function 2704 showing a host in an exercise state. In the graph 2700, the horizontal axis indicates a rate of change in a temperature signal indicating the subcutaneous temperature at a glucose sensor. The vertical axis indications a cumulative distribution of rates of change. As shown, the cumulative distribution function 2702 is about centered on a zero rate of change, meaning that about half of the rates of change between successive samples are greater than zero and about half are less than zero. The cumulative distribution function 704 skews low, meaning that when the host is in the exercise state, more of the rates of change are less than zero that are greater than zero. This can be exploited, as described herein, by examining rates of change between temperature parameter signal samples, such as the example histogram 2706.

Figure 28:
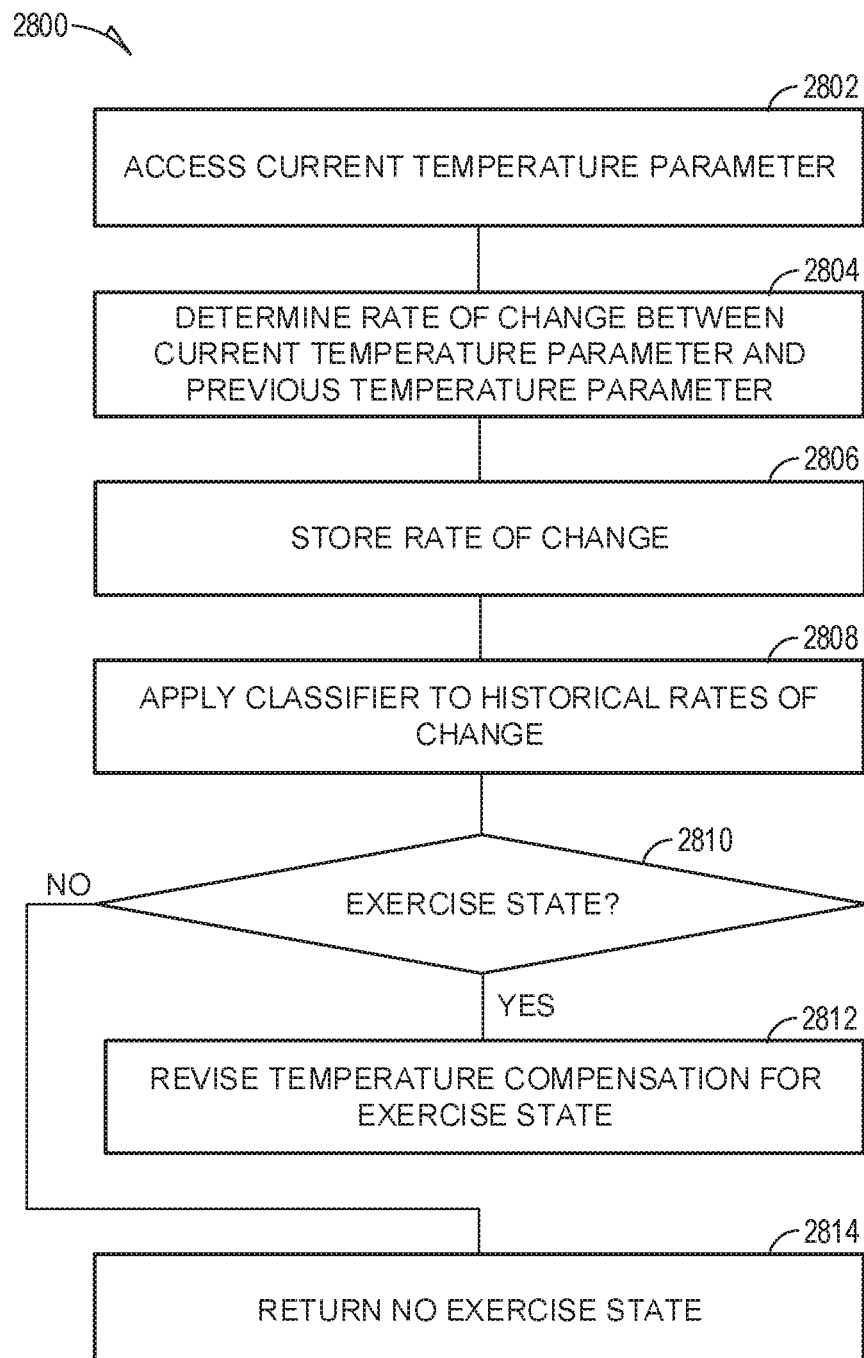
FIG. 28 is a flowchart illustration of an example method for detecting an exercise state using a distribution of rates of change in a temperature parameter signal sample.

FIG. 28 is a flowchart illustration of an example method 2800 for detecting an exercise state using a distribution of rates of change in a temperature parameter signal sample. The method 2800 can be executed at an analyte sensor system 8 such as, for example, at sensor electronics 12 and/or at a display device 14, 16, 20.

The method 2800 may include, at 2802 accessing a current temperature parameter signal sample. The method 2800 may include, at 2804, determining a rate of change between the current temperature parameter signal sample and a previous temperature parameter signal sample. The rate of change can be the difference. As described herein, the rate of change can be negative (e.g., if the current sample is less than the previous sample) or positive (e.g., if the current sample is more than the previous sample). The method 2800 may include, at 2806, storing the current rate of change.

At 2808, a classifier is applied to historical rates of change including the newly stored rate of change. The classifier, for example, can represent a distribution of rates of change over a predetermined number of samples (e.g., 30 samples). The measured distribution of rates of change over the predetermined number of samples is compared to the classifier. At 2810, it is determined whether the measured distribution of rates of change meets the classifier. For example, the classifier may describe a number or range of numbers of measured rates of change between samples that fall into a number of ranges. An example, classifier is provided by TABLE 3 below:

TABLE 3

| <−0.4 | −0.4->−0.2 | −0.2->0.2 | 0.2-0.4 | >0.4 |
|---|---|---|---|---|
| >2 | >10 | >10 | <5 | <2 |

In the example of TABLE 3, a measure distribution of rates of change meets the classifier if the number of measured rates of change less than −0.4° C./min is greater than 2, the number of measured rates of change between −0.4 and −0.2° C./min is greater than 10, and so on.

If the classifier is met, then the host is in an exercise state. Accordingly, the method 2800 includes, at 2612, revising a temperature compensation based on the temperature parameter signal to account the exercise state. Examples of how this can be performed is described herein with respect to the method 700 (e.g., 708 and 710) as well the method 800 (806). For example, as described herein, the temperature parameter signal may be applied to an exercise model before it is used to generate a temperature compensated glucose concentration. If the classifier is not met, the host may not be in an exercise state, and an indication of no exercise state may be returned at 2614. Alternatively, in lieu of sending an indication of no exercise state, the method 2600 at 2614 may instead refrain from revising temperature compensation.

In some examples, any of the various temperature sensor arrangements described herein can be used to measure the temperature of an analyte sensor during storage and/or shipping. For example, the peak temperature that an analyte sensor is exposed to prior to a sensor session may affect the performance of the sensor. For example, the peak temperature to which an analyte sensor is exposed prior to a sensor session may affect an initial sensitivity and/or baseline for the analyte sensor upon insertion into the skin of a host. Also, in some examples, if the peak sensor to which the analyte sensor is exposed is too high, the sensor may no longer be suitable for use.

Figure 29:
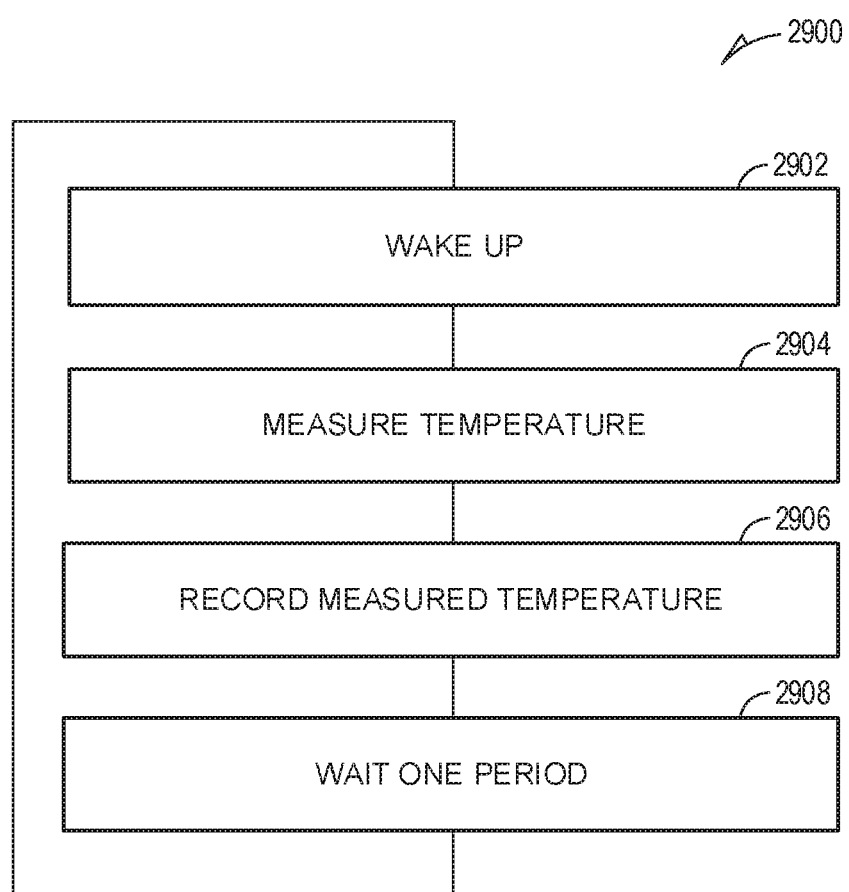
FIG. 29 is a flowchart illustration of an example method for recording temperatures at an analyte sensor system during shipment.

In various examples, an analyte sensor system, such as the analyte sensor system 8 of FIG. 1, is configured to use one or more of the various sensor arrangements described herein to periodically record the temperature at the analyte sensor system during storage and/or transport. FIG. 29 is a flowchart illustration of an example method 2900 for recording temperatures at an analyte sensor system during shipment. The analyte sensor system (e.g., sensor electronics 12 thereof) can be programmed to execute the method 2900, for example, while the analyte sensor system is packaged for storage and/or transport.

The method 2900 may include, at 2902, the analyte sensor system waking up. For example, a processor of the analyte sensor system may be programmed to wake up periodically, as described herein. Upon waking up, the analyte sensor system may measure a current temperature at 2904. The analyte sensor system may include any of the temperature sensor arrangements described herein and may use one or more temperature sensor arrangements to measure a temperature at 2904. The analyte sensor system may record the measured temperature at 2906. The measured temperature may be recorded, for example, at a data storage memory (e.g., 220 in FIG. 2) or another suitable data storage location at the analyte sensor system. At 2908, the analyte sensor system waits one period. One period may be, for example, 10 minutes, one hour, one day, etc. Upon waiting one period, the analyte sensor system returns to 2902 and again wakes up as described.

The analyte sensor system may execute the method 2900 while it is stored and/or transported to a host for use. In this way, the analyte sensor system may arrive at the host to begin a sensor session with a record of periodic temperature measurements stored at a data storage memory.

Figure 30:
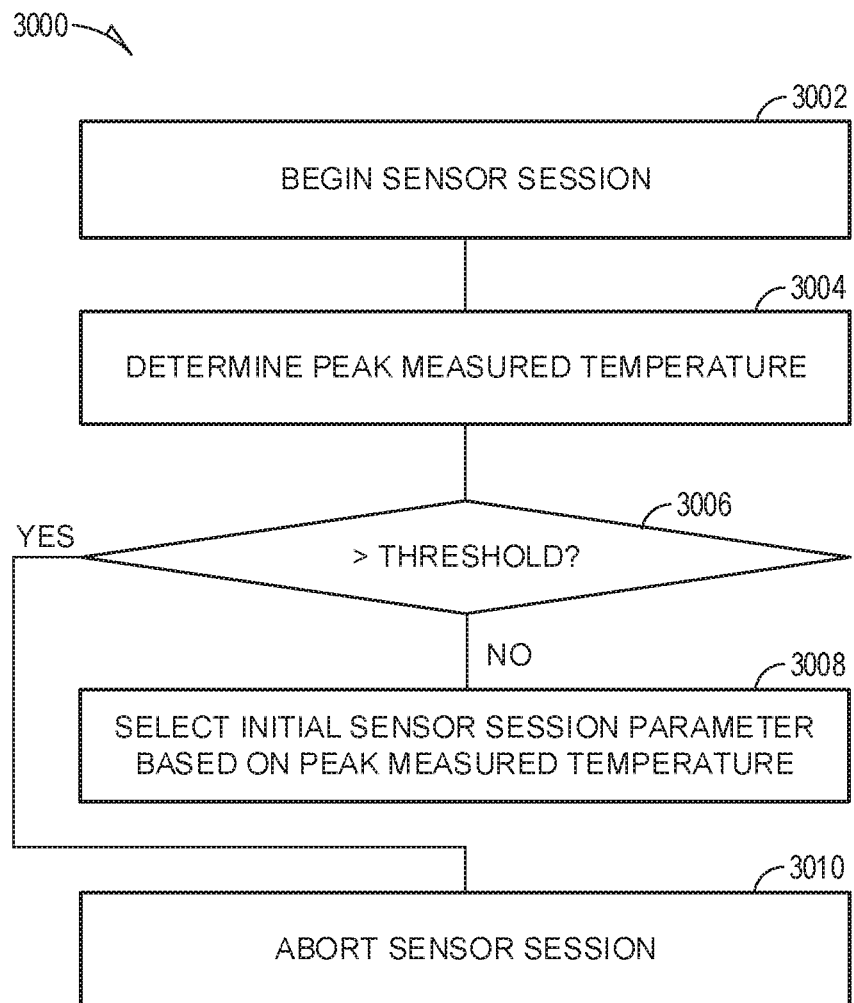
FIG. 30 is a flowchart illustration of an example method for beginning a sensor session with an analyte sensor session including a record of periodic temperature measurements from transport and/or storage of the analyte sensor system.

FIG. 30 is a flowchart illustration of an example method 3000 for beginning a sensor session with an analyte sensor session including a record of periodic temperature measurements from transport and/or storage of the analyte sensor system. At 3002, the analyte sensor system begins a sensor session. This may occur, for example, when an analyte sensor of the analyte sensor system is positioned at a host, for example, when the analyte sensor is inserted into the host's skin. At 3004, the analyte sensor system determines a peak temperature to which the analyte sensor system was exposed prior to the sensor session. This can include, for example, reading the record of periodic temperature measurements and determining a highest temperature measurement from the record. The highest temperature measurement may be the peak temperature measurement.

At 3006, the analyte sensor system determines if the peak temperature measurement is greater than a threshold. The threshold may be, for example, the highest temperature to which the analyte sensor can be exposed prior to a sensor session without compromising sensor performance during the session. If the peak temperature is greater than the threshold, then the analyte sensor system may abort the sensor session at 3010. This may include, for example, sending a message to one or more display devices, such as display devices 14, 16, 18, and/or 20, indicating that the analyte sensor or sensor system is unsuitable for use and that a different sensor or analyte sensor system should be used.

If the peak temperature is not greater than the threshold at 3006, the analyte sensor system may select an initial sensor session parameter based on the peak temperature. The initial sensor session parameter may be or include, for example, an initial sensitivity, an initial baseline, etc. The initial sensor session parameter may be used by the analyte sensor system, for example, to generate analyte concentration values using raw sensor data. In some example, the initial sensor session parameter is used after a sensor break-in period. In some examples, the analyte sensor applies a trained model to the peak temperature to determine the initial sensor session parameter or parameters. In another example, a relationship between peak temperature and the initial sensor session parameter or parameters is stored at the analyte sensor system, for example, at a look-up table. In some examples, in addition to or instead of a peak temperature, the analyte sensor system may determine an average temperature, median temperature, etc., or other suitable indication of the temperature during packaging.

In some examples, the methods 2900 and/or 3000 include considering humidity in addition to or instead of temperature. For example, referring to the method 2900, the analyte sensor system may measure humidity upon waking up. Humidity can be measured in any suitable way. For example, systems and methods for measuring humidity at an analyte sensor based on the membrane impedance of the sensor are described at U.S. Patent Application Ser. No. 62/786,166 filed on Dec. 28, 2018, entitled "ANALYTE SENSOR WITH IMPEDANCE DETERMINATION," which is incorporated herein by reference in its entirety. Referring to the method 3000, a sensor session may be aborted if the analyte sensor was exposed to humidity outside of a determined range. Further, a peak humidity to which the analyte sensor was exposed may be used to determine the initial sensor session parameter.

In some examples, a diode can be used as a temperature sensor. A diode can be used as a temperature sensor, for example, by exploiting the temperature dependency of the voltage drop across a diode. Consider the Shockley diode equation, given by Equation 2 below:

$$I = I_S \left( e^{\frac{V_D}{nV_T}} - 1 \right) \quad \text{Equation 2}$$

In Equation 2, $V_T$ is given by Equation 3 below:

$$V_T = \frac{kT}{q} \qquad \text{Equation 3}$$

In Equation 2 and Equation 3, I is the forward current through the diode. $I_s$ is the reverse bias saturation current. $V_D$ is the voltage across the diode. $V_T$ is the thermal voltage, given by Equation 3. n is the ideality factor of the diode. k is Boltzmann's constant. q is the elementary electron charge. T is the absolute temperature (in Kelvin) of the diode. Rearranging Equations 2 and 3 for voltage yields Equation 4 below:

$$V_D(I, T) = \frac{kT}{q} \ln\left(\frac{I}{I_S(T)}\right) \qquad \text{Equation 4}$$

To remove the unknown reverse bias saturation current, two known diode currents can be provided to the diode, with the difference in voltage at the two different known currents indicated as $\Delta V_D$ and given by Equation 5:

$$\Delta V_D = V_2 - V_1 = \frac{kT}{q} \ln\left(\frac{I2}{I1}\right) \qquad \text{Equation 5}$$

Solving for temperature yields:

$$T = \frac{q}{nk} \frac{\Delta V_D}{\ln\left(\frac{I2}{I1}\right)} \qquad \text{Equation 6}$$

In some examples, the dependency of temperature T on the ideality factor n of the diode can be reduced by using a diode-connected NPN transistor with the base connected to the collector (e.g., "diode-connected") as the diode. In this arrangement, the ideality factor n approaches unity and may be dropped from Equation 6.

Various examples utilize the relationship of Equation 6 to use a diode to measure temperature at an analyte sensor system. For example, an NPN transistor and associated circuitry described herein may be less expensive and, in some examples, much less expensive than a suitably accurate temperature sensor.

Figure 31:
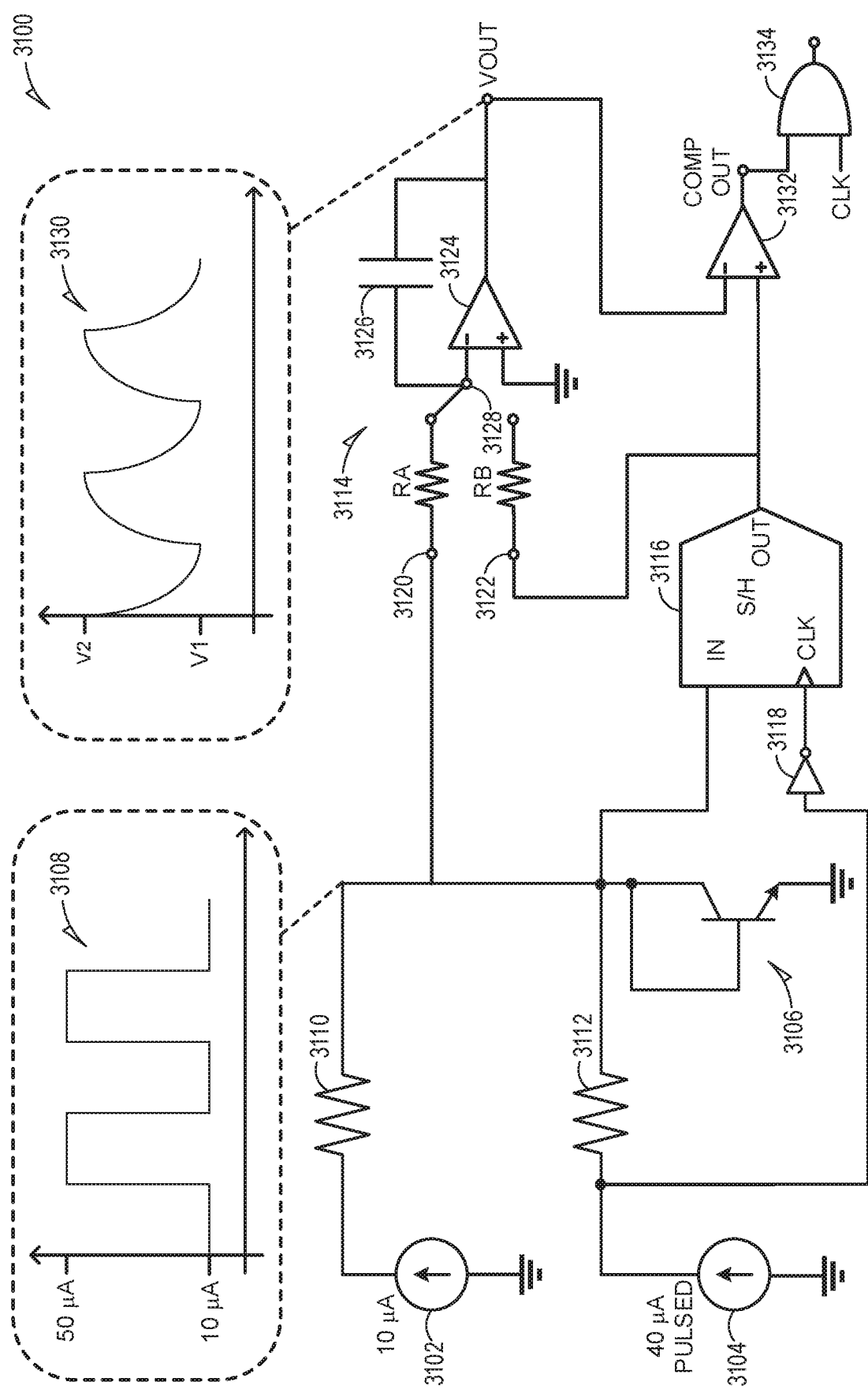
FIG. 31 is an illustration of an example circuit arrangement that can be implemented at an analyte sensor system to measure temperature using a diode.

FIG. 31 is an illustration of an example circuit arrangement 3100 that can be implemented at an analyte sensor system to measure temperature using a diode. The circuit arrangement 3100 includes first and second current sources 3102, 3104 and a diode-connected NPN transistor 3106. Although a diode-connected transistor 3106 is shown in FIG. 31, in other examples different types of diodes may be used.

The current source 3102 is a constant current source that, in this example, provides a current of about 10 uA. The current source 3104 is a pulsed current source that provides a 40 uA pulse. The current sources 3102, 3104 can be implemented in any suitable manner, for example, utilizing one or more transistors. Current from the current source 3102 and the current source 3104 is provided to the diode-connected transistor 3106 such the current at the diode-connected transistor 3106 is the sum of the current from the current source 3102 and the current from the current source 3104. This is shown by the plot 3108. In this example, when the pulsed current source 3104 is on, the current provided to the diode-connected transistor 3106 is 50 uA, the sum of the constant 10 uA from current source 3102 and the pulsed 40 uA from the current source 3104. When the pulsed current source 3104 is off, the current provided to the diode-connected transistor 3106 is the 10 uA provided by the constant current course 3102. Current sources 3102, 3104, in this example, provide current via resistors 3110, 3112.

In this arrangement, as shown by the plot 3108, the diode-connected transistor 3106 receives two known currents. As demonstrated herein, the difference between a value of the voltage drop across the diode-connected transistor 3106 at the first current (V1) and a value of the voltage drop across the diode-connected transistor 3106 at the second current (V2) is indicative of the temperature of the pn junction at the diode-connected transistor 3106.

To measure the voltage difference, a sample and hold (S/H) circuit 3116 receives the voltage value indicating the voltage drop across the diode-connected transistor 3106 at an input. At a clock input, the S/H circuit 3116 receives an indication of when the pulsed current source 3104 is off. This can be accomplished, for example, by using an inverter 3118 to invert the signal generated by the pulsed current source 3104. As a result, the output of the S/H circuit 3116 may be the voltage value V1 indicating the voltage drop across the diode-connected transistor 3106 at the current provided by the first current source 3102.

A dual slope integrating analog-to-digital converter (ADC) 3114 can be used to convert a difference between the voltage value V1 and the voltage value V2 to a digital signal that can be consumed, for example, by a processor of the analyte sensor system. The dual slope integrating ADC 3114 comprises a first input 3120 and a second input 3122. A comparator 3124 has a non-inverting input that is tied to ground and an inverting input that is coupled to a switch 3128. The switch 3128 alternately connects the first input 3120 (via resistor RA) or the second input 3122 (via resistor RB) to the inverting input. A capacitor 3126 is coupled between the inverting input of the comparator 3124 and the output VOUT of the ADC 3114.

In the example of FIG. 31, the output of the S/H circuit 3116 representing V1 is provided to the input 3122 of the ADC 3114. The voltage drop across the diode-connected transistor 3106 is provided at the input 3120. The switch 3128 is clocked to provide the input 3120 to the inverting input of the comparator 3124 when the pulsed current source 3104 is on and to provide the input 3122 to the inverting input when the current source 3104 is off.

Accordingly, when the current source 3104 is off, the capacitor 3126 is charged to the voltage V1, which is the voltage drop across the diode-connected transistor 3106 from the current source 3102. When the current source 3104 is on, the switch 3128 connects the input 3120 to the inverting input, causing the capacitor 3126 to be charged to the voltage V2, which is the voltage drop across the diode connected transistor 3106 due to the combined current of the current sources 3102, 3104. When the current source 3104 is again off, the switch 3128 connects the voltage V1 and the voltage at the capacitor 3126 (and also VOUT) decays to V1. This is indicated by plot 3130, which shows VOUT on the vertical axis and time on the horizontal axis. When VOUT is growing, the current source 3104 is on and the switch 3128 is connecting V2 at the inverting input. When VOUT is decaying, the current source 3104 is off and the switch 3128 is connecting V1 at the inverting input. The time that it takes for VOUT to decay from V2 to V1 indicates a difference between V2 and V1. This may be used to derive temperature at the diode-connected transistor 3106, for example, according to Equation 6 above.

In some examples, the circuit arrangement 3100 includes a comparator 3132 that compares the output of the S/H circuit 3116 that indicates the voltage value V1 and the VOUT output of the ADC 3114. The output of the comparator (COMP OUT) may change state when VOUT is equal to or less than V1. Accordingly, the sensor electronics of an analyte sensor system can measure the difference between V1 and V2 by starting a digital counter when the switch 3128 connects to input 3122 and stopping the digital counter when the comparator output COMP OUT changes state.

In some examples, an AND gate 3134 is provided to generate a logical AND of the comparator output (COMP OUT) and a clock signal. The output of the AND gate 3134 can be used to stop the digital counter. This may ensure that the state of the comparator changes only when the voltage on the capacitor 3126 is decaying.

Figure 32:
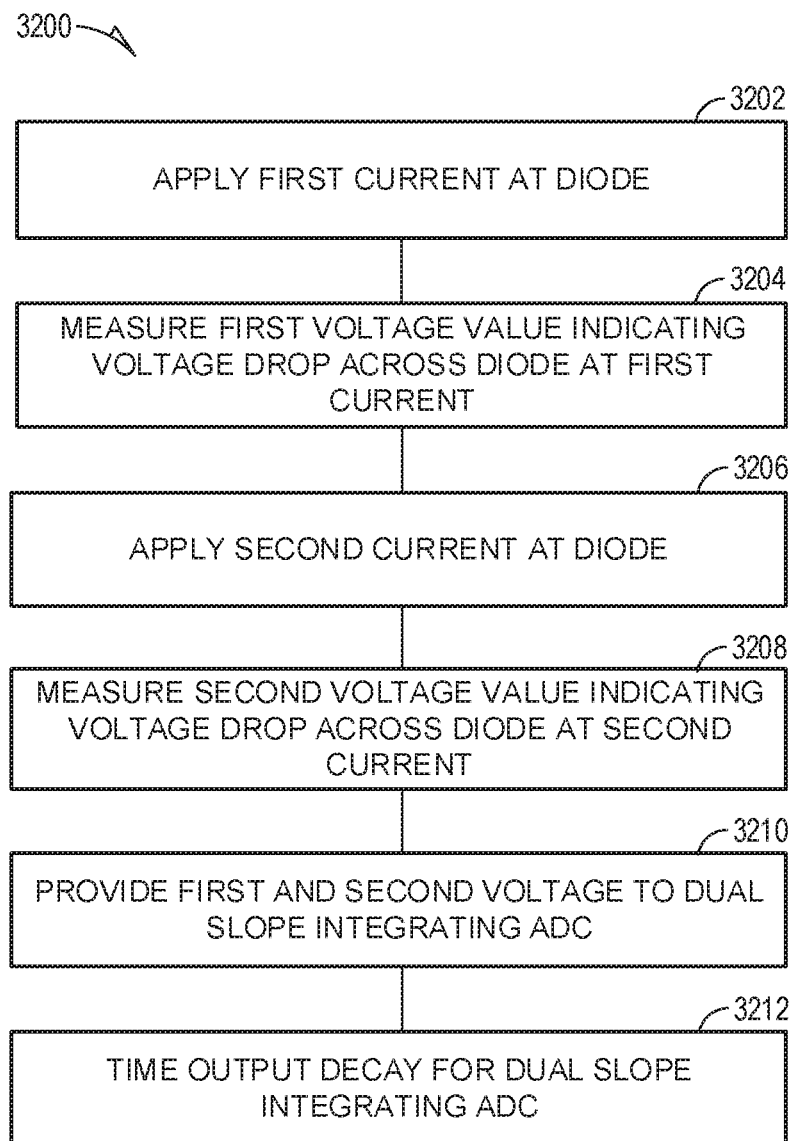
FIG. 32 is a flowchart illustration of a method for measuring temperature at an analyte sensor system using a diode.

FIG. 32 is a flowchart illustration of a method 3200 for measuring temperature at an analyte sensor system using a diode, such as the diode connected transistor 3106 of FIG. 31. The method 3200 may include, at 3202, applying a first current at a diode. The method 3200 may also include, at 3204, measuring a voltage V1 indicating a voltage drop across the diode at the first current. The method 3200 may also include applying a second current at the diode (3206) and measuring a second voltage V2 indicating a voltage drop across the diode at the second current (3208).

The first voltage V1 and second voltage V2 are provided to a dual slope integrating ADC at 3210. At 3212, a time for the output of the ADC to decay from the second voltage V2 to the first voltage V1 is measured, for example, using a digital timer. The result may be a digital value indicating the temperature at the diode, as described herein.

As described herein, one way that temperature can affect the performance of an analyte sensor system, such as a glucose sensor system, relates to a temperature-dependent compartment bias. A glucose sensor is inserted into the skin of a host at an insertion site. Under the host's skin, the glucose sensor directly measures the glucose concentration at the insertion site, for example, at the interstitial fluid present at the insertion site. The concentration of glucose in the interstitial fluid, however, may not be the same as the concentration of glucose in t the patient's blood. Compartment bias indicates a difference between the glucose concentration at the insertion site of the glucose sensor and the host's blood glucose concentration.

Compartment bias may occur due to glucose consumption by cells at the host. For example, glucose from the host's blood stream is provided to the host's cells at capillaries of the host's vascular system. Glucose diffuses from the capillaries to the host's cells. Cells between the nearest capillary or capillary system and the insertion site consume glucose. Because of this consumption, the glucose concentration at the insertion site, also called the interstitial glucose concentration, is lower than the blood glucose concentration, also referred to as the blood glucose concentration or capillary glucose concentration. The amount by which the interstitial glucose concentration is lower than the blood glucose concentration is the compartment bias.

In some examples, the rate at which glucose diffuses from the host's capillaries to the insertion site and/or the rate at which cells between the host's capillaries and the insertion site consume glucose varies with temperature. For example, when the host's skin is warmer, glucose may diffuse faster. As a result, a glucose sensor system can apply a compartment model that compensates a glucose sensor signal for compartment bias may depend on temperature. An example compartment model is given by Equation 7:

$$\frac{dIG(t)}{dt} = \frac{BG(t)}{\tau_1} - \frac{IG(t)}{\tau_2} \qquad \text{Equation 7}$$

In Equation 7, IG(t) is the interstitial glucose concentration.

$$\frac{dIG(t)}{dt}$$

is the first derivative of the interstitial glucose concentration IG(t) over time. BG(t) is the blood glucose. The values $\tau_1$ and $\tau_2$ are model time parameters. Equation 7 is a differential equation that may be solved to derive a model relationship between interstitial glucose concentration IG and blood glucose concentration BG as given by Equation 8:

$$IG(t) = \frac{1}{\tau_1} e^{\frac{-t}{\tau_2}} * BG(t) \qquad \text{Equation 8}$$

The time parameters $\tau_1$ and $\tau_2$ may depend on temperature. For example, a glucose sensor system can model the time parameters $\tau_1$ and $\tau_2$ as a function of temperature. When the glucose sensor system receives a glucose sensor signal and a temperature sensor signal, the glucose sensor system may utilize the temperature sensor signal to derive the time parameters $\tau_1$ and $\tau_2$ and then use the time parameters in a compartment model, such as that given by Equations 7 and 8 to find a compensated glucose concentration.

In some examples, a glucose sensor system utilizes a compartment model that includes a single time parameter $\tau$ that applies to both the interstitial glucose concentration term IG and the blood glucose concentration term BG. In some examples, the difference between the time parameters $\tau_1$ and $\tau_2$ of the compartment model of Equations 7 and 8 is related to the glucose consumption of cells between the host's capillaries and the insertion site. Accordingly, in some examples, a single time parameter $\tau$ can be used by accounting for the glucose consumption. An example compartment model that accounts for glucose consumption is given by Equation 9:

$$\frac{dIG(t)}{dt} = \frac{BG(t)}{\tau} - \frac{IG(t)}{\tau} - C(t) \qquad \text{Equation 9}$$

In Equation 9, C(t) is a consumption term.

The consumption term C(t), in some examples, can be modeled as given by Equation 10:

$$C(t) = \sum_{i=1}^{n} \frac{V_{max}[s_i]}{K_m + [s_i]} \qquad \text{Equation 10}$$

In Equation 10, $V_{max}$ is the maximum consumption rate of the hosts cells. $K_m$ is the glucose concentration at which the consumption rate is half of $V_{max}$. $[s_i]$ is the cell layer glucose concentration at the ith cell layer between the host's capillary and the insertion cite. As shown in Equation 10, summing over the number n of cells per unit volume (e.g., per dL) gives the consumption.

Figure 33:
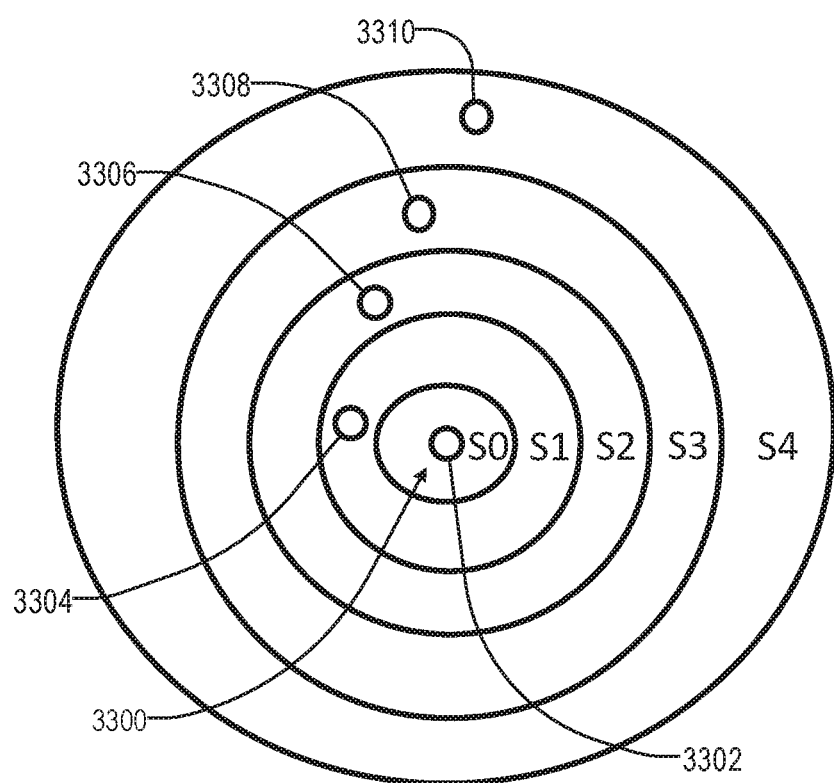
FIG. 33 illustrates an example sensor insertion site showing cell layers between the sensor insertion site and the host's capillary site.

FIG. 33 illustrates an example sensor insertion site 3300 showing cell layers between the sensor insertion site 3300 and the host's capillary site. In this example, five cell layers are shown for i=0-4. Cells at the layer 0, such as cell 3302, have a cell layer glucose concentration S0. Cells at the layer 1, such as the example cell 3304, have a cell layer glucose concentration S1. Cells at the layer 2, such as the example cell 3306, have a cell layer glucose concentration S2. Cells at the layer 3, such as the example cell 3308, have a cell layer glucose concentration S3. Cells at layer 4, such as the example cell 3310, have a cell layer glucose concentration S4.

In some examples, a glucose sensor system can apply Equations 9 and 10 assuming that the cell layer glucose concentration [si] is constant independent of distance from the sensor insertion site. For example, in some examples, it is assumed that the cell layer glucose concentration [si] for all cells is the average of the interstitial glucose concentration IG and the blood glucose concentration. With this assumption, Equations 9 and 10 can be approximated as given by Equation 11:

$$\frac{dIG(t)}{dt} = \frac{BG(t)}{\tau} - \frac{IG(t)}{\tau} - n \times \frac{V_{max} \times \frac{BG+IG}{2}}{K_m + \frac{BG+IG}{2}} \quad \text{Equation 11}$$

Solving Equation 11 for blood glucose concentration yields a model that can be used to generate a compensated glucose concentration. For example, a glucose sensor system can utilize a temperature sensor signal to determine a value for $\tau$ and then apply $\tau$ to the solution of Equation 11 to generate a compensated glucose concentration.

In other examples, a glucose sensor system can apply Equations 9 and 10 assuming that the consumption term from the sum of Equation 10 is a linear function of i, for example, as illustrated by Equation 12:

$$\frac{V_{max}[si]}{K_m + [si]} = a \times i + b \quad \text{Equation 12}$$

In Equation 12, a is a slope and b is an offset. Given this assumption, the consumption given by Equation 10 above reduces to the form shown by Equation 13:

$$C(t) = \frac{n}{2}\left(\frac{V_{max}IG}{K_M + IG} + \frac{V_{max}BG}{K_M + BG}\right) \quad \text{Equation 13}$$

and the compartment bias model is indicated by Equation 14:

$$\frac{dIG(t)}{dt} = \frac{BG(t)}{\tau} - \frac{IG(t)}{\tau} - \frac{n}{2}\left(\frac{V_{max}IG}{K_M + IG} + \frac{V_{max}BG}{K_M + BG}\right) \quad \text{Equation 14}$$

Solving Equation 14 for blood glucose concentration yields a model that can be used to generate a compensated glucose concentration. For example, a glucose sensor system can utilize a temperature sensor signal to determine a value for $\tau$ and then apply $\tau$ to the solution of Equation 14 to generate a compensated glucose concentration.

Any of the methods described herein or illustrated may include delivering a therapy, such as delivering insulin (e.g., using a wearable pump or a smart pen), based at least in part on a determined temperature-compensated glucose concentration level. For example, a temperature-compensated glucose level may be provided to a pump, smart pen, or other device, which may use the temperature-compensated glucose level to determine a therapy. The methods may also be combined (e.g., in serial or parallel form), or may be blended together to form an aggregate method that combines two or more methods.

The systems, devices, and methods described herein may be applied to any type of analyte sensor or any type of glucose sensor. Any specific reference to "glucose sensor" or "analyte sensor" or "glucose monitor" should be understood as being applicable to any glucose sensor, analyte sensor, glucose monitor, or other sensor that is subject to temperature effects. For example, a method described in the context of a glucose sensor is also applicable to other types of analyte sensors.

While the methods of evaluating or correcting temperature measurements have been described in the context of physiological sensors and temperature compensation, the methods may also be applied in other contexts where temperature information and accuracy of temperature information is relevant. For examples, the methods may be applied to the use of temperature devices in smart devices, such as hand held devices, smart phones, vehicles, watches, smart glasses or other wearable devices.

Each of these non-limiting examples can stand on its own or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method of determining a temperature-compensated glucose concentration level, the method comprising:
    receiving a temperature signal indicative of a temperature parameter of an external component at a first time;
    receiving a glucose signal indicative of an in vivo glucose concentration level at a second time after the first time;
    determining a delay parameter, wherein the delay parameter includes a delay time period between the first time and the second time that accounts for a delay between a first temperature change at the external component and a second temperature change proximate a glucose sensor;
    determining, using a processor, a compensated glucose concentration level based on the glucose signal, the temperature signal, and a delay parameter;
    enabling a wireless communication using a wireless radio protocol between the processor and a receiver; and
    outputting, via the wireless communication, the compensated glucose concentration level to the receiver.

2. The method of claim 1, wherein the temperature parameter is a temperature, a temperature change, or a temperature offset.

3. The method of claim 1, further comprising adjusting the delay time period based upon a temperature rate of change.

4. The method of claim 1, further comprising adjusting the delay time period based upon a detected condition.

5. The method of claim 4, wherein the detected condition includes a sudden change in temperature.

6. The method of claim 4, wherein the detected condition includes exercise.

7. The method of claim 1, wherein receiving a glucose signal includes receiving a glucose signal from a wearable glucose sensor.

8. The method of claim 7, wherein detecting a temperature signal includes measuring a temperature parameter of a component of the wearable glucose sensor.

9. The method of claim 1, wherein determining a compensated glucose concentration level includes executing instructions on a processor to receive the glucose signal and the temperature signal and determine the compensated glucose concentration level using the glucose signal, the temperature signal, and the delay parameter.

10. The method of claim 1, wherein the method includes storing a value corresponding to the temperature parameter in a memory circuit, and retrieving the stored value from the memory circuit for use in determining the compensated glucose concentration level.

11. The method of claim 1, further comprising delivering a therapy based at least in part on the compensated glucose concentration level.

12. The method of claim 1 wherein the wireless radio protocol is Bluetooth, Bluetooth Low-Energy, or Near Field Communication (NFC).

13. A temperature-compensated glucose sensor system comprising:
    a glucose sensor configured to generate a glucose signal representative of an in vivo glucose concentration level;
    a temperature sensor configured to generate a temperature signal indicative of a temperature parameter of an external component;
    a processor configured to:
        receive the temperature signal from the temperature sensor,
        receive the glucose signal from the glucose sensor, and
        determine a compensated glucose concentration level based on the glucose signal, the temperature signal, and a delay parameter, wherein the temperature parameter is detected at a first time and the glucose concentration level is detected at a second time after the first time, wherein the delay parameter includes a delay time period between the first time and the second time that accounts for a delay between a first temperature change at the external component and a second temperature change proximate a glucose sensor.

14. The system of claim 13, wherein the temperature parameter is a temperature, a temperature change, or a temperature offset.

15. The system of claim 13, further comprising adjusting the delay time period based upon a temperature rate of change.

16. The system of claim 13, further comprising adjusting the delay time period based upon a detected condition.

17. The system of claim 16, wherein the detected condition includes exercise.

18. The system of claim 17, wherein detecting a temperature signal includes measuring a temperature parameter of a component of the wearable glucose sensor.

19. The system of claim 13, further comprising a memory configured to store a value corresponding to the temperature parameter, and wherein the processor is configured to retrieve the stored value from the memory for use in determining the compensated glucose concentration level.

20. The system of claim 13, wherein the processor is further configured to communicate with a delivery device to deliver a therapy based at least in part on the compensated glucose concentration level.

\* \* \* \* \*